(12) United States Patent
Vendeville et al.

(10) Patent No.: US 11,952,374 B2
(45) Date of Patent: Apr. 9, 2024

(54) BICYCLIC COMPOUNDS

(71) Applicant: Aligos Therapeutics, Inc., South San Francisco, CA (US)

(72) Inventors: Sandrine Vendeville, Brussels (BE); Pierre Jean-Marie Bernard Raboisson, Wavre (BE); David McGowan, Brussels (BE)

(73) Assignee: Aligos Therapeutics, Inc., South San Francisco, CA (US)

( * ) Notice: Subject to any disclaimer, the term of this patent is extended or adjusted under 35 U.S.C. 154(b) by 22 days.

(21) Appl. No.: 17/451,462

(22) Filed: Oct. 19, 2021

(65) Prior Publication Data
US 2022/0119385 A1   Apr. 21, 2022

Related U.S. Application Data

(60) Provisional application No. 63/094,533, filed on Oct. 21, 2020.

(51) Int. Cl.
| | |
|---|---|
| *C07D 471/04* | (2006.01) |
| *A61K 31/519* | (2006.01) |
| *A61K 31/5377* | (2006.01) |
| *A61K 31/5395* | (2006.01) |
| *A61K 45/06* | (2006.01) |
| *A61P 31/14* | (2006.01) |
| *C07D 498/22* | (2006.01) |

(52) U.S. Cl.
CPC .......... *C07D 471/04* (2013.01); *A61K 31/519* (2013.01); *A61K 31/5377* (2013.01); *A61K 31/5395* (2013.01); *A61K 45/06* (2013.01); *A61P 31/14* (2018.01); *C07D 498/22* (2013.01)

(58) Field of Classification Search
CPC .... C07D 498/22; C07D 471/04; A61K 45/06; A61K 31/5395; A61K 31/5377; A61K 31/519; A61P 31/14
See application file for complete search history.

(56) References Cited

U.S. PATENT DOCUMENTS

| | | |
|---|---|---|
| 6,414,157 B1 | 7/2002 | Lubisch et al. |
| 6,657,063 B1 | 12/2003 | Dow |
| 2005/0054645 A1 | 3/2005 | Miyazaki et al. |
| 2005/0165025 A1 | 7/2005 | Leonardi et al. |
| 2010/0093771 A1 | 4/2010 | Nakamura et al. |
| 2020/0147124 A1 | 5/2020 | Beigelman et al. |
| 2021/0403461 A1 | 12/2021 | Iwata et al. |

FOREIGN PATENT DOCUMENTS

| | | |
|---|---|---|
| CN | 109956930 | 7/2019 |
| CN | 111039942 | 4/2020 |
| DE | 19747063 | 4/1999 |
| WO | WO 99/02990 | 1/1999 |
| WO | WO 2001/089570 | 11/2001 |
| WO | WO 2005/016927 | 2/2005 |
| WO | WO 2008/038768 | 4/2008 |
| WO | WO 2008/130581 | 10/2008 |
| WO | WO 2022/053010 | 7/2018 |
| WO | WO 2019/022061 | 1/2019 |
| WO | WO 2020/182990 | 9/2020 |
| WO | WO-2020182990 A1 * | 9/2020 ........... A61K 31/519 |
| WO | WO 2021/178885 | 9/2021 |
| WO | WO 2022/087011 | 3/2022 |

OTHER PUBLICATIONS

Sweet, Miles J. "The Patentability of Chiral Drugs Post-KSR: The More Things Change, the More They Stay the Same." Berkeley Technology Law Journal, vol. 24, No. 1, 2009, pp. 129-147. JSTOR, http://www.jstor.org/stable/24121329. (Year: 2009).*
International Search Report and Written Opinion dated Nov. 25, 2021 for PCT Application No. PCT/US2021/055674, filed Oct. 19, 2021.
"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5) :942-944.
Liang, "Hepatitis B: The Virus and Disease" Hepatology (2009) 49(S5):S13-S21.
Second Written Opinion dated Aug. 26, 2022 for PCT Application No. PCT/US2021/055674, filed Oct. 19, 2021.
International Preliminary Report on Patentability completed Jan. 27, 2023 for PCT Application No. PCT/US2021/055674, filed Oct. 19, 2021.

* cited by examiner

*Primary Examiner* — Bahar Craigo
*Assistant Examiner* — Manahil Mirghani Ali Abdalhameed
(74) *Attorney, Agent, or Firm* — Knobbe, Martens, Olson & Bear LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

21 Claims, No Drawings
Specification includes a Sequence Listing.

BICYCLIC COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 63/094,533, filed Oct. 21, 2020.

REFERENCE TO SEQUENCE LISTING

The present application is filed with a Sequence Listing in Electronic format. The Sequence Listing is provided as a file entitled ALIG059.txt, created Oct. 19, 2021, which is approximately 8 kb in size. The information in the electronic format of the sequence listing is incorporated herein by reference in its entirety.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

The hepatitis B virus (HBV) is a DNA virus and a member of the Hepadnaviridae family. HBV infects more than 300 million worldwide, and is a causative agent of liver cancer and liver disease such as chronic hepatitis, cirrhosis, and hepatocellular carcinoma. Although there are approved drugs for treating HBV, by either boosting the immune system or slowing down the replication of the HBV virus, HBV continues to be a problem due to the drawbacks associated with each of the approved drugs.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below.

DETAILED DESCRIPTION

HBV is a partially double-stranded circular DNA of about 3.2 kilobase (kb) pairs, and is classified into eight genotypes, A to H. The HBV replication pathway has been studied in great detail. T. J. Liang, Hepatology (2009) 49(5 Suppl): S13-S21. On part of replication includes the formation of the covalently closed circular (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of a HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure a HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3) individually and independently selected from deuterium, alkyl, alkenyl, alkynyl, cycloalkyl, cycloalkenyl, aryl, heteroaryl, heterocyclyl, aryl(alkyl), heteroaryl(alkyl), heterocyclyl(alkyl), hydroalkyl, hydroxy, alkoxyalkyl, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, C-amido(alkyl), isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group, a di-substituted amino group, an unsubstituted C-amido($C_{1-3}$ alkyl), —O-(an unsubstituted $C_{1-4}$ alkyl)-OH, —O-(an unsubstituted $C_{1-4}$ alkyl)-(an unsubstituted alkoxy), —O-(an unsubstituted $C_{1-4}$ alkyl)-(an unsubstituted C-carboxy), —O—($C_{1-3}$ alkyl)-O-(an unsubstituted C-amido), —O-(an unsubstituted $C_{1-4}$ alkyl)-$NH_2$, —O-(an unsubstituted $C_{1-4}$ alkyl)-NH (an unsubstituted $C_{1-4}$ alkyl), —O-(an unsubstituted $C_{1-4}$ alkyl)-N (an unsubstituted $C_{1-4}$ alkyl)$_2$ and an unsubstituted —O-(an unsubstituted $C_{1-4}$ alkyl)-CN.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "heterocyclyl(alkyl)" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group with a substituent(s) listed under the definition of "substituted." Further, when a lower alkylene group is substituted, the lower alkylene can be substituted by replacing both hydrogens on the same carbon with a cycloalkyl group (e.g.,

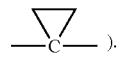

).

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. In some instances, an alkoxy can be —OR, wherein R is an unsubstituted $C_{1-4}$ alkyl. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "alkoxyalkyl" refers to an alkyl group in which one or more of the hydrogen atoms are replaced by an alkoxy group. Exemplary alkoxyalkyl groups include but are not limited to, methoxymethyl, ethoxymethyl, methoxyethyl and ethoxyethyl. An alkoxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group and O-monocyclic cycloalkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoro-2-ethoxy, trifluoromethoxy, 1-chloro-2-fluoromethoxy, 2-fluoroisobutoxy, chloro-substituted cyclopropyl, fluoro-substituted cyclopropyl, chloro-substituted cyclobutyl and fluoro-substituted cyclobutyl. In some instances, a haloalkoxy can be —OR, wherein R is a $C_{1-4}$ alkyl substituted by 1, 2 or 3 halogens. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(═O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C(=O) group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

A "mono-substituted amine" refers to a "—NHR$_A$" in which R$_A$ can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —NHR$_A$, wherein R$_A$ can be an unsubstituted C$_{1-6}$ alkyl or an unsubstituted or a substituted benzyl.

A "di-substituted amine" refers to a "—NR$_A$R$_B$" in which R$_A$ and R$_B$ can be independently can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —NR$_A$R$_B$, wherein R$_A$ and R$_B$ can be independently an unsubstituted C$_{1-6}$ alkyl or an unsubstituted or a substituted benzyl.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

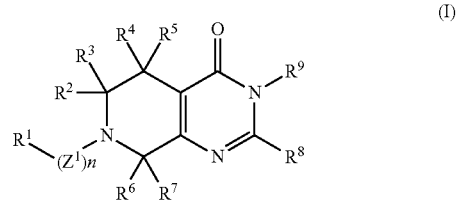

wherein: n can be 0 or 1; $Z^1$ can be —C(=O)—, —NH—C(=O)—, —O—C(=O)—, —OCH$_2$C(=O)—, —CH=CHC(=O)— or —CH(CF$_3$)—; $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^2$ and $R^3$ can be independently selected from hydrogen, an unsubstituted $C_{1-4}$ alkyl, an unsubstituted $C_{1-4}$ haloalkyl, an optionally substituted monocyclic $C_{3-6}$ cycloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^4$ and $R^5$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^6$ and $R^7$ can be independently selected from hydrogen, an unsubstituted $C_{1-4}$ alkyl and an unsubstituted $C_{1-4}$ haloalkyl; $R^8$ can be selected from a hydroxy-$C_{1-6}$ alkyl, an optionally substituted alkoxy, an optionally substituted monocyclic $C_{3-6}$ cycloalkyl, an optionally substituted phenyl, an optionally substituted monocyclic heteroaryl, an optionally substituted monocyclic heterocyclyl, an optionally substituted 6-17 member bicyclic heterocyclyl, an optionally substituted monocyclic $C_{3-6}$ cycloalkyl($C_{1-4}$ alkyl), an optionally substituted aryl($C_{1-4}$ alkyl), an optionally substituted monocyclic heteroaryl($C_{1-4}$ alkyl), an optionally substituted monocyclic heterocyclyl ($C_{1-4}$ alkyl), an optionally substituted 6-17 member bicyclic heterocyclyl($C_{1-4}$ alkyl), an optionally substituted aryloxy($C_{1-4}$ alkyl), —OR$^{10}$, —SR$^{11}$, —C(=O)NHR$^{13}$ and —NR$^{14A}$R$^{14B}$, wherein the $C_{1-4}$ alkyl of the optionally substituted monocyclic $C_{3-6}$ cycloalkyl($C_{1-4}$ alkyl), the $C_{1-4}$ alkyl of the optionally substituted aryl($C_{1-4}$ alkyl), the optionally substituted monocyclic heteroaryl($C_{1-4}$ alkyl), the optionally substituted monocyclic heterocyclyl ($C_{1-4}$ alkyl) and the $C_{1-4}$ alkyl of the optionally substituted 6-17 member bicyclic heterocyclyl($C_{1-4}$ alkyl) can be optionally substituted with an unsubstituted $C_{1-3}$ alkyl or an unsubstituted $C_{3-4}$ monocyclic cycloalkyl; $R^9$ can be a substituted phenyl, a substituted monocyclic heteroaryl or a substituted fused-bicyclic heteroaryl, wherein the substituted phenyl, the substituted monocyclic heteroaryl or the substituted fused-bicyclic heteroaryl can be substituted with one or more substituents selected from halogen, an unsubstituted $C_{1-4}$ alkyl, an unsubstituted $C_{1-4}$ haloalkyl, an unsubstituted $C_{1-4}$ alkoxy, an optionally substituted monocyclic heteroaryl, an optionally substituted monocyclic heterocyclyl, amino, a mono-substituted amine, a di-substituted amine and —C(=O)NHR$^{15}$; R$^{10}$ and R$^{11}$ can be independently selected from an unsubstituted $C_{1-6}$ alkyl, an optionally substituted monocyclic $C_{3-6}$ cycloalkyl, an optionally substituted aryl, an optionally substituted heteroaryl, an optionally substituted heterocyclyl, an optionally substituted monocyclic $C_{3-8}$ cycloalkyl($C_{1-4}$ alkyl), an optionally substituted aryl($C_{1-4}$ alkyl), an optionally substituted heteroaryl ($C_{1-4}$ alkyl) and an optionally substituted heterocyclyl($C_{1-4}$ alkyl), wherein the $C_{1-4}$ alkyl of the optionally substituted monocyclic $C_{3-8}$ cycloalkyl($C_{1-4}$ alkyl), the optionally substituted aryl($C_{1-4}$ alkyl), the optionally substituted heteroaryl ($C_{1-4}$ alkyl) and the optionally substituted heterocyclyl($C_{1-4}$ alkyl) can be optionally substituted with an unsubstituted $C_{1-3}$ alkyl, a monocyclic $C_{3-6}$ cycloalkyl optionally substituted with one or more substituents selected from halogen, hydroxy, an unsubstituted $C_{1-3}$ alkyl, unsubstituted $C_{1-3}$ alkoxy, amino, $C_{1-4}$ alkylamino and an optionally substituted 4-6 membered monocyclic heterocyclyl; R$^{13}$ can be selected from an unsubstituted $C_{1-6}$ alkyl, an optionally substituted aryl, an optionally substituted monocyclic $C_{3-6}$ cycloalkyl ($C_{1-4}$ alkyl), an optionally substituted aryl($C_{1-4}$ alkyl), an optionally substituted heteroaryl($C_{1-4}$ alkyl) or an optionally substituted heterocyclyl($C_{1-4}$ alkyl), wherein the $C_{1-4}$ alkyl of the optionally substituted monocyclic $C_{3-6}$ cycloalkyl ($C_{1-4}$ alkyl), the optionally substituted aryl($C_{1-4}$ alkyl), the optionally substituted heteroaryl($C_{1-4}$ alkyl) and the optionally substituted heterocyclyl($C_{1-4}$ alkyl) can be optionally substituted with an unsubstituted $C_{1-3}$ alkyl or an unsubstituted $C_{3-4}$ monocyclic cycloalkyl; R$^{14A}$ can be hydrogen, an unsubstituted $C_{1-6}$ alkyl, an unsubstituted $C_{2-6}$ alkenyl, a monocyclic $C_{3-6}$ cycloalkyl optionally substituted with one or two halogens, a monocyclic $C_{3-6}$ cycloalkyl($C_{1-4}$ alkyl) optionally substituted with one or two halogens, an optionally substituted 5-6 member monocyclic heteroaryl, an optionally substituted 4-6 member monocyclic heterocyclyl or an optionally substituted monocyclic 4- to 6-membered heterocyclyl($C_{1-4}$ alkyl); R$^{14B}$ can be selected from an unsubstituted $C_{1-6}$ alkyl, an optionally substituted aryl, an optionally substituted monocyclic $C_{3-6}$ cycloalkyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl), wherein the $C_{1-4}$ alkyl of the optionally substituted monocyclic $C_{3-6}$ cycloalkyl ($C_{1-4}$ alkyl), the optionally substituted aryl($C_{1-4}$ alkyl), the optionally substituted heteroaryl($C_{1-4}$ alkyl) and the optionally substituted heterocyclyl($C_{1-4}$ alkyl) can be optionally substituted with an unsubstituted $C_{1-3}$ alkyl or an unsubstituted $C_{3-4}$ monocyclic cycloalkyl; and R$^{15}$ can be hydrogen, an unsubstituted $C_{1-6}$ alkyl, an optionally substituted $C_{2-6}$ alkenyl, an optionally substituted $C_{1-6}$ alkynyl or an optionally substituted monocyclic $C_{3-6}$ cycloalkyl.

As provided herein, various groups can be attached to the piperidinyl ring of the ring structure of Formula (I). In some embodiments, n can be 0; and R$^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl) such that Formula (I), and pharmaceutically acceptable salts thereof can be Formula (Ia), or a pharmaceutically acceptable salt thereof. In other embodiments, n can be 1; Z$^1$ can be —C(=O)—, —NH—C(=O)— or —O—C(=O)—; and R$^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl). As shown below, when Z$^1$ is —C(=O)—, —NH—C (=O)— or —O—C(=O)—, Formula (I) can be Formula (Ib), (Ic) or (Id), or a pharmaceutically acceptable salt thereof, respectively. In still other embodiments, when n can be 1; and Z$^1$ is —OCH$_2$C(=O)— or —CH=CHC(=O)—, Formula (I) can be Formula (Ie) and (If), respectively. In yet still other embodiments, when n can be 1; and Z$^1$ is —C(CF$_3$)—, Formula (I) can be Formula (Ig).

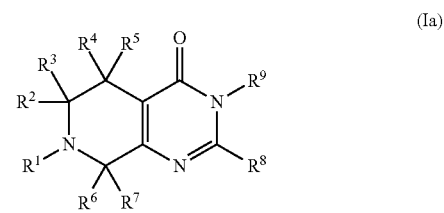

(Ia)

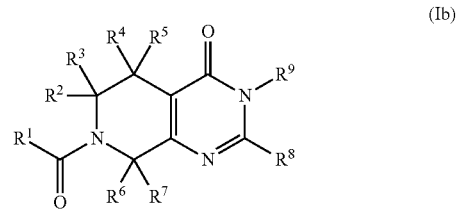

(Ib)

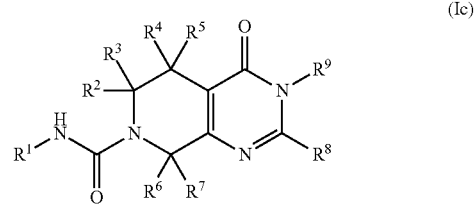

(Ic)

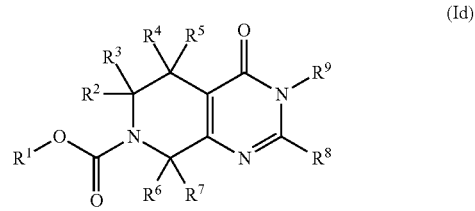

(Id)

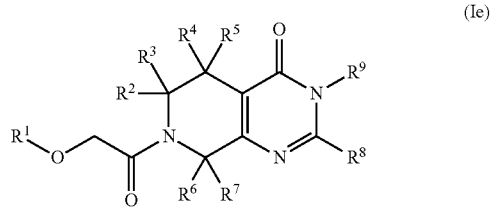

(Ie)

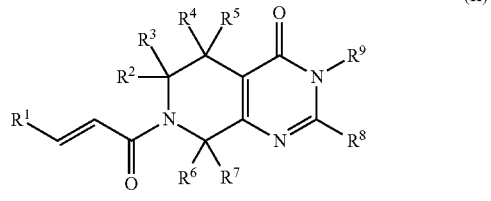

(If)

-continued

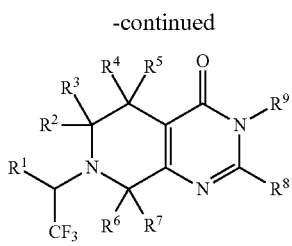

(Ig)

Various cyclic moieties can be present for $R^1$. In some embodiments, $R^1$ can be a carbocyclic moiety, for example an optionally substituted aryl. For example, $R^1$ can be an optionally substituted phenyl. In some embodiments, $R^1$ can be an unsubstituted phenyl. In other embodiments, $R^1$ can be a substituted phenyl. When $R^1$ is a substituted phenyl, the phenyl can be mono-substituted. The mono-substituted phenyl can be a para-substituted phenyl, a meta-substituted phenyl or an ortho-substituted phenyl. The substituted phenyl can be substituted by multiple moieties, such as 2, 3 or more than 3 times. For example, the substituted phenyl of $R^1$ can be di-substituted (such as a meta- and para-substituted phenyl). When more than one moiety is present, the moieties can be the same or different moieties can be different.

As described herein, $R^1$ can be a cyclic moiety, including a cyclic moiety that can include one or more heteroatoms in the ring(s). In some embodiments, $R^1$ can be an optionally substituted heteroaryl. The heteroaryl can be monocyclic or bicyclic. In some embodiments, $R^1$ can be an unsubstituted or a substituted monocyclic heteroaryl. For example, $R^1$ can be a 5-membered or 6-membered monocyclic heteroaryl. In other embodiments, $R^1$ can be an unsubstituted or a substituted bicyclic heteroaryl. The bicyclic heteroaryl can be a 9-membered or 10-membered heteroaryl. The heteroaryl can include one or more heteroatoms, such as N (nitrogen), O (oxygen) and/or S (sulfur). In some embodiments, $R^1$ can be an optionally substituted heterocyclyl. The heterocyclyl can be a monocyclic heterocyclyl or a bicyclic heterocyclyl. In some embodiments, $R^1$ can be an unsubstituted or a substituted monocyclic heterocyclyl, such as a 5-membered or 6-membered monocyclic heterocyclyl. In other embodiments, $R^1$ can be an unsubstituted or a substituted bicyclic heterocyclyl, including a 9-membered or 10-membered heterocyclyl. The number and types of heteroatoms that can be present in a heterocyclyl can vary. As an example, 1, 2, 3 or more than 3 heteroatoms, such as N (nitrogen), O (oxygen) and/or S (sulfur), can be present in a heterocyclyl of $R^1$.

In some embodiments, $R^1$ can be selected from an unsubstituted or a substituted [5,5] bicyclic heteroaryl, an unsubstituted or a substituted [5,6] bicyclic heteroaryl, an unsubstituted or a substituted [6,5] bicyclic heteroaryl, an unsubstituted or a substituted [6,6] bicyclic heteroaryl, an unsubstituted or a substituted [5,5] bicyclic heterocyclyl, an unsubstituted or a substituted [5,6] bicyclic heterocyclyl, an unsubstituted or a substituted [6,5] bicyclic heterocyclyl and an unsubstituted or a substituted [6,6] bicyclic heterocyclyl. In some embodiments, $R^1$ can be a nitrogen-containing, bicyclic heteroaryl. In other embodiments, $R^1$ can be a nitrogen-containing, bicyclic heterocyclyl. In some embodiments, $R^1$ can have the general structure

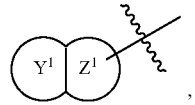

wherein Ring $Z^1$ indicates the point of attachment to the remaining portion of Formula (I); and wherein Ring $Y^1$ and Ring $Z^1$ can be independently selected from phenyl, furan, furazan, thiophene, phthalazine, pyrrole, oxazole, 1,2,3-oxadiazole, 1,2,4-oxadiazole, thiazole, 1,2,3-thiadiazole, 1,2,4-thiadiazole, imidazole, pyrazole, isoxazole, isothiazole, triazole, thiadiazole, tetrazole, pyridine, pyridazine, pyrimidine, pyrazine, 1,2,3-triazine, 1,2,4-triazine, 1,2,3,4-tetrazine, 2H-1,2-oxazine, hexahydro-1,3,5-triazine, imidazoline, imidazolidine, isoxazoline, isoxazolidine, oxazoline, oxazolidine, thiazoline, thiazolidine, morpholine, piperidine, piperazine, pyrrolidine, pyrazoline, pyrazolidine and thiamorpholine, wherein Ring $Y^1$ and Ring $Z^1$ can be each optionally substituted. In some embodiments, Ring $Y^1$ can be selected from an optionally substituted phenyl, an optionally substituted pyridine, an optionally substituted pyridazine, an optionally substituted pyrimidine, an optionally substituted pyrazine, an optionally substituted 1,2,3-triazine, an optionally substituted 1,2,4-triazine and an optionally substituted 1,2,3,4-tetrazine. In some embodiments, Ring $Z^1$ can be selected from an optionally substituted phenyl, an optionally substituted pyridine, an optionally substituted pyridazine, an optionally substituted pyrimidine, an optionally substituted pyrazine, an optionally substituted 1,2,3-triazine, an optionally substituted 1,2,4-triazine and an optionally substituted 1,2,3,4-tetrazine. In other embodiments, Ring $Z^1$ can be selected from an optionally substituted furan, an optionally substituted thiophene, an optionally substituted pyrrole, an optionally substituted oxazole, an optionally substituted thiazole, an optionally substituted imidazole, an optionally substituted pyrazole, an optionally substituted isoxazole and an optionally substituted isothiazole.

Various cyclic groups can be attached via a $C_{1-4}$ alkyl linker for $R^1$. In some embodiments, $R^1$ can be an optionally substituted aryl($C_{1-4}$ alkyl). An exemplary optionally substituted aryl($C_{1-4}$ alkyl) is an optionally substituted benzyl. In other embodiments, $R^1$ can be an optionally substituted heteroaryl($C_{1-4}$ alkyl). In still other embodiments, $R^1$ can be an optionally substituted heterocyclyl($C_{1-4}$ alkyl). Examples of heteroaryls and heterocyclyls are described herein, and include those of the previous paragraph. As described herein, the linker can include 1 to 4 carbons. In some embodiments, the $C_{1-4}$ alkyl linker for $R^1$ can be —$CH_2$—, —$CH_2CH_2$—, —$CH_2CH_2CH_2$— or —$CH_2CH_2CH_2CH_2$—. Further as described herein lower alkylene linker ($C_{1-4}$ alkyl linker) for $R^1$ can be substituted. Examples of substituents that can be present on a substituted lower alkylene linker ($C_{1-4}$ alkyl linker) for aryl($C_{1-4}$ alkyl), heteroaryl($C_{1-4}$ alkyl) and heterocyclyl($C_{1-4}$ alkyl) include an unsubstituted $C_{1-4}$ haloalkyl (such as $CF_3$).

As described herein, $R^1$ can be substituted. A variety of substituents can substitute the $R^1$ groups described herein. In some embodiments, $R^1$ can be substituted with one or more substituents independently selected from deuterium, halogen (such as F, Cl and/or Br), cyano, an unsubstituted $C_{1-6}$ alkyl (for example, methyl, ethyl, n-propyl, isopropyl, n-butyl, iso-butyl, sec-butyl, tert-butyl, pentyl (straight-changed or branched) and hexyl (straight-chained or branched)), an unsubstituted $C_{2-6}$ alkenyl (for example, ethenyl, propenyl and butenyl), an unsubstituted $C_{2-6}$ alkynyl (for example, ethynyl, propynyl and butynyl), an unsubstituted or a substituted monocyclic $C_{3-6}$ cycloalkyl (such as cyclopropyl, cyclobutyl, cyclopentyl and cyclohexyl, including halo-substituted versions of each of the aforementioned examples), an unsubstituted $C_{1-6}$ haloalkyl (such as —$CHF_2$, —$CH_2F$, —$CF_3$, —$CHClF$, —$CH_2Cl$, —$CHCl_2$, —CCl₃, —CH₂CHF₂, —CH₂CH₂F, —CH₂CF₃, —CH₂CHClF, —CH₂CH₂Cl, —CH₂CHCl₂, —CH₂CCl₃, —CH(CH₃)CF₃, —CH(CH₃)CHF₂, —C(CH₃)₂CF₃ and —C(CH₃)₂CHF₂), an unsubstituted $C_{1-6}$ alkoxy (for example, methoxy, ethoxy, isopropoxy, n-butoxy, sec-butoxy, isobutoxy, tert-butoxy, —O-(cyclopropyl), —O-(cyclobutyl) and —O-(oxetane)), an unsubstituted $C_{1-6}$ haloalkoxy (for example, —OCHF₂, —OCH₂F, —OCF₃, —OCHClF, —OCH₂Cl, —OCHCl₂, —OCCl₃, —OCH₂CHF₂, —OCH₂CH₂F, —OCH₂CF₃, —OCH₂CHClF, —OCH₂CH₂Cl, —OCH₂CHCl₂, —OCH₂CCl₃, —OCH(CH₃)CF₃, —OCH(CH₃)CHF₂, —OC(CH₃)₂CF₃, —OC(CH₃)₂CHF₂, —O(halo-substituted cyclopropyl) and —O(halo-substituted cyclobutyl)), an unsubstituted acyl (for example, —C(=O)—$C_{1-4}$ alkyl), an unsubstituted C-amido (such as —C(=O)NH₂ and —C(=O)NH—$C_{1-4}$ alkyl), an unsubstituted sulfonyl (such as —S(=O)₂—$C_{1-4}$ alkyl), an unsubstituted amino, a mono-substituted amine (for example, an mono-alkyl substituted amine) and a di-substituted amine (such as a di-alkyl substituted amine). In some embodiments, $R^1$ can be substituted with one or more substituents independently selected from halogen (such as F, Cl and/or Br), cyano, an unsubstituted $C_{1-6}$ alkyl (such as methyl) and an unsubstituted $C_{2-6}$ alkynyl (for example, ethynyl).

The number of substituents present on a substituted $R^1$ group can vary. In some embodiments, $R^1$ is substituted with 1 substituent. In other embodiments, $R^1$ is substituted with 2 substituents. In still other embodiments, $R^1$ is substituted with 3 substituents.

Exemplary $R^1$ groups include, but are not limited to, the following:

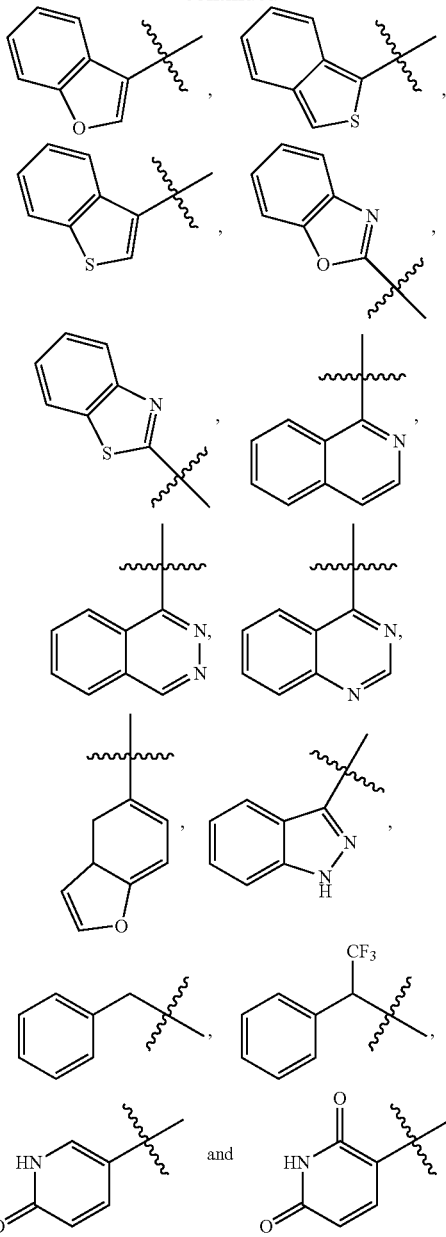

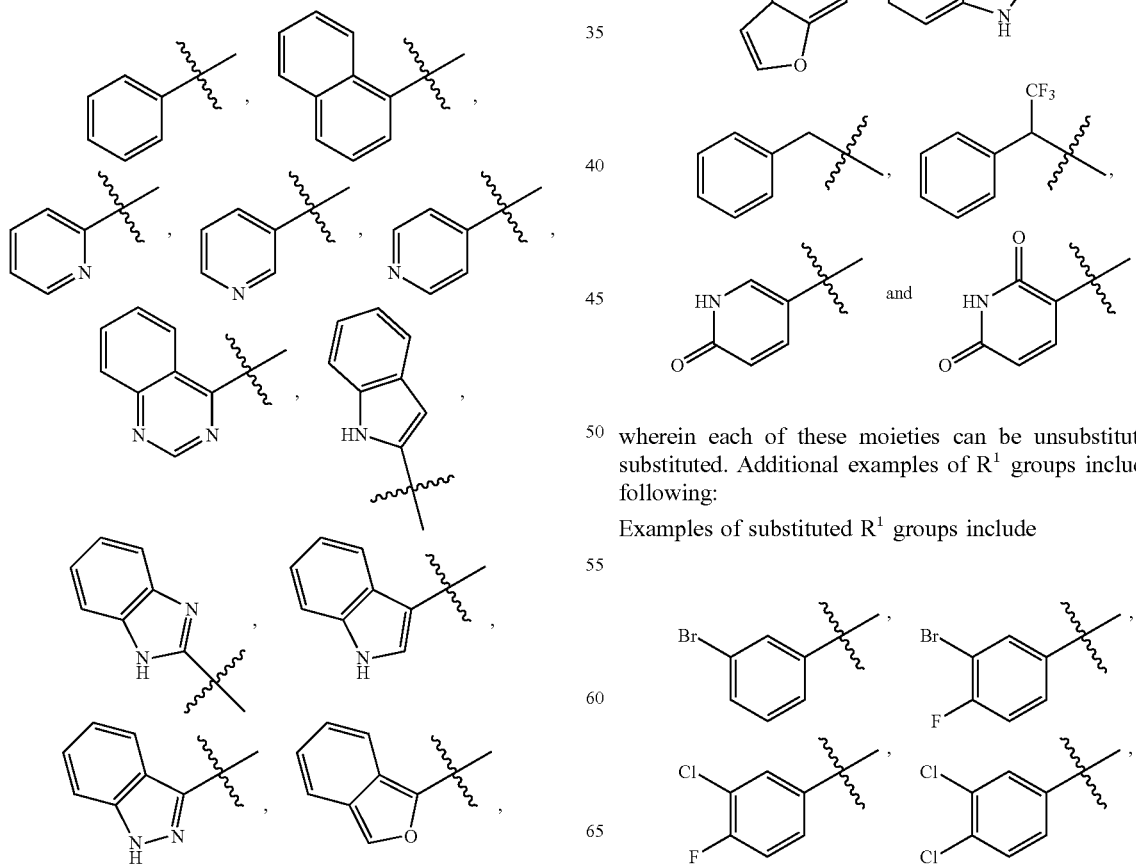

wherein each of these moieties can be unsubstituted or substituted. Additional examples of $R^1$ groups include the following:

Examples of substituted $R^1$ groups include

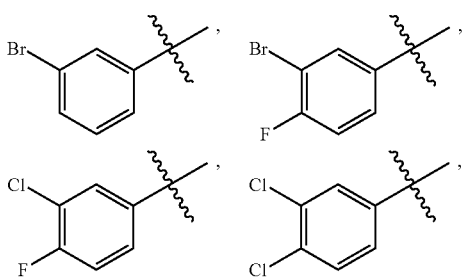

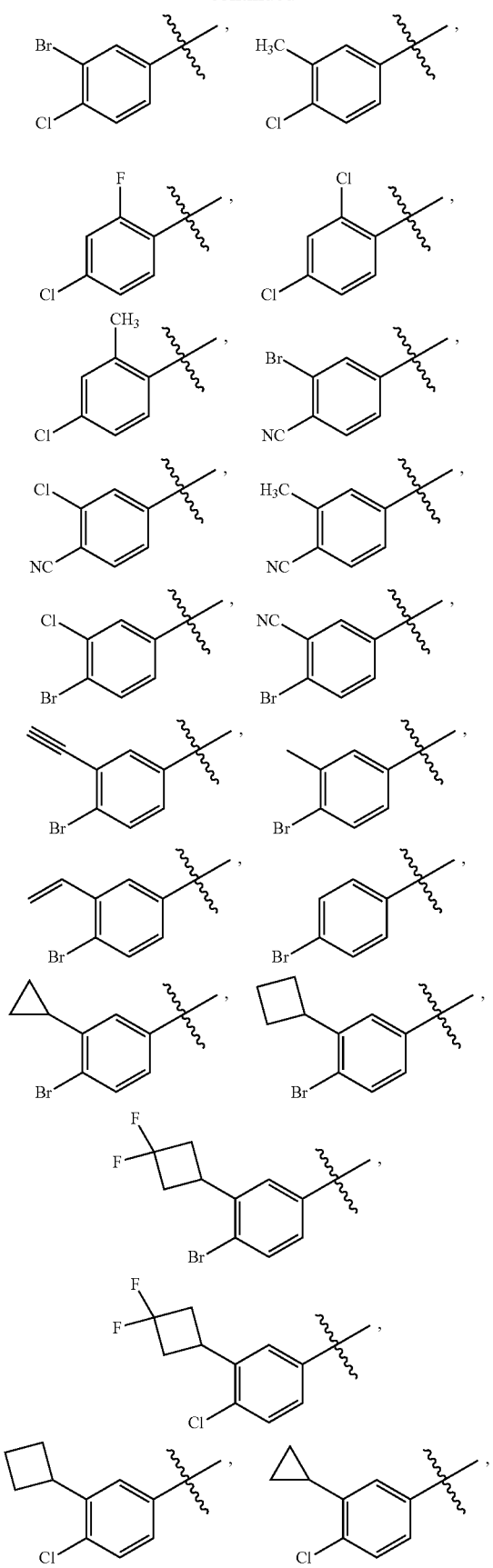
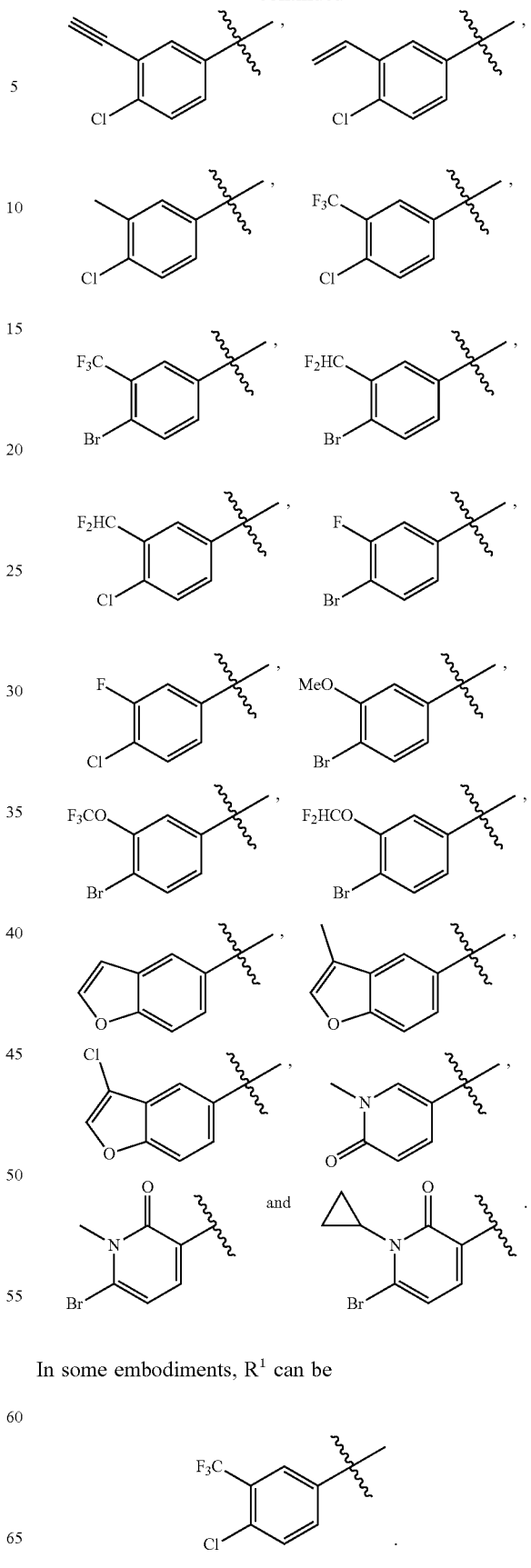
In some embodiments, R[1] can be

In other embodiments, $R^1$ can be

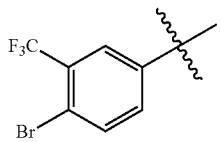

In addition to the groups described herein that can be attached to the ring structure of Formula (I), the piperidinyl ring can be further unsubstituted or substituted. In some embodiments, $R^2$ can be hydrogen. In other embodiments, $R^2$ can be an unsubstituted $C_{1-4}$ alkyl. For example, $R^2$ can be methyl, ethyl, n-propyl, iso-propyl, n-butyl, iso-butyl, sec-butyl and tert-butyl. In still other embodiments, $R^2$ can be an unsubstituted $C_{1-4}$ haloalkyl. Suitable unsubstituted $C_{1-4}$ haloalkyls are described herein, and include —$CHF_2$, —$CH_2F$, —$CF_3$, —$CH_2Cl$, —$CHCl_2$ and —$CCl_3$. In yet still other embodiments, $R^2$ can be an optionally substituted monocyclic $C_{3-6}$ cycloalkyl. Examples of monocyclic $C_{3-6}$ cycloalkyls include, but are not limited to, cyclopropyl, cyclobutyl, cyclopentyl and cyclohexyl, wherein each of the aforementioned can be unsubstituted or substituted. In some embodiments, $R^2$ can be an optionally substituted aryl (such as an optionally phenyl), an optionally substituted heteroaryl (such as an optionally substituted monocyclic heteroaryl) or an optionally substituted heterocyclyl (for example, an optionally substituted monocyclic heterocyclyl). The heteroaryl and heterocyclyl can include 3, 4, 5 or 6 ring(s) atoms. In other embodiments, $R^2$ can be an optionally substituted aryl($C_{1-4}$ alkyl), an optionally substituted heteroaryl($C_{1-4}$ alkyl) or an optionally substituted heterocyclyl ($C_{1-4}$ alkyl).

In some embodiments, $R^3$ can be hydrogen. In other embodiments, $R^3$ can be an unsubstituted $C_{1-4}$ alkyl. In still other embodiments, $R^3$ can be an unsubstituted $C_{1-4}$ haloalkyl. Exemplary unsubstituted $C_{1-4}$ alkyls and unsubstituted $C_{1-4}$ haloalkyls are described herein and include those described with respect to $R^2$. In yet still other embodiments, $R^3$ can be an optionally substituted monocyclic $C_{3-6}$ cycloalkyl, such as those described herein with respect to $R^2$. When $R^3$ is a monocyclic $C_{3-6}$ cycloalkyl, the $C_{3-6}$ cycloalkyl can be unsubstituted or substituted. In some embodiments, $R^3$ can be an optionally substituted aryl, an optionally substituted heteroaryl or an optionally substituted heterocyclyl. In some embodiments, $R^3$ can be an optionally substituted aryl($C_{1-4}$ alkyl), an optionally substituted heteroaryl($C_{1-4}$ alkyl) or an optionally substituted heterocyclyl($C_{1-4}$ alkyl). For example, $R^3$ can be an optionally substituted phenyl, an optionally substituted benzyl, an optionally substituted monocyclic heteroaryl (an optionally substituted 5- or 6-membered monocyclic heteroaryl) or an optionally substituted monocyclic heterocyclyl (an optionally substituted 5- or 6-membered monocyclic heterocyclyl).

In some embodiments, $R^4$ can be hydrogen. In other embodiments, $R^4$ can be an unsubstituted $C_{1-4}$ alkyl, such as those described herein. In still other embodiments, $R^4$ can be an unsubstituted $C_{1-4}$ haloalkyl, for example, —$CHF_2$, —$CH_2F$, —$CF_3$, —$CH_2Cl$, —$CHCl_2$ and —$CCl_3$. In yet still other embodiments, $R^4$ can be an optionally substituted aryl, an optionally substituted heteroaryl or an optionally substituted heterocyclyl. In some embodiments, $R^4$ can be an optionally substituted aryl($C_{1-4}$ alkyl), an optionally substituted heteroaryl($C_{1-4}$ alkyl) or an optionally substituted heterocyclyl($C_{1-4}$ alkyl). In other embodiments, $R^4$ can be an optionally substituted phenyl, an optionally substituted monocyclic heteroaryl or an optionally substituted monocyclic heterocyclyl.

In some embodiments, $R^5$ can be hydrogen. In other embodiments, $R^5$ can be an unsubstituted $C_{1-4}$ alkyl. In still other embodiments, $R^5$ can be an unsubstituted $C_{1-4}$ haloalkyl. For example, $R^5$ can be methyl, ethyl, n-propyl, iso-propyl, n-butyl, iso-butyl, sec-butyl, tert-butyl, —$CHF_2$, —$CH_2F$, —$CF_3$, —$CH_2Cl$, —$CHCl_2$ and —$CCl_3$. In yet still other embodiments, $R^5$ can be an optionally substituted aryl, an optionally substituted heteroaryl or an optionally substituted heterocyclyl. In some embodiments, $R^5$ can be an optionally substituted aryl($C_{1-4}$ alkyl), an optionally substituted heteroaryl($C_{1-4}$ alkyl) or an optionally substituted heterocyclyl($C_{1-4}$ alkyl). Exemplary $R^5$ groups include, but are not limited to, an optionally substituted phenyl, an optionally substituted benzyl, an optionally substituted monocyclic heteroaryl (an optionally substituted 5- or 6-membered monocyclic heteroaryl) or an optionally substituted monocyclic heterocyclyl (an optionally substituted 5- or 6-membered monocyclic heterocyclyl).

In some embodiments, $R^6$ can be hydrogen. In other embodiments, $R^6$ can be an unsubstituted $C_{1-4}$ alkyl. In still other embodiments, $R^6$ can be an unsubstituted $C_{1-4}$ haloalkyl. Suitable unsubstituted $C_{1-4}$ alkyls and unsubstituted $C_{1-4}$ haloalkyls include methyl, ethyl, n-propyl, iso-propyl, n-butyl, iso-butyl, sec-butyl, tert-butyl, —$CHF_2$, —$CH_2F$, —$CF_3$, —$CH_2Cl$, —$CHCl_2$ and —$CCl_3$.

In some embodiments, $R^7$ can be hydrogen. In other embodiments, $R^7$ can be an unsubstituted $C_{1-4}$ alkyl, such as methyl, ethyl, n-propyl, iso-propyl, n-butyl, iso-butyl, sec-butyl or tert-butyl. In still other embodiments, $R^7$ can be an unsubstituted $C_{1-4}$ haloalkyl, for example, —$CHF_2$, —$CH_2F$, —$CF_3$, —$CH_2Cl$, —$CHCl_2$ and —$CCl_3$.

In some embodiments, $R^2$, $R^3$, $R^4$, $R^5$, $R^6$ and $R^7$ can be each hydrogen. In other embodiments, at least one of $R^2$, $R^3$, $R^4$, $R^5$, $R^6$ and $R^7$ can be a non-hydrogen group, such as those described herein in the previous paragraphs. When at least one of $R^2$, $R^3$, $R^4$, $R^5$, $R^6$ and $R^7$ is a non-hydrogen group, at least one of $R^2$, $R^3$, $R^4$, $R^5$, $R^6$ and $R^7$ can be an unsubstituted $C_{1-4}$ alkyl (for example, methyl) or an optionally substituted monocyclic $C_{3-6}$ cycloalkyl (such as an unsubstituted or a substituted cyclopropyl). In some embodiments, $R^3$, $R^4$, $R^5$, $R^6$ and $R^7$ can be each hydrogen; and $R^2$ can be an unsubstituted $C_{1-4}$ alkyl (such as methyl). In other embodiments, $R^3$, $R^4$, $R^5$, $R^6$ and $R^7$ can be each hydrogen; and $R^2$ can be an optionally substituted monocyclic $C_{3-6}$ cycloalkyl (such as an unsubstituted or a substituted cyclopropyl). When at least one of $R^2$, $R^3$, $R^4$, $R^5$, $R^6$ and $R^7$ is a non-hydrogen group, a stereocenter may be formed. In some embodiments, the stereocenter that is formed can be in the (R)-configuration. In other embodiments, the stereocenter that is formed can be in the (S)-configuration.

As described herein, $R^8$ can be selected from a hydroxy-$C_{1-6}$ alkyl, an optionally substituted alkoxy, an optionally substituted monocyclic $C_{3-6}$ cycloalkyl, an optionally substituted phenyl, an optionally substituted monocyclic heteroaryl, an optionally substituted monocyclic heterocyclyl, an optionally substituted 6-17 member bicyclic heterocyclyl, an optionally substituted monocyclic $C_{3-6}$ cycloalkyl($C_{1-4}$ alkyl), an optionally substituted aryl($C_{1-4}$ alkyl), an optionally substituted monocyclic heteroaryl($C_{1-4}$ alkyl), an optionally substituted monocyclic heterocyclyl ($C_{1-4}$ alkyl), an optionally substituted 6-17 member bicyclic heterocyclyl ($C_{1-4}$ alkyl), an optionally substituted aryloxy($C_{1-4}$ alkyl), —$OR^{10}$, —$SR^{11}$, —C(=O)$NHR^{13}$ and —$NR^{14A}R^{14B}$, wherein the $C_{1-4}$ alkyl of the optionally substituted monocyclic $C_{3-6}$ cycloalkyl($C_{1-4}$ alkyl), the $C_{1-4}$ alkyl of the optionally substituted aryl($C_{1-4}$ alkyl), the optionally substituted monocyclic heteroaryl($C_{1-4}$ alkyl), the optionally substituted monocyclic heterocyclyl($C_{1-4}$ alkyl) and the $C_{1-4}$ alkyl of the optionally substituted 6-17 member bicyclic heterocyclyl($C_{1-4}$ alkyl) is optionally substituted with an unsubstituted $C_{1-3}$ alkyl or an unsubstituted $C_{3-4}$ monocyclic cycloalkyl.

When $R^8$ is substituted, one or more moieties independently selected from the following can be present: halogen (such as F, Cl or Br), hydroxy, an unsubstituted $C_{1-6}$ alkyl (such as methyl, ethyl, n-propyl, iso-propyl, n-butyl, sec-butyl, iso-butyl, tert-butyl, pentyl (straight-chained or branched) and hexyl (straight-chained or branched), an optionally substituted a $C_{2-5}$ alkenyl, an optionally substituted a $C_{2-5}$ alkynyl, an unsubstituted $C_{1-6}$ alkoxy, an unsubstituted $C_{1-6}$ haloalkyl (for example, —CHF$_2$, —CH$_2$F, —CF$_3$, —CH$_2$Cl, —CHCl$_2$ and —CCl$_3$), hydroxyalkyl (such as a $C_{1-6}$ hydroxyalkyl), alkoxyalkyl (such as a $C_{1-6}$ alkoxyalkyl), an optionally substituted monocyclic heteroaryl, amino, mono-substituted amine and di-substituted amine. Exemplary optionally substituted monocyclic heteroaryls that can be substituted on $R^8$ include 5- to 6-member monocyclic heteroaryls that includes 1 to 3 heteroatoms selected from O, S and N. For example, $R^8$ can be a 5- to 6-member monocyclic heteroaryls that includes 1 to 3 heteroatoms selected from O, S and N, which can be substituted with one or more moieties independently selected from halogen, amino, a mono-substituted amine (such as a mono-substituted-alkyl amine) and a di-substituted amine (such as a di-substituted-alkyl amine).

The $R^8$ substituent can be a cyclic moiety, such as a carbocyclyl, heteroaryl or heterocyclyl. In some embodiments, $R^8$ can be an unsubstituted monocyclic $C_{3-6}$ cycloalkyl. In other embodiments, $R^8$ can be a substituted monocyclic $C_{3-6}$ cycloalkyl. Examples of monocyclic $C_{3-6}$ cycloalkyls include cyclopropyl, cyclobutyl, cyclopentyl and cyclohexyl. In still other embodiments, $R^8$ can be an unsubstituted phenyl. In yet still other embodiments, $R^8$ can be a substituted phenyl.

As described herein, $R^8$ substituent can be a cyclic moiety that includes one or more heteroatoms, for example, one or more heteroatoms selected from N (nitrogen), O (oxygen) and S (sulfur). In some embodiments, $R^8$ can be an unsubstituted monocyclic heteroaryl. In other embodiments, $R^8$ can be a substituted monocyclic heteroaryl. In still other embodiments, $R^8$ can be an unsubstituted monocyclic heterocyclyl. In yet still other embodiments, $R^8$ can be a substituted monocyclic heterocyclyl. The number of ring atoms of heteroaryl and heterocyclyl of $R^8$ can vary. As example, a heteroaryl and/or a heterocyclyl for $R^8$ can include 5 to 6 ring atoms. In some embodiments, $R^8$ can be an unsubstituted 6-17 member bicyclic heterocyclyl. In other embodiments, $R^8$ can be a substituted 6-17 member bicyclic heterocyclyl. The 6-17 member bicyclic heterocyclyl can be a fused-bicyclic heterocyclyl where the two rings are joined by two adjacent ring atoms or a spiro-bicyclic heterocyclyl wherein the two rings are joined by one ring atom. In some embodiments, $R^8$ can be a monocyclic heteroaryl, a monocyclic heterocyclyl or a bicyclic heterocyclyl, wherein each includes 1, 2 or 3 heteroatoms independently selected from N (nitrogen), O (oxygen) or S (sulfur). Cyclic moieties that include one or more heteroatoms for $R^8$ include azetidine, oxetane, thietane, tetrahydrofuran, triazole, pyrrolidine, pyrazole, imidazole, thiazole, pyridine, pyrimidine, pyrazine, pyridazine, piperidine, piperazine, and indoline. In some embodiments, $R^8$ can be connected to the rest of Formula (I) via a nitrogen. For example, $R^8$ can be

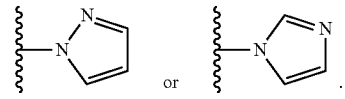

Alternatively, $R^8$ can be connected to the rest Formula (I) via a carbon (such as

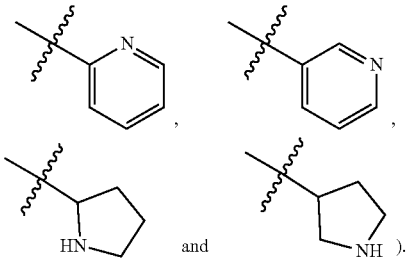

).

A variety of cyclic groups described herein for $R^8$ can be attached via a $C_{1-4}$ alkyl linker. In some embodiments, $R^8$ can be an optionally substituted monocyclic $C_{3-6}$ cycloalkyl ($C_{1-4}$ alkyl). Examples of suitable monocyclic $C_{3-6}$ cycloalkyls that can be attached via a $C_{1-4}$ alkyl linker are provided herein, and include cyclopropyl, cyclobutyl, cyclopentyl and cyclohexyl. In other embodiments, $R^8$ can be an optionally substituted aryl($C_{1-4}$ alkyl), for example, an unsubstituted benzyl or a substituted benzyl. In still other embodiments, $R^8$ can be an optionally substituted monocyclic heteroaryl ($C_{1-4}$ alkyl). In yet still other embodiments, $R^8$ can be an optionally substituted monocyclic heterocyclyl($C_{1-4}$ alkyl). In some embodiments, $R^8$ can be an optionally substituted 6-17 member bicyclic heterocyclyl($C_{1-4}$ alkyl). As example, an optionally substituted monocyclic heteroaryl and/or an optionally substituted monocyclic heterocyclyl for $R^8$ can include 4 to 6 ring atoms. The 6-17 member bicyclic heterocyclyl that can be connected via a $C_{1-4}$ alkyl linker can be a fused-bicyclic heterocyclyl where the two rings are joined by two adjacent ring atoms or a spiro-bicyclic heterocyclyl wherein the two rings are joined by one ring atom. In some embodiments, $R^8$ can be an optionally substituted aryloxy($C_{1-4}$ alkyl), such as an optionally substituted phenoxy($C_{1-4}$ alkyl). Examples of cyclic moieties that can be connected via an optionally substituted $C_{1-4}$ alkyl linker include those moieties described herein for $R^8$, such as azetidine, oxetane, thietane, pyrrolidine, pyrazole, imidazole, thiazole, pyridine, pyrimidine, pyrazine, pyridazine and indoline.

The $C_{1-4}$ alkyl linker can be unsubstituted or substituted. When the $C_{1-4}$ alkyl is unsubstituted, the $C_{1-4}$ alkyl can be —CH$_2$—, —CH$_2$CH$_2$—, —CH$_2$CH$_2$CH$_2$— or —CH$_2$CH$_2$CH$_2$CH$_2$—. When the $C_{1-4}$ alkyl linker is substituted, one or more hydrogens of the $C_{1-4}$ alkyl linker can be replaced with an unsubstituted $C_{1-3}$ alkyl or an unsubstituted $C_{3-4}$ monocyclic cycloalkyl. As described herein, individual hydrogens on a carbon of a $C_{1-4}$ alkyl linker can be replaced with a moiety described herein and/or two hydrogens on the same carbon can be replaced with a single cyclic moiety as described herein. In some embodiments, the $C_{1-4}$ alkyl linker of an optionally substituted monocyclic $C_{3-6}$ cycloalkyl($C_{1-4}$ alkyl), an optionally substituted aryl($C_{1-4}$ alkyl), an optionally substituted monocyclic heteroaryl($C_{1-4}$ alkyl), an optionally substituted monocyclic heterocyclyl ($C_{1-4}$ alkyl) and/or an optionally substituted 6-17 member bicyclic heterocyclyl($C_{1-4}$ alkyl) for $R^8$ can be —$CH_2$—, —$CH(CH_3)$—, —$CH_2CH_2$—, —$CH(CH_3)CH_2$—, —$CH_2CH_2CH_2$—, —$CH_2CH_2CH_2CH_2$—,

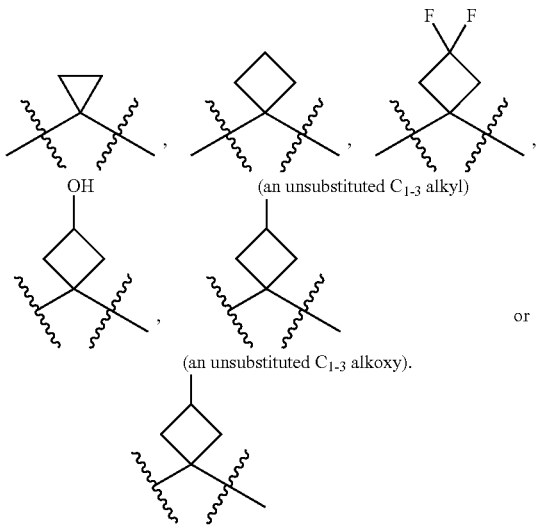

Examples of suitable $R^8$ groups that include a $C_{1-4}$ alkyl linker include, but are not limited to, the following: an optionally substituted monocyclic $C_{3-6}$ cycloalkyl($CH_2$)—, an optionally substituted monocyclic $C_{3-6}$ cycloalkyl ($CHCH_3$)—, an optionally substituted monocyclic heteroaryl($CH_2$)—, an optionally substituted monocyclic heteroaryl($CHCH_3$)—, an optionally substituted monocyclic heterocyclyl($CH_2$)—, an optionally substituted monocyclic heterocyclyl($CHCH_3$)—, an optionally substituted 6-17 member bicyclic heterocyclyl($CH_2$)—, an optionally substituted 6-17 member bicyclic heterocyclyl($CHCH_3$)—, an optionally substituted aryloxy($CH_2$)— and an optionally substituted aryloxy($CHCH_3$)—. In some embodiments, $R^8$ can be selected from an optionally substituted monocyclic $C_{3-6}$ cycloalkyl($C_{1-4}$ alkyl), an optionally substituted aryl ($C_{1-4}$ alkyl), an optionally substituted monocyclic heteroaryl ($C_{1-4}$ alkyl), an optionally substituted monocyclic heterocyclyl($C_{1-4}$ alkyl) and an optionally substituted aryloxy($C_{1-4}$ alkyl).

An $R^8$ substituent can be connected via an oxygen. For example, $R^8$ can be —$OR^{10}$, wherein $R^{10}$ can be selected from an unsubstituted $C_{1-6}$ alkyl, an optionally substituted monocyclic $C_{3-6}$ cycloalkyl, an optionally substituted aryl, an optionally substituted heteroaryl, an optionally substituted heterocyclyl, an optionally substituted monocyclic $C_{3-8}$ cycloalkyl($C_{1-4}$ alkyl), an optionally substituted aryl ($C_{1-4}$ alkyl), an optionally substituted heteroaryl($C_{1-4}$ alkyl) and an optionally substituted heterocyclyl($C_{1-4}$ alkyl). The $R^{10}$ substituent can be an acyclic group, such as an unsubstituted $C_{1-6}$ alkyl.

The $R^{10}$ substituent can also be a cyclic group directly attached or through an optionally substituted $C_{1-4}$ alkyl linker to the oxygen. For example, $R^{10}$ can be from the group consisting of an optionally substituted monocyclic $C_{3-6}$ cycloalkyl, an optionally substituted aryl, an optionally substituted heteroaryl, an optionally substituted heterocyclyl. Exemplary monocyclic $C_{3-6}$ cycloalkyls, aryls, heteroaryls and heterocyclyls are described throughout the present application, and include cyclopropyl, cyclobutyl, cyclopentyl, cyclohexyl, phenyl, naphthyl, monocyclic heteroaryls (such as 5- and 6-member monocyclic heteroaryls that include 1, 2 or 3 heteroatoms selected from O, S and N), bicyclic heteroaryls (such as 9- to 10-member heteroaryls that include 1-5 heteroatoms selected from O, S and N), monocyclic heterocyclyls (such as 4-, 5- and 6-member monocyclic heterocyclyls that include 1, 2 or 3 heteroatoms selected from O, S and N) and bicyclic heterocyclyls (such as 9- to 10-member heterocyclyls that include 1-5 heteroatoms selected from O, S and N), wherein each of the aforementioned groups can be unsubstituted or substituted. The two rings of a bicyclic heteroaryls and a bicyclic heterocyclyls for $R^{10}$ can be joined in a fused-fashion via two adjacent rings atoms or in a spiro-fashion via 1 ring atom. In some embodiments, $R^{10}$ can be azetidine, oxetane, thietane, pyrrolidine, pyrazole, imidazole, thiazole, pyridine, pyrimidine, pyrazine, pyridazine, quinoline, isoquinoline, indole or indoline, wherein each of the aforementioned moieties can be unsubstituted or substituted.

Each of the cyclic moieties described in the previous paragraph can also be connected via a $C_{1-4}$ alkyl linker to the oxygen of —$OR^{10}$. In some embodiments, $R^{10}$ can be an optionally substituted monocyclic $C_{3-8}$ cycloalkyl($C_{1-4}$ alkyl). In other embodiments, $R^{10}$ can be an optionally substituted aryl($C_{1-4}$ alkyl). In still other embodiments, $R^{10}$ can be an optionally substituted heteroaryl($C_{1-4}$ alkyl). In yet still other embodiments, $R^{10}$ can be an optionally substituted heterocyclyl($C_{1-4}$ alkyl). The $C_{1-4}$ alkyl linker for an optionally substituted monocyclic $C_{3-8}$ cycloalkyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl), can be unsubstituted or substituted with an unsubstituted $C_{1-3}$ alkyl, a monocyclic $C_{3-6}$ cycloalkyl optionally substituted with one or more substituents independently selected from halogen, hydroxy, an unsubstituted $C_{1-3}$ alkyl and unsubstituted $C_{1-3}$ alkoxy, or an optionally substituted 4-6 membered monocyclic heterocyclyl. When the $C_{1-4}$ alkyl linker of an optionally substituted monocyclic $C_{3-8}$ cycloalkyl($C_{1-4}$ alkyl), an optionally substituted aryl($C_{1-4}$ alkyl), an optionally substituted heterocyclyl($C_{1-4}$ alkyl) and an optionally substituted heterocyclyl ($C_{1-4}$ alkyl) for $R^{10}$ are substituted, individual hydrogens on a carbon of the $C_{1-4}$ alkyl linker can be replaced with a moiety described herein and/or two hydrogens on the same carbon can be replaced with a single cyclic moiety as described herein. Examples of $C_{1-4}$ alkyl linkers for a $R^{10}$ substituent described herein include, but are not limited to, —$CH_2$—, —$CH(CH_3)$—, —$CH_2CH_2$—, —$CH(CH_3)CH_2$—, —$CH_2CH_2CH_2$—, —$CH_2CH_2CH_2CH_2$—,

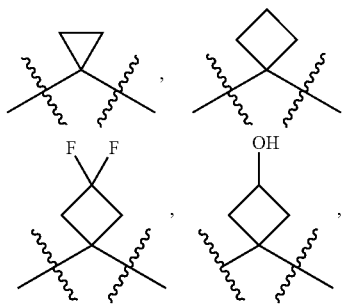

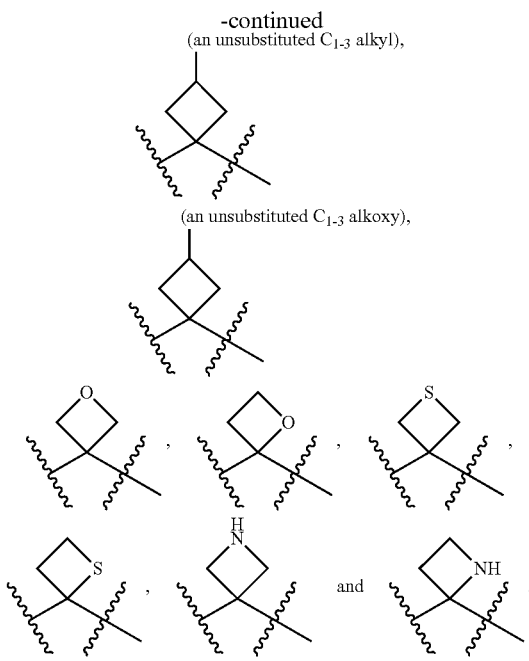

(an unsubstituted $C_{1-3}$ alkyl), (an unsubstituted $C_{1-3}$ alkoxy),

Various embodiments, when $R^8$ can be —$OR^{10}$, include the following and are described herein. In some embodiments, $R^8$ can be —$OR^{10}$, wherein $R^{10}$ can be selected from an optionally substituted monocyclic $C_{3-8}$ cycloalkyl($C_{1-4}$ alkyl), an optionally substituted aryl($C_{1-4}$ alkyl), an optionally substituted heterocyclyl($C_{1-4}$ alkyl) and an optionally substituted heterocyclyl($C_{1-4}$ alkyl), wherein the $C_{1-4}$ alkyl for each of the aforementioned substituents for $R^{10}$ can be unsubstituted or substituted with an unsubstituted $C_{1-3}$ alkyl or a monocyclic $C_{3-4}$ cycloalkyl. In other embodiments, $R^8$ can be —$OR^{10}$, wherein $R^{10}$ can be selected from an optionally substituted monocyclic $C_{3-8}$ cycloalkyl($C_{1-4}$ alkyl), an optionally substituted aryl($C_{1-4}$ alkyl), an optionally substituted heterocyclyl($C_{1-4}$ alkyl) and an optionally substituted heterocyclyl($C_{1-4}$ alkyl), wherein the $C_{1-4}$ alkyl for each of the aforementioned substituents for $R^{10}$ can be substituted with a monocyclic $C_{3-6}$ cycloalkyl optionally substituted with one or more substituents independently selected from halogen, hydroxy, an unsubstituted $C_{1-3}$ alkyl and unsubstituted $C_{1-3}$ alkoxy. In still other embodiments, $R^8$ can be —$OR^{10'}$ wherein $R^{10}$ can be selected from an optionally substituted monocyclic $C_{3-8}$ cycloalkyl($C_{1-4}$ alkyl), an optionally substituted aryl($C_{1-4}$ alkyl), an optionally substituted heterocyclyl($C_{1-4}$ alkyl) and an optionally substituted heterocyclyl($C_{1-4}$ alkyl), wherein the $C_{1-4}$ alkyl for each of the aforementioned substituents for $R^{10}$ can be substituted with a monocyclic $C_{3-6}$ cycloalkyl or an optionally substituted 4-6 membered monocyclic heterocyclyl.

An $R^8$ substituent can also be connected via a sulfur. In some embodiments, $R^8$ can be —$SR^{11}$, wherein $R^{11}$ can be selected from an unsubstituted $C_{1-6}$ alkyl, an optionally substituted monocyclic $C_{3-6}$ cycloalkyl, an optionally substituted aryl, an optionally substituted heteroaryl, an optionally substituted heterocyclyl, an optionally substituted monocyclic $C_{3-8}$ cycloalkyl($C_{1-4}$ alkyl), an optionally substituted aryl($C_{1-4}$ alkyl), an optionally substituted heteroaryl ($C_{1-4}$ alkyl) and an optionally substituted heterocyclyl($C_{1-4}$ alkyl). As with $R^{10}$, $R^{11}$ can be an acyclic or a cyclic moiety attached directly to the sulfur or through a $C_{1-4}$ linker to the sulfur. In some embodiments, $R^{11}$ can be an unsubstituted $C_{1-6}$ alkyl. In other embodiments, $R^{11}$ can be selected from an optionally substituted monocyclic $C_{3-6}$ cycloalkyl, an optionally substituted aryl, an optionally substituted heteroaryl, an optionally substituted heterocyclyl. In still other embodiments, $R^{11}$ can be selected from an optionally substituted monocyclic $C_{3-8}$ cycloalkyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl). Examples of optionally substituted monocyclic $C_{3-6}$ cycloalkyls, optionally substituted aryls, optionally substituted heteroaryls, optionally substituted heterocyclyls, optionally substituted monocyclic $C_{3-8}$ cycloalkyl($C_{1-4}$ alkyl), optionally substituted aryl($C_{1-4}$ alkyl), optionally substituted heteroaryl($C_{1-4}$ alkyl) and an optionally substituted heterocyclyl($C_{1-4}$ alkyl) are described herein with respect to $R^{10}$.

As described herein $R^8$ can be a C-amido, such as a C-amido having the general formula —$C(=O)NHR^{13}$. In some embodiments, $R^{13}$ can be an unsubstituted $C_{1-6}$ alkyl, such as methyl, ethyl, n-propyl, isopropyl, n-butyl, isobutyl, sec-butyl, tert-butyl, pentyl (straight-chained or branched) or hexyl (straight-chained or branched). In other embodiments, $R^3$ can be an optionally substituted aryl. For example, $R^{13}$ can be an optionally substituted phenyl or an optionally substituted naphthyl. In still other embodiments, $R^{13}$ can be an optionally substituted monocyclic $C_{3-6}$ cycloalkyl($C_{1-4}$ alkyl), an optionally substituted aryl($C_{1-4}$ alkyl), an optionally substituted heteroaryl($C_{1-4}$ alkyl) or an optionally substituted heterocyclyl($C_{1-4}$ alkyl). Exemplary monocyclic $C_{3-6}$ cycloalkyls, aryls, heteroaryls and heterocyclyls are described herein, and include cyclopropyl, cyclobutyl, cyclopentyl, cyclohexyl, phenyl, naphthyl, monocyclic heteroaryls (such as 5- and 6-member monocyclic heteroaryls that include 1, 2 or 3 heteroatoms selected from O, S and N), bicyclic heteroaryls (such as 9- to 10-member heteroaryls that include 1-5 heteroatoms selected from O, S and N), monocyclic heterocyclyls (such as 4-, 5- and 6-member monocyclic heterocyclyls that include 1, 2 or 3 heteroatoms selected from O, S and N) and bicyclic heterocyclyls (such as 9- to 10-member heterocyclyls that include 1-5 heteroatoms selected from O, S and N), wherein each of the aforementioned groups can be unsubstituted or substituted, including the $C_{1-4}$ alkyl linker.

An $R^8$ substituent can also be an amine, such as an amine having the general formula —$NR^{14A}R^{14B}$. In some embodiments, $R^{14A}$ can be an unsubstituted $C_{2-6}$ alkenyl. In other embodiments, $R^{14A}$ can be an optionally substituted 4- to 6-member monocyclic heterocyclyl. In still other embodiments, $R^{14A}$ can be hydrogen. In yet still other embodiments, $R^{14A}$ can be a monocyclic $C_{3-6}$ cycloalkyl optionally substituted with one or two halogens. Exemplary monocyclic $C_{3-6}$ cycloalkyls include cyclopropyl, cyclobutyl, cyclopentyl and cyclohexyl. As described herein, each of these monocyclic $C_{3-6}$ cycloalkyls can be optionally substituted with one or two halogens (such as one or two chloros or one or two fluoros). In some embodiments, $R^{14A}$ can be a monocyclic $C_{3-6}$ cycloalkyl($C_{1-4}$ alkyl) optionally substituted with one or two halogens. For example, $R^{14A}$ can be cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl-$CH_2CH_2$— or cyclohexyl-$CH_2CH_2$—. In other embodiments, $R^{14A}$ can be an unsubstituted $C_{1-6}$ alkyl, for example, methyl, ethyl, n-propyl, isopropyl, n-butyl, isobutyl, sec-butyl, tert-butyl, pentyl (straight-chained or branched) or hexyl (straight-chained or branched). In still other embodiments, $R^{14A}$ can be an optionally substituted 4- to 6-member monocyclic heterocyclyl. As an example, $R^{14A}$ can be an optionally substituted 4- to 6-member monocyclic heterocyclyl that includes 1-3 heteroatoms selected from O, S and N. In yet still other embodiments, $R^{14A}$ can be an optionally substituted monocyclic 4- to 6-membered heterocyclyl($C_{1-4}$ alkyl). A non-limiting list of 4- to 6-member monocyclic heterocyclyls that can be present for $R^{14A}$ or part of a monocyclic 4- to 6-membered heterocyclyl($C_{1-4}$ alkyl) include azetidine, oxetane and thietane, wherein each of the aforementioned can be unsubstituted or substituted.

For $R^{14B}$, $R^{14B}$ can be an unsubstituted $C_{1-6}$ alkyl, a cyclic moiety or a cyclic moiety attached via a $C_{1-4}$ alkyl linker. Exemplary unsubstituted $C_{1-6}$ alkyls for $R^{14B}$ are described herein. In some embodiments, $R^{14B}$ can be an optionally substituted aryl, such as an optionally substituted phenyl or an optionally substituted naphthyl. In other embodiments, $R^{14B}$ can be an optionally substituted monocyclic $C_{3-6}$ cycloalkyl($C_{1-4}$ alkyl). In still other embodiments, $R^{14B}$ can be an optionally substituted aryl($C_{1-4}$ alkyl), such as an unsubstituted benzyl or a substituted benzyl. In yet still other embodiments, $R^{14B}$ can be an optionally substituted heteroaryl($C_{1-4}$ alkyl). In some embodiments, $R^{14B}$ can be an optionally substituted heterocyclyl($C_{1-4}$ alkyl). In some embodiments, $R^{14B}$ can be an unsubstituted benzyl.

Examples of $C_{3-6}$ cycloalkyls that can be attached via a $C_{1-4}$ alkyl include cyclopropyl, cyclobutyl, cyclopentyl and cyclohexyl. An example of a heteroaryl that can be attached via $C_{1-4}$ alkyl linker is a 5- or 6-member monocyclic heteroaryl that includes 1-3 heteroatoms selected from O, S and N. The heterocyclyl that can be attached via a $C_{1-4}$ alkyl linker for $R^{14B}$ can be monocyclic or bicyclic. Another example of a heteroaryl that can be attached via $C_{1-4}$ alkyl linker is a 9- to 10-member bicyclic heteroaryl that includes 1-5 heteroatoms selected from N, O and S. When $R^{14B}$ can be an optionally substituted heterocyclyl($C_{1-4}$ alkyl), in some embodiments, $R^{14B}$ can be an optionally substituted monocyclic 5- to 6-member heterocyclyl or an optionally substituted bicyclic 9- to 10-member heterocyclyl, wherein the heterocyclyl can include 1 or more heteroatoms selected from O, S and N. The bicyclic heteroaryls and bicyclic heterocyclyls for $R^{14B}$ can be fused wherein the rings are connected via two adjacent ring atoms or spiro-cyclic wherein the rings are connected via 1 ring atom.

As described herein, the $C_{1-4}$ alkyl of the optionally substituted monocyclic $C_{3-6}$ cycloalkyl($C_{1-4}$ alkyl), the optionally substituted aryl($C_{1-4}$ alkyl), the optionally substituted heteroaryl($C_{1-4}$ alkyl) and the optionally substituted heterocyclyl($C_{1-4}$ alkyl) for $R^{14B}$ can be optionally substituted with an unsubstituted $C_{1-3}$ alkyl (for example, methyl, ethyl, n-propyl and isopropyl) or an unsubstituted $C_{3-4}$ monocyclic cycloalkyl (such as cyclopropyl and cyclobutyl). Further, the monocyclic $C_{3-6}$ cycloalkyl of a monocyclic $C_{3-6}$ cycloalkyl ($C_{1-4}$ alkyl), the aryl of an aryl($C_{1-4}$ alkyl), the heteroaryl of a heteroaryl($C_{1-4}$ alkyl) and the heterocyclyl of a heterocyclyl($C_{1-4}$ alkyl) can be unsubstituted or substituted. For example, the monocyclic $C_{3-6}$ cycloalkyl of a monocyclic $C_{3-6}$ cycloalkyl ($C_{1-4}$ alkyl), the aryl of an aryl($C_{1-4}$ alkyl), the heteroaryl of a heteroaryl ($C_{1-4}$ alkyl) and the heterocyclyl of a heterocyclyl($C_{1-4}$ alkyl) can be substituted with one or more moieties selected from halogen, an unsubstituted a $C_{2-5}$ alkenyl, a substituted a $C_{2-5}$ alkenyl, an unsubstituted a $C_{2-5}$ alkynyl, a substituted a $C_{2-5}$ alkynyl, an unsubstituted monocyclic heteroaryl (for example, a 5- to 6-member monocyclic heteroaryl containing 1-3 heteroatoms selected from O, S and N) and a substituted monocyclic heteroaryl (for example, a 5- to 6-member monocyclic heteroaryl containing 1-3 heteroatoms selected from O, S and N).

As provided herein, the phenyl and the monocyclic heteroaryl of $R^8$, the monocyclic 4- to 6-membered heterocyclyl($C_{1-4}$ alkyl) of $R^{14A}$, and the aryl and the aryl($C_{1-4}$ alkyl) of $R^{14B}$ can be substituted. In some embodiments, each of the aforementioned substituents for $R^8$, $R^{14A}$ and $R^{14B}$ can be substituted 1, 2 or 3 times from a moiety independently selected from halogen (for example, F or Cl), an unsubstituted $C_{1-4}$ alkyl (such as methyl, ethyl, n-propyl, iso-propyl, n-butyl, iso-butyl, sec-butyl and tert-butyl), an unsubstituted $C_{3-6}$ cycloalkyl (for example, cyclopropyl, cyclobutyl, cyclopentyl and cyclohexyl), a monocyclic 5- to 6-membered heteroaryl (such as a monocyclic 5- to 6-membered heteroaryl containing 1 or 2 heteroatoms selected from nitrogen (N), oxygen (O) and sulfur (S)) and C-carboxy (for example, —C(=O)—O— (an unsubstituted $C_{1-4}$ alkyl).

In some embodiments, $R^8$ can be —NR$^{14A}$R$^{14B}$, $R^{14A}$ can be an unsubstituted $C_{2-6}$ alkenyl, a monocyclic $C_{3-6}$ cycloalkyl optionally substituted with one or two halogens, or an optionally substituted 4-6 member monocyclic heterocyclyl; and $R^{14B}$ can be selected from an optionally substituted aryl and an optionally substituted heteroaryl($C_{1-4}$ alkyl), such as those described herein. In some embodiments, $R^8$ can be —NR$^{14A}$R$^{14B}$; $R^{14A}$ can be hydrogen; and $R^{14B}$ can be selected from an unsubstituted aryl($C_{1-4}$ alkyl) or a substituted aryl($C_{1-4}$ alkyl), such as an unsubstituted benzyl or a substituted benzyl. In some embodiments, $R^8$ can be —NR$^{14A}$R$^{14B}$; $R^{14A}$ can be hydrogen; and $R^{14B}$ can be selected from a substituted aryl($C_{1-4}$ alkyl), such as a substituted benzyl, wherein the aryl($C_{1-4}$ alkyl) is substituted with one or more moieties selected from halogen, an unsubstituted a $C_{2-5}$ alkenyl, a substituted a $C_{2-5}$ alkenyl, an unsubstituted a $C_{2-5}$ alkynyl and a substituted a $C_{2-5}$ alkynyl and an optionally substituted monocyclic heteroaryl (such as those described herein). In some embodiments, $R^8$ can be —NR$^{14A}$R$^{14B}$; $R^{14A}$ can be hydrogen or an unsubstituted $C_{1-6}$ alkyl; $R^{4B}$ can be selected from an unsubstituted $C_{1-6}$ alkyl, an optionally substituted aryl and an optionally substituted monocyclic $C_{3-6}$ cycloalkyl($C_{1-4}$ alkyl); and $R^1$ can be substituted with an unsubstituted $C_{2-4}$ alkenyl and/or an unsubstituted $C_{2-4}$ alkynyl (for example, $R^1$ can be

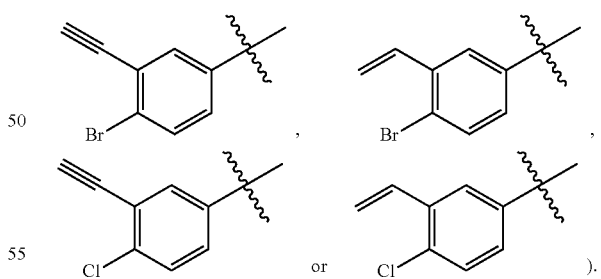

In some embodiments, $R^8$ can be —NR$^{14A}$R$^{14B}$ an optionally substituted monocyclic heterocyclyl or an optionally substituted 6-17 member bicyclic heterocyclyl; $R^{14A}$ can be hydrogen or an unsubstituted $C_{1-6}$ alkyl; $R^{14B}$ can be selected from an unsubstituted $C_{1-6}$ alkyl, an optionally substituted aryl and an optionally substituted monocyclic $C_{3-6}$ cycloalkyl($C_{1-4}$ alkyl); and $R^9$ can be a substituted phenyl, a substituted monocyclic heteroaryl or a substituted fused-bicyclic heteroaryl substituted with an optionally substituted monocyclic heterocyclyl.

As provided herein, $R^9$ can be a cyclic moiety that can be substituted. For example, in some embodiments, $R^9$ can be a substituted phenyl. $R^9$ can also be a heteroaryl (monocyclic or fused-bicyclic heteroaryl). The heteroaryl can have one or more heteroatoms present. Exemplary heteroatoms include, but are not limited to, N (nitrogen), O (oxygen) and S (sulfur). The size of the heteroaryl can vary. In some embodiments, $R^9$ can be a substituted monocyclic heteroaryl. The monocyclic heteroaryl can be a 5- or 6-member heteroaryl. In other embodiments, $R^9$ can be a substituted fused-bicyclic heteroaryl. The number of ring atoms of the fused-bicyclic heteroaryl can be 9 or 10 such that $R^9$ can be a substituted fused-bicyclic 9- or 10-member heteroaryl. Examples of suitable heteroaryls for $R^9$ include pyrazole, imidazole, pyridine, pyrimidine, pyrazine, pyridazine and indazole. In some embodiments, $R^9$ can be selected from: N

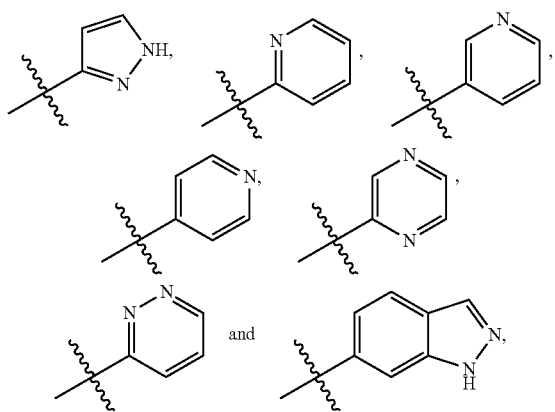

wherein each of the aforementioned can be unsubstituted or substituted as described herein.

As provided herein, $R^9$ can be substituted. Exemplary substituent(s) that can be present on $R^9$ include halogen (such as F, Cl or Br), an unsubstituted $C_{1-4}$ alkyl, an unsubstituted $C_{1-4}$ haloalkyl, an unsubstituted $C_{1-4}$ alkoxy, an optionally substituted monocyclic heteroaryl, an optionally substituted monocyclic heterocyclyl, amino, a mono-substituted amine, a di-substituted amine and —C(=O)NHR$^{15}$. Examples of unsubstituted $C_{1-4}$ alkyls and an unsubstituted $C_{1-4}$ alkoxys include the following: methyl, ethyl, n-propyl, isopropyl, n-butyl, sec-butyl, iso-butyl, tert-butyl, methoxy, ethoxy, n-propoxy, isopropoxy, n-butoxy, sec-butoxy, iso-butoxy and tert-butoxy. Exemplary unsubstituted $C_{1-4}$ haloalkyls include —CHF$_2$, —CH$_2$F, —CF$_3$, —CH$_2$Cl, —CHCl$_2$ and —CCl$_3$.

An $R^9$ group described herein, can be substituted with an unsubstituted or a substituted monocyclic heteroaryl, such as a 5- or 6-membered monocyclic heteroaryl that includes one or more heteroatoms selected from O (oxygen), S (sulfur) and N (nitrogen). Suitable monocyclic heteroaryls that can be present on $R^9$ are described herein, and include pyrazole, imidazole, pyridine, pyrimidine, pyrazine, pyridazine, pyridazine and pyridazine. In some embodiments, an unsubstituted or a substituted heterocyclyl (such as a 5- or 6-member heterocyclyl) can be substituted on an $R^9$ group described herein. The heteroatoms present in an unsubstituted or substituted heterocyclyl that can be substituted on an $R^9$ group described herein can vary, and include O (oxygen), S (sulfur) and N (nitrogen). Exemplary unsubstituted or a substituted heterocyclyls that can be present on an $R^9$ group described herein include morpholine, piperidine, piperazine, pyrrolidine, azetidine and oxetane. The substituted heteroaryls and/or substituted heterocyclyls that can be substituted on an $R^9$ group described herein can be substituted with one or more moieties such as those described herein for "optionally substituted." In some embodiments, the substituted heteroaryls and/or substituted heterocyclyls that can be substituted on an $R^9$ group described herein can be substituted with halogen, an unsubstituted $C_{1-4}$ alkyl, an unsubstituted $C_{1-4}$ haloalkyl and/or an unsubstituted $C_{1-4}$ alkoxy. Suitable halogens, unsubstituted $C_{1-4}$ alkyls, unsubstituted $C_{1-4}$ haloalkyls and/or unsubstituted $C_{1-4}$ alkoxys are described herein, such as those described in this paragraph.

As provided herein, amino, a mono-substituted amine, a di-substituted amine and/or —C(=O)NHR$^{15}$ can be substituted on an $R^9$ group described herein. The mono-substituted amine can have the general formula —NH (an unsubstituted $C_{1-4}$ alkyl), and the di-substituted amine can have the general formula —N(an unsubstituted $C_{1-4}$ alkyl)$_2$. In some embodiment, an $R^9$ group described herein can be substituted with —C(=O)NHR$^{15}$, wherein R$^{15}$ can be hydrogen, an unsubstituted $C_{1-6}$ alkyl (such as methyl, ethyl, n-propyl, isopropyl, n-butyl, sec-butyl, iso-butyl, tert-butyl, pentyl (straight-chained or branched) and hexyl (straight-chained or branched), an optionally substituted $C_{2-6}$ alkenyl (for example, ethenyl and propenyl), an optionally substituted $C_{1-6}$ alkynyl (such as ethynyl and propynyl) or an optionally substituted monocyclic $C_{3-6}$ cycloalkyl. The optionally substituted monocyclic $C_{3-6}$ cycloalkyl for R$^{15}$ can be an unsubstituted monocyclic $C_{3-6}$ cycloalkyl, a halo-substituted monocyclic $C_{3-6}$ cycloalkyl or an unsubstituted $C_{1-4}$ alkyl-substituted monocyclic $C_{3-6}$ cycloalkyl.

In some embodiments, a compound of Formula (I), or a pharmaceutically acceptable salt thereof, can be where n can be 0 or 1; $Z^1$ can be —C(=O)—, —NH—C(=O)—, —O—C(=O)—, —OCH$_2$C(=O)—, —CH=CHC(=O)— or —CH(CF$_3$)—; $R^1$ can be selected from an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); $R^2$ and $R^3$ can be independently selected from hydrogen, an unsubstituted $C_{1-4}$ alkyl, an unsubstituted $C_{1-4}$ haloalkyl, an optionally substituted monocyclic $C_{3-6}$ cycloalkyl, an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); $R^4$ and $R^5$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); $R^6$ and $R^7$ can be independently selected from hydrogen, an unsubstituted $C_{1-4}$ alkyl and an unsubstituted $C_{1-4}$ haloalkyl; $R^8$ can be selected from a hydroxy-$C_{1-6}$ alkyl, an optionally substituted alkoxy, an optionally substituted monocyclic $C_{3-6}$ cycloalkyl, an optionally substituted phenyl, an optionally substituted monocyclic heteroaryl, an optionally substituted monocyclic heterocyclyl, an optionally substituted 6-17 member bicyclic heterocyclyl, an optionally substituted monocyclic $C_{3-6}$ cycloalkyl(C$_{1-4}$ alkyl), an optionally substituted aryl(C$_{1-4}$ alkyl), an optionally substituted monocyclic heteroaryl(C$_{1-4}$ alkyl), an optionally substituted monocyclic heterocyclyl (C$_{1-4}$ alkyl), an optionally substituted 6-17 member bicyclic heterocyclyl(C$_{1-4}$ alkyl), an optionally substituted aryloxy(C$_{1-4}$ alkyl), —OR$^{10}$, —SR$^{11}$, —C(═O) NHR$^{13}$ and —NR$^{14A}$R$^{14B}$, wherein the C$_{1-4}$ alkyl of the optionally substituted monocyclic C$_{3-6}$ cycloalkyl(C$_{1-4}$ alkyl), the C$_{1-4}$ alkyl of the optionally substituted aryl(C$_{1-4}$ alkyl), the optionally substituted monocyclic heteroaryl(C$_{1-4}$ alkyl), the optionally substituted monocyclic heterocyclyl (C$_{1-4}$ alkyl) and the C$_{1-4}$ alkyl of the optionally substituted 6-17 member bicyclic heterocyclyl(C$_{1-4}$ alkyl) can be optionally substituted with an unsubstituted C$_{1-3}$ alkyl or an unsubstituted C$_{3-4}$ monocyclic cycloalkyl; R$^9$ can be a substituted phenyl, a substituted monocyclic heteroaryl or a substituted fused-bicyclic heteroaryl, wherein the substituted phenyl, the substituted monocyclic heteroaryl or the substituted fused-bicyclic heteroaryl can be substituted with one or more substituents selected from halogen, an unsubstituted C$_{1-4}$ alkyl, an unsubstituted C$_{1-4}$ haloalkyl, an unsubstituted C$_{1-4}$ alkoxy, an optionally substituted monocyclic heteroaryl, an optionally substituted monocyclic heterocyclyl, amino, a mono-substituted amine, a di-substituted amine and —C(═O)NHR$^{15}$; R$^{10}$ and R$^{11}$ can be independently selected from an unsubstituted C$_{1-6}$ alkyl, an optionally substituted monocyclic C$_{3-6}$ cycloalkyl, an optionally substituted aryl, an optionally substituted heteroaryl, an optionally substituted heterocyclyl, an optionally substituted monocyclic C$_{3-8}$ cycloalkyl(C$_{1-4}$ alkyl), an optionally substituted aryl(C$_{1-4}$ alkyl), an optionally substituted heteroaryl (C$_{1-4}$ alkyl) and an optionally substituted heterocyclyl(C$_{1-4}$ alkyl), wherein the C$_{1-4}$ alkyl of the optionally substituted monocyclic C$_{3-8}$ cycloalkyl(C$_{1-4}$ alkyl), the optionally substituted aryl(C$_{1-4}$ alkyl), the optionally substituted heteroaryl (C$_{1-4}$ alkyl) and the optionally substituted heterocyclyl(C$_{1-4}$ alkyl) can be optionally substituted with an unsubstituted C$_{1-3}$ alkyl, a monocyclic C$_{3-6}$ cycloalkyl optionally substituted with one or more substituents selected from halogen, hydroxy, an unsubstituted C$_{1-3}$ alkyl, unsubstituted C$_{1-3}$ alkoxy, amino, C$_{1-4}$ alkylamino and an optionally substituted 4-6 membered monocyclic heterocyclyl; R$^{13}$ can be selected from an unsubstituted C$_{1-6}$ alkyl, an optionally substituted aryl, an optionally substituted monocyclic C$_{3-6}$ cycloalkyl (C$_{1-4}$ alkyl), an optionally substituted aryl(C$_{1-4}$ alkyl), an optionally substituted heteroaryl(C$_{1-4}$ alkyl) or an optionally substituted heterocyclyl(C$_{1-4}$ alkyl), wherein the C$_{1-4}$ alkyl of the optionally substituted monocyclic C$_{3-6}$ cycloalkyl (C$_{1-4}$ alkyl), the optionally substituted aryl(C$_{1-4}$ alkyl), the optionally substituted heteroaryl(C$_{1-4}$ alkyl) and the optionally substituted heterocyclyl(C$_{1-4}$ alkyl) can be optionally substituted with an unsubstituted C$_{1-3}$ alkyl or an unsubstituted C$_{3-4}$ monocyclic cycloalkyl; R$^{14A}$ can be hydrogen, an unsubstituted C$_{1-6}$ alkyl, an unsubstituted C$_{2-6}$ alkenyl, a monocyclic C$_{3-6}$ cycloalkyl optionally substituted with one or two halogens, an optionally substituted 5-6 member monocyclic heteroaryl or an optionally substituted 4-6 member monocyclic heterocyclyl; R$^{14B}$ can be selected from an unsubstituted C$_{1-6}$ alkyl, an optionally substituted aryl, an optionally substituted monocyclic C$_{3-6}$ cycloalkyl(C$_{1-4}$ alkyl), an optionally substituted aryl(C$_{1-4}$ alkyl), an optionally substituted heteroaryl(C$_{1-4}$ alkyl) and an optionally substituted heterocyclyl(C$_{1-4}$ alkyl), wherein the C$_{1-4}$ alkyl of the optionally substituted monocyclic C$_{3-6}$ cycloalkyl (C$_{1-4}$ alkyl), the optionally substituted aryl(C$_{1-4}$ alkyl), the optionally substituted heteroaryl(C$_{1-4}$ alkyl) and the optionally substituted heterocyclyl(C$_{1-4}$ alkyl) can be optionally substituted with an unsubstituted C$_{1-3}$ alkyl or an unsubstituted C$_{3-4}$ monocyclic cycloalkyl; and R$^{15}$ can be hydrogen, an unsubstituted C$_{1-6}$ alkyl, an optionally substituted C$_{2-6}$ alkenyl, an optionally substituted C$_{1-6}$ alkynyl or an optionally substituted monocyclic C$_{3-6}$ cycloalkyl.

In some embodiments, a compound of Formula (I), or a pharmaceutically acceptable salt thereof, can be where n can be 1; Z$^1$ can be —C(═O)—; R$^1$ can be selected from

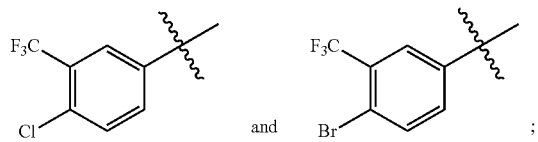 [SMILES: *c1ccc(Cl)c(C(F)(F)F)c1 ; *c1ccc(Br)c(C(F)(F)F)c1]

R$^2$ and R$^3$ can be independently selected from hydrogen and an unsubstituted C$_{1-4}$ alkyl; R$^4$, R$^5$, R$^6$ and R$^7$ can be each hydrogen; R$^8$ can be selected from an optionally substituted phenyl, an optionally substituted monocyclic heteroaryl, an optionally substituted monocyclic heterocyclyl and —NR$^{14A}$R$^{14B}$; R$^9$ can be a substituted phenyl, a substituted monocyclic heteroaryl or a substituted fused-bicyclic heteroaryl, wherein the substituted phenyl, the substituted monocyclic heteroaryl or the substituted fused-bicyclic heteroaryl can be substituted with one or more substituents selected from halogen, an unsubstituted C$_{1-4}$ alkyl, an unsubstituted C$_{1-4}$ haloalkyl, an unsubstituted C$_{1-4}$ alkoxy, an optionally substituted monocyclic heteroaryl, an optionally substituted monocyclic heterocyclyl, amino, a mono-substituted amine, a di-substituted amine and —C(═O) NHR$^{15}$; R$^{14A}$ can be hydrogen a monocyclic C$_{3-6}$ cycloalkyl optionally substituted with one or two halogens, a monocyclic C$_{3-6}$ cycloalkyl(C$_{1-4}$ alkyl) optionally substituted with one or two halogens, an optionally substituted monocyclic 4- to 6-membered heterocyclyl or an optionally substituted monocyclic 4- to 6-membered heterocyclyl(C$_{1-4}$ alkyl); R$^{14B}$ can be selected from an optionally substituted aryl and an optionally substituted aryl(C$_{1-4}$ alkyl); and R$^{15}$ can be hydrogen, an unsubstituted C$_{1-6}$ alkyl, an optionally substituted C$_{2-6}$ alkenyl, an optionally substituted C$_{1-6}$ alkynyl or an optionally substituted C$_{3-6}$ monocyclic cycloalkyl.

Examples of compounds of Formula (I), including pharmaceutically acceptable salts thereof, include:

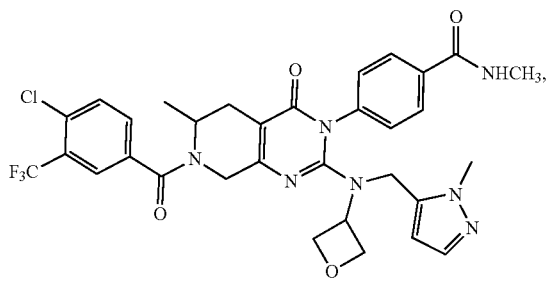

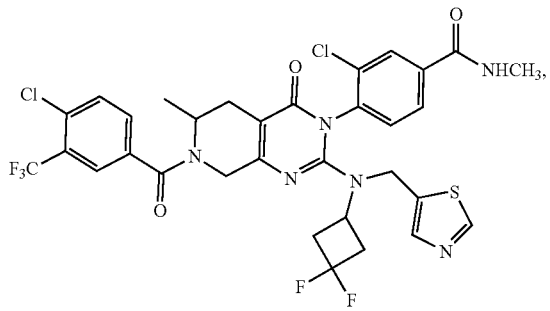

33
-continued
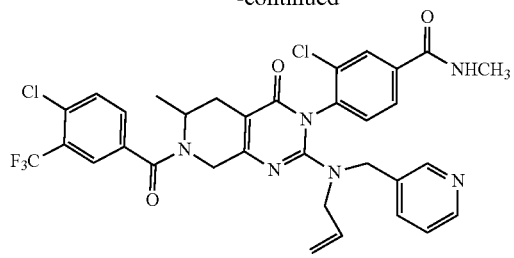
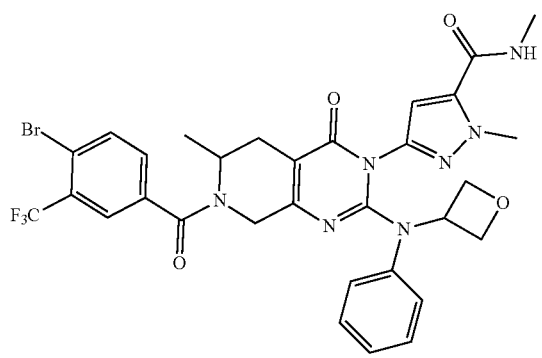
or a pharmaceutically acceptable salt of any of the foregoing.
Additional examples of compounds of Formula (I), including pharmaceutically acceptable salts thereof, include the following:
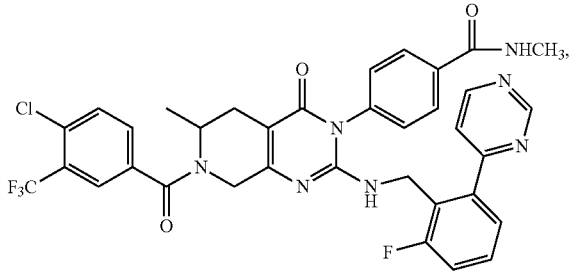
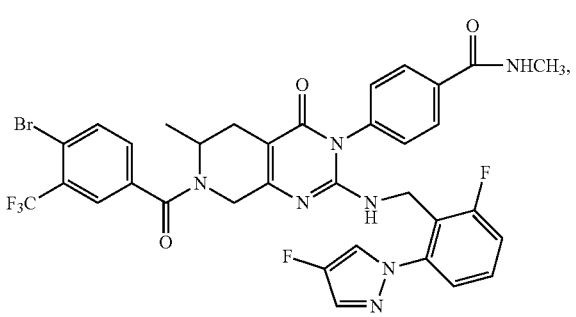
34
-continued
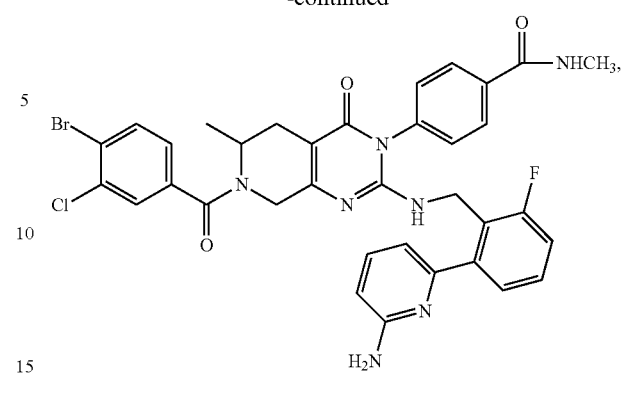
and
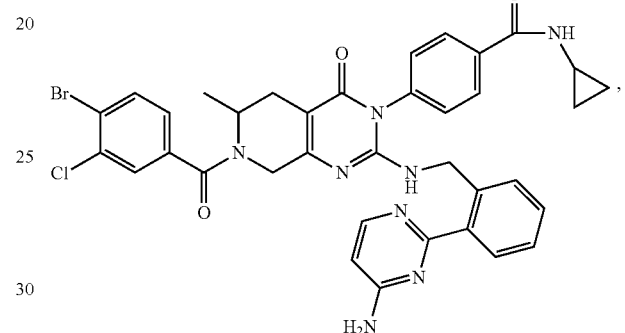
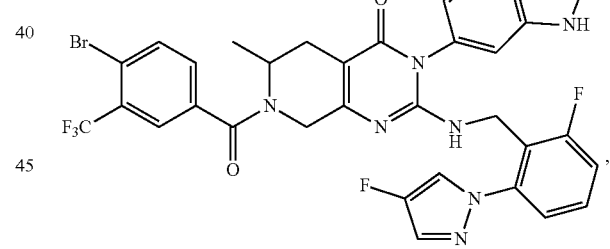
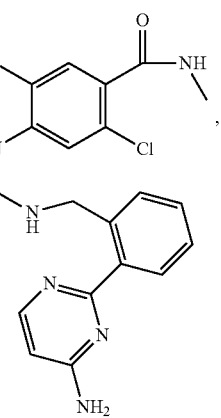

35
-continued
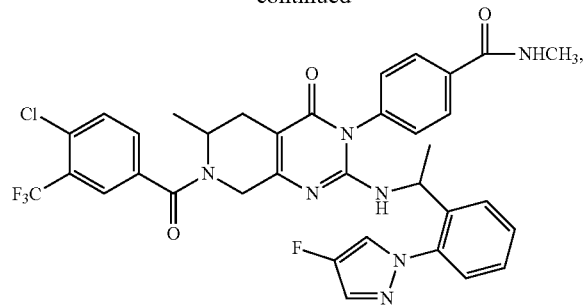
36
-continued
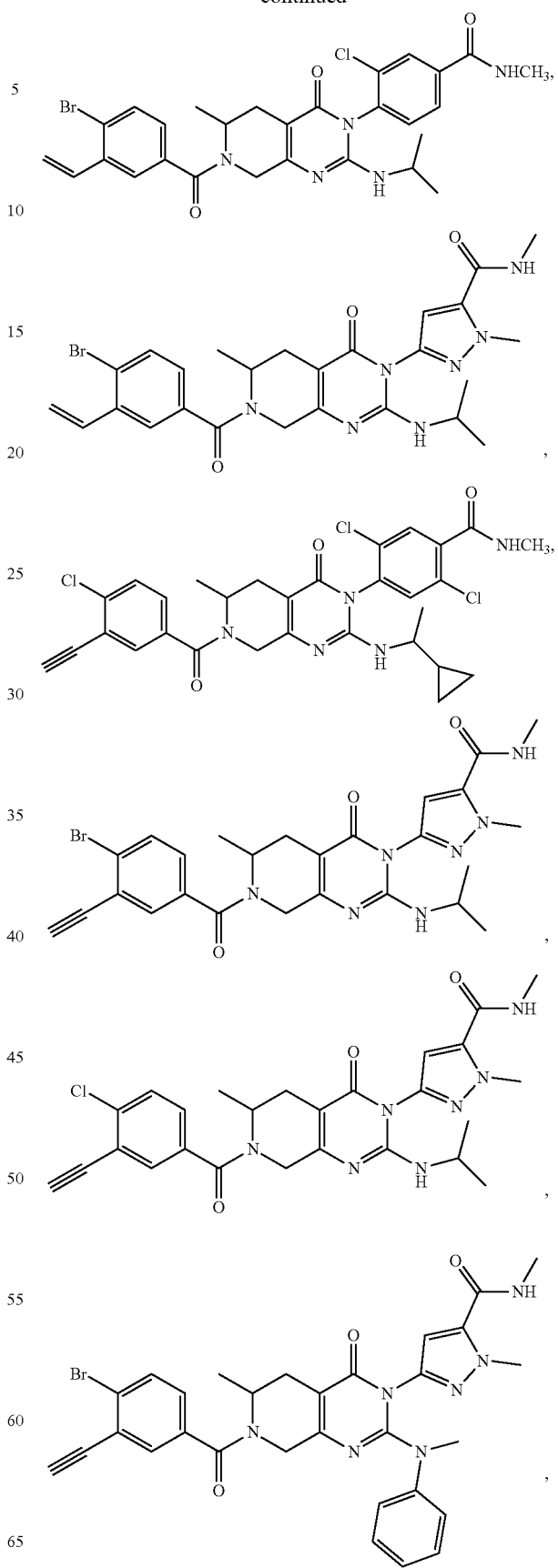

-continued
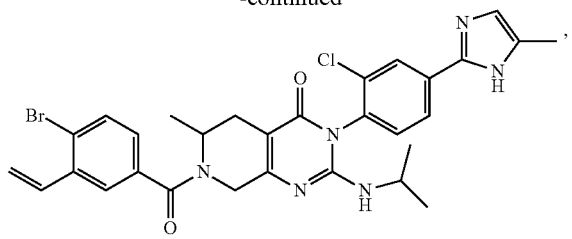
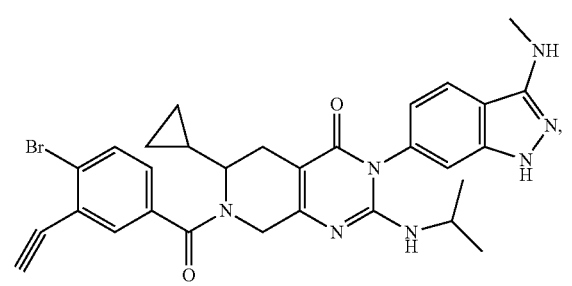
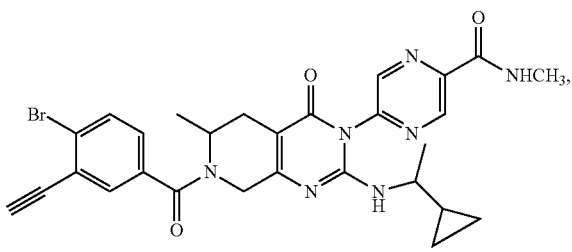
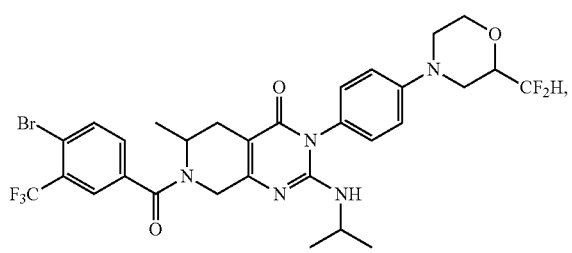
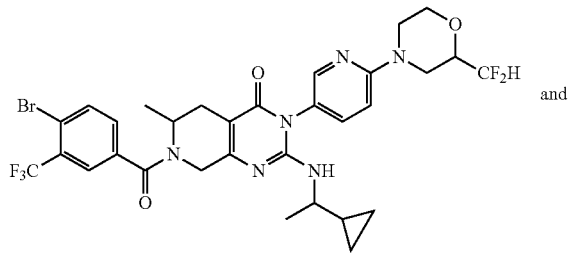
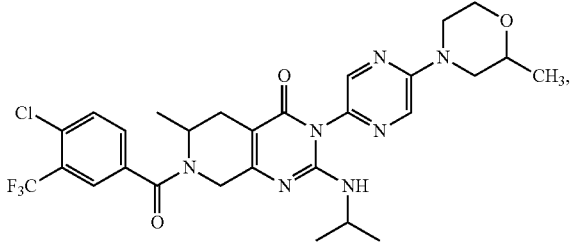
or a pharmaceutically acceptable salt of any of the foregoing.
The following are further examples of compounds of Formula (I), including pharmaceutically acceptable salts thereof:
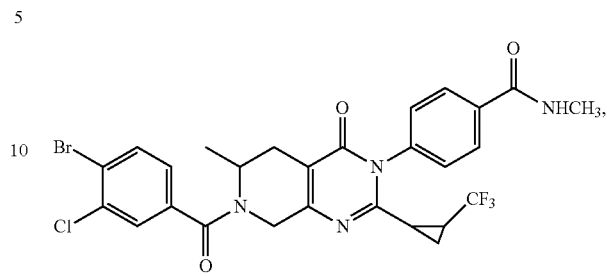
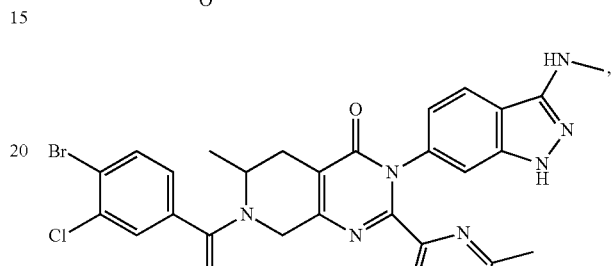
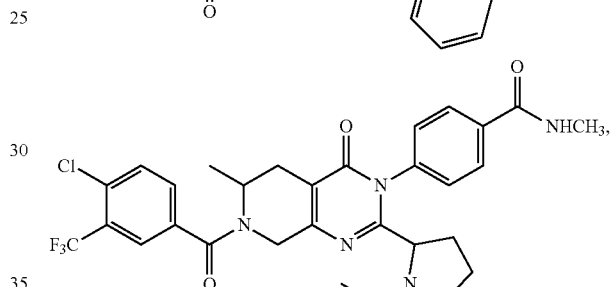
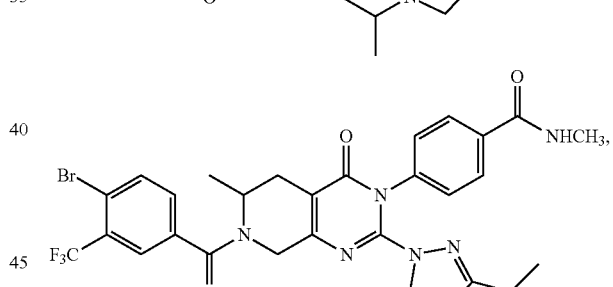
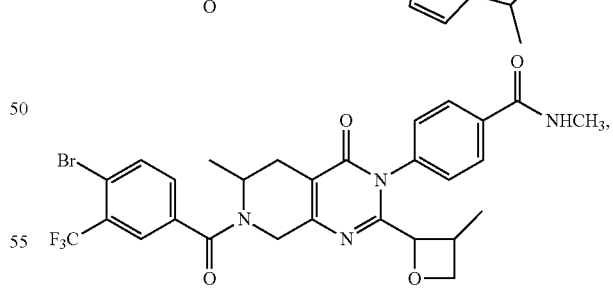
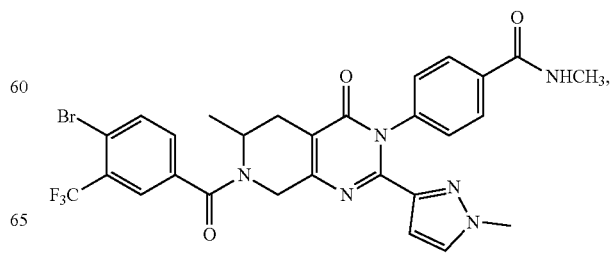

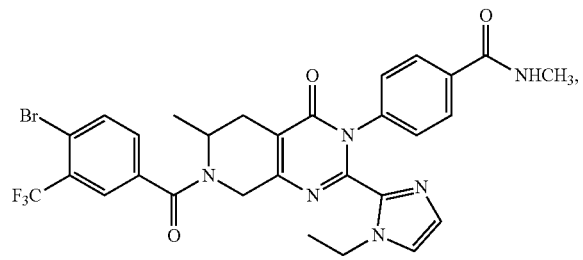
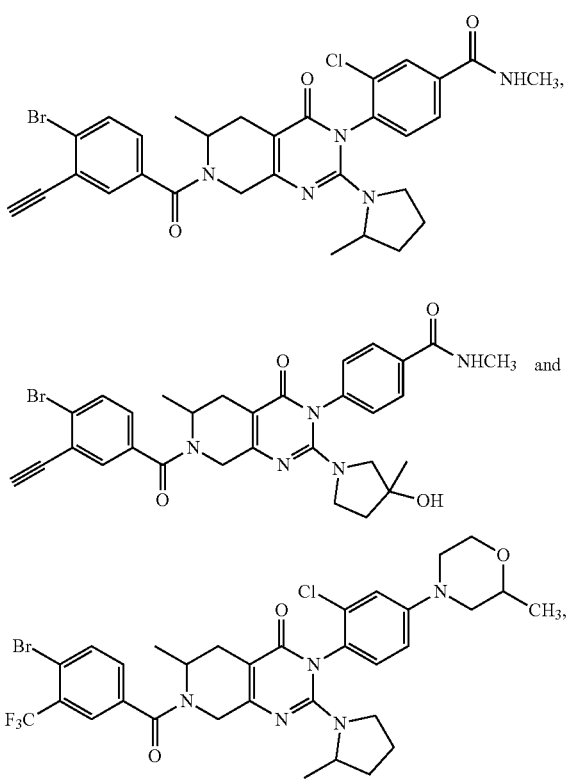
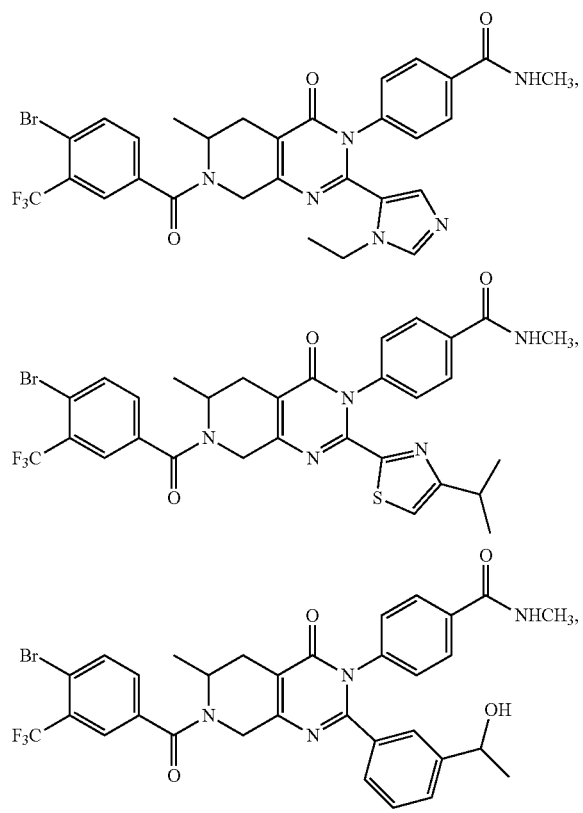
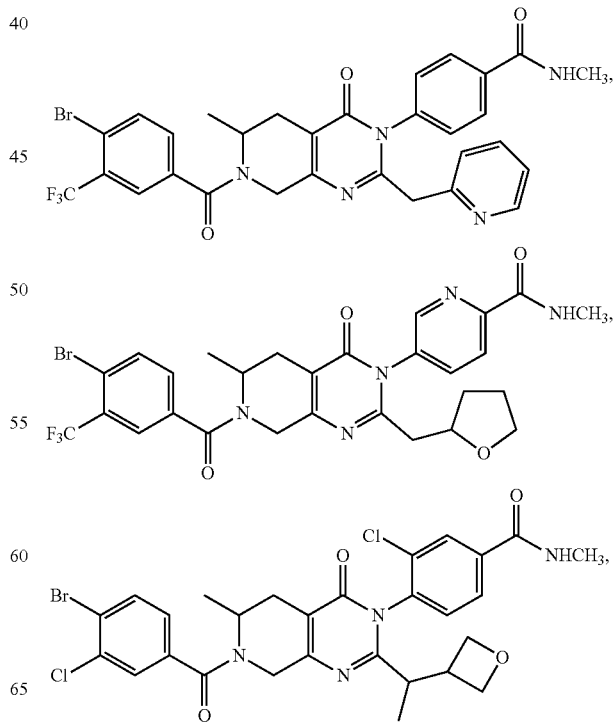
or a pharmaceutically acceptable salt of any of the foregoing.
Examples of compounds of Formula (I), including pharmaceutically acceptable salts thereof, include the following:

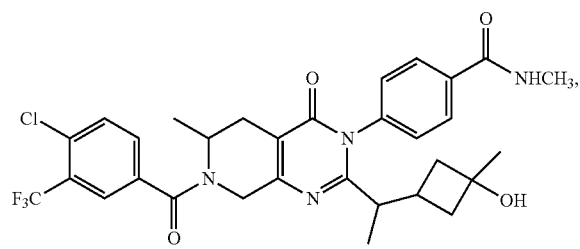
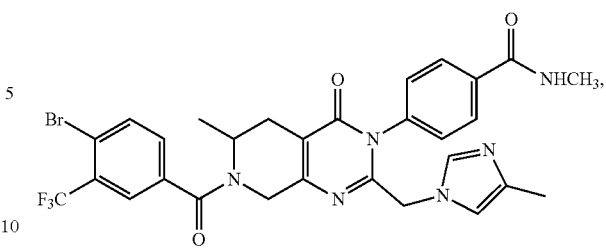
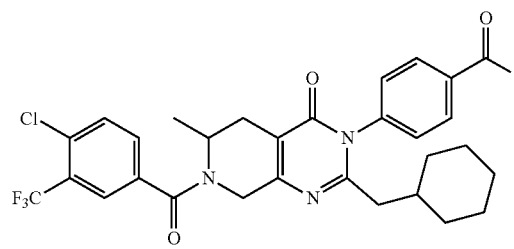
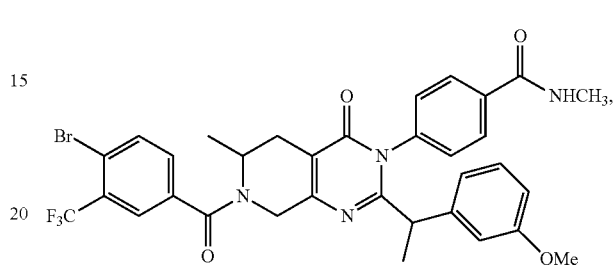
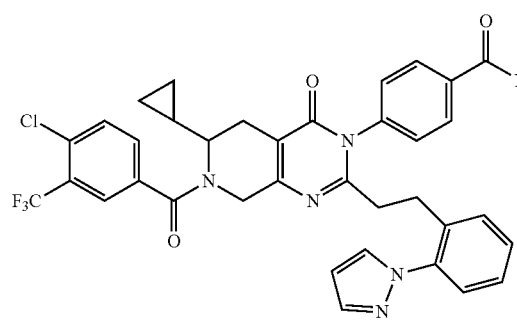
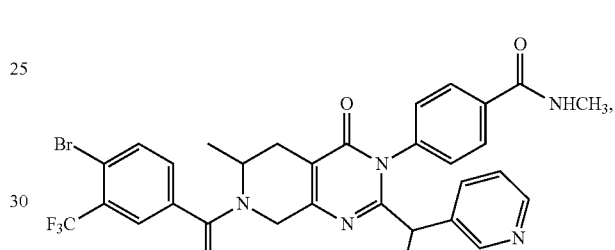
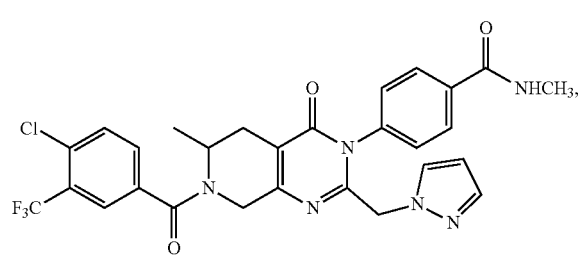
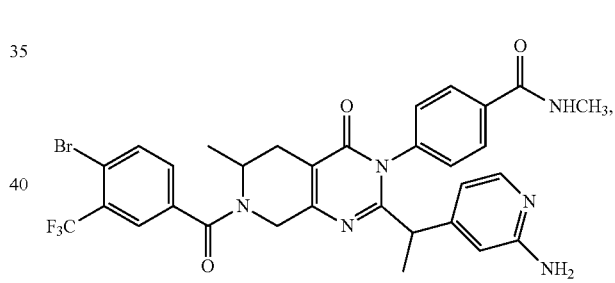
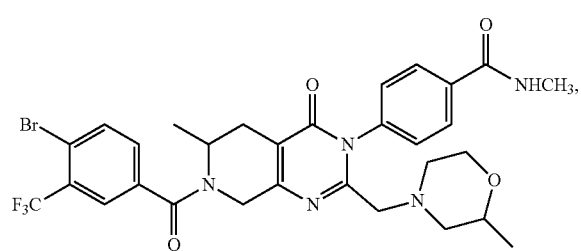
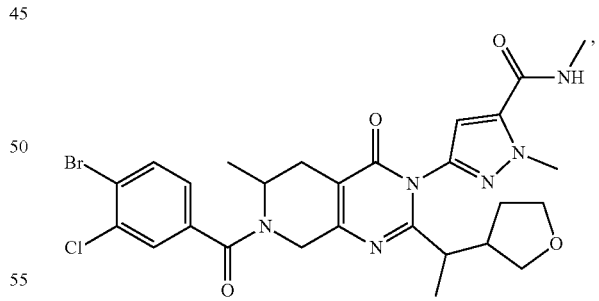
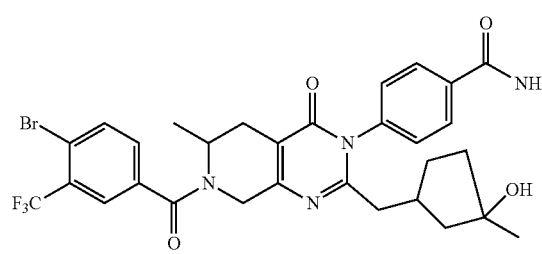
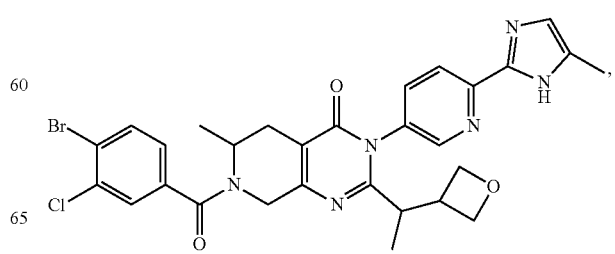

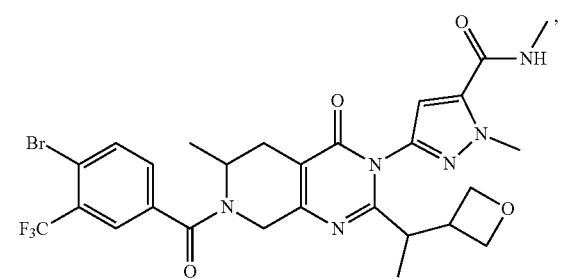
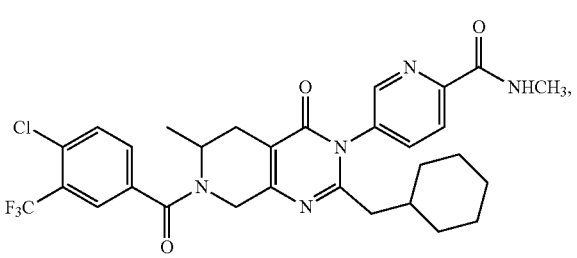
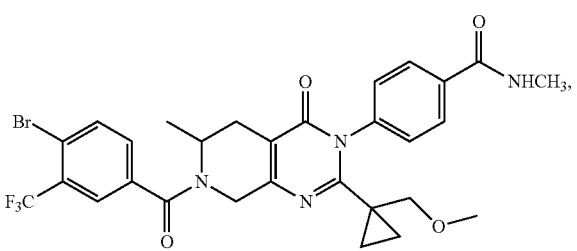
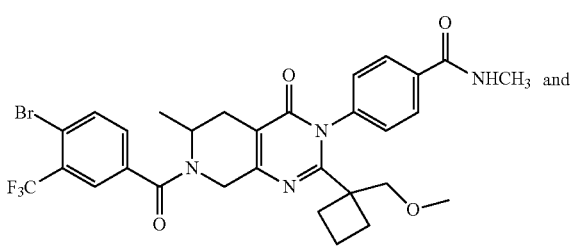
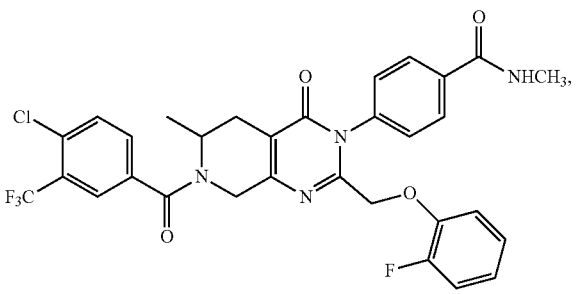
or a pharmaceutically acceptable salt of any of the foregoing.
Further examples of compounds of Formula (I), including pharmaceutically acceptable salts thereof, are provided below.
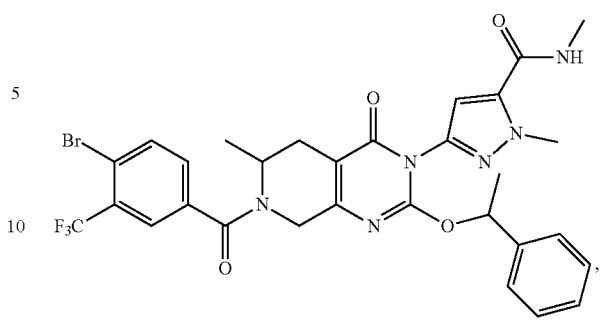
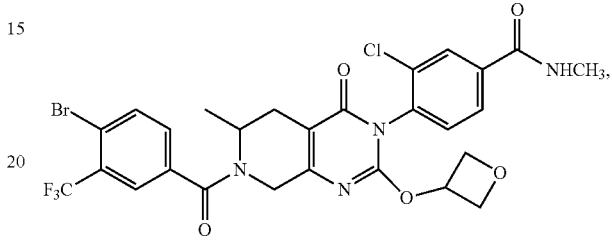
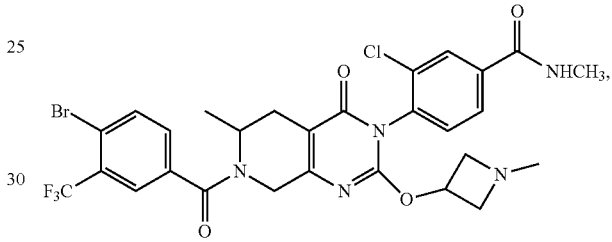
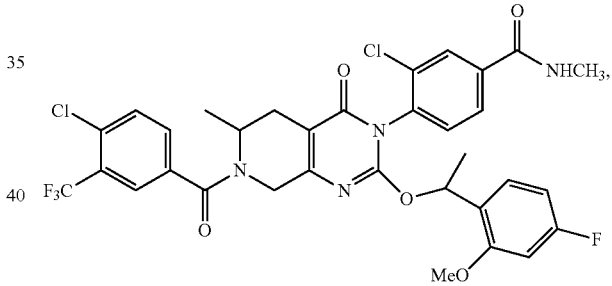
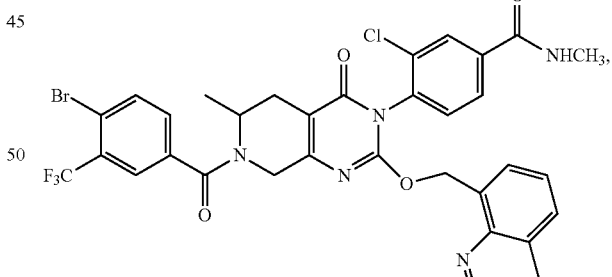
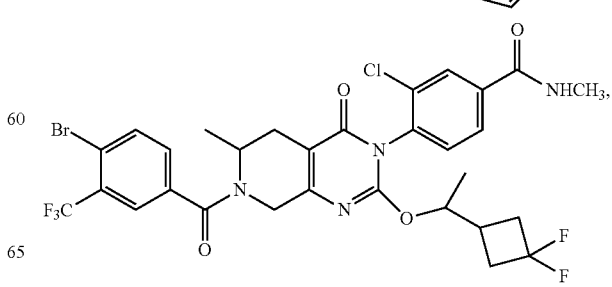

-continued

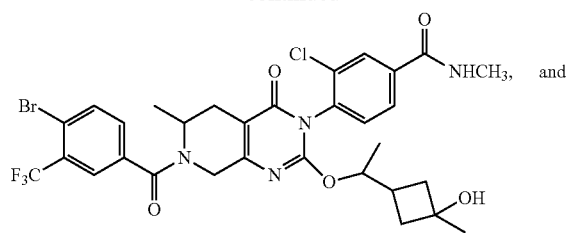

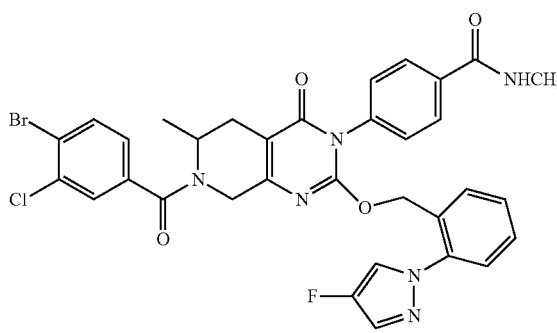

or a pharmaceutically acceptable salt of any of the foregoing.

Examples of compounds of Formula (I), including pharmaceutically acceptable salts thereof, include:

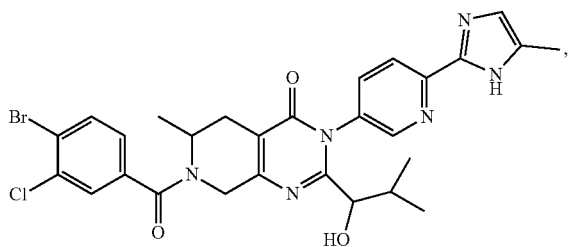

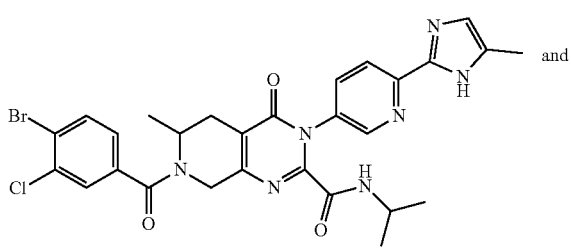

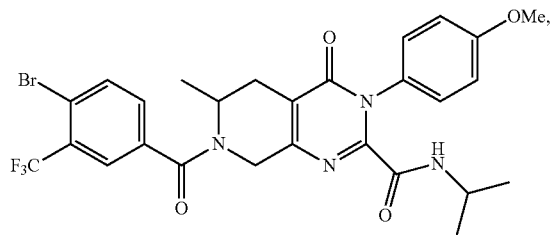

or a pharmaceutically acceptable salt of any of the foregoing.

Additional examples of compounds of Formula (I), including pharmaceutically acceptable salts thereof, include the following:

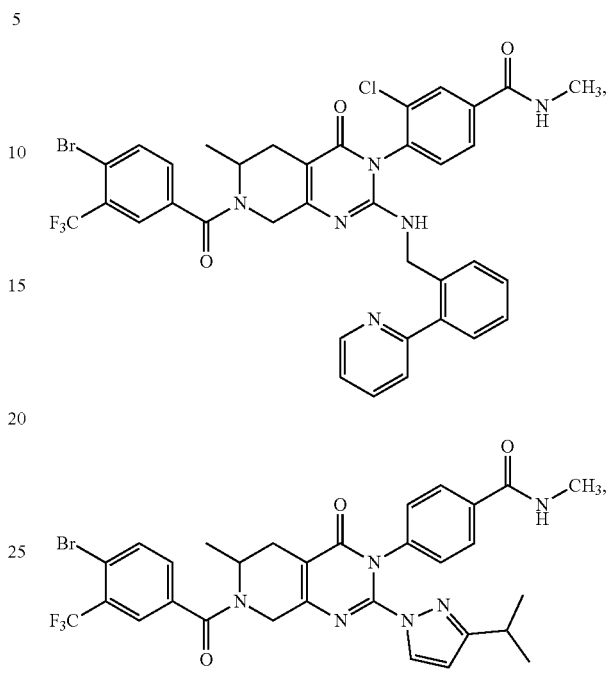

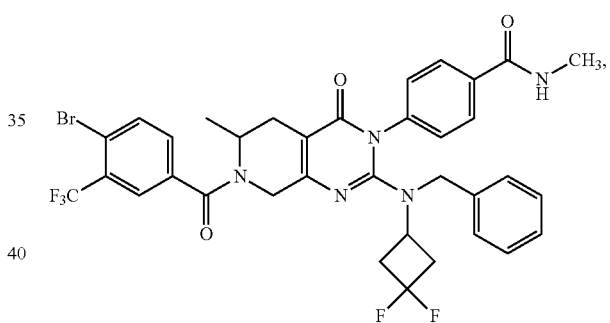

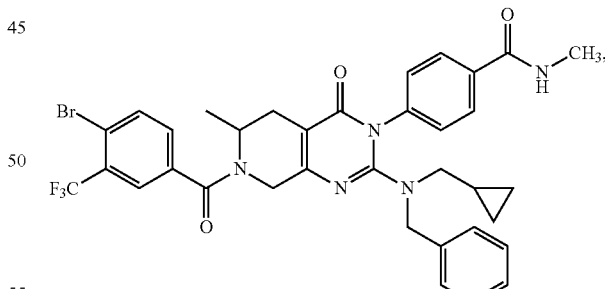

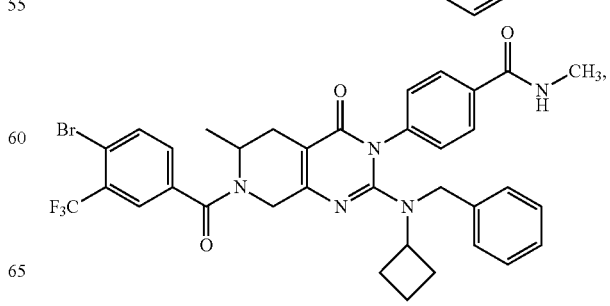

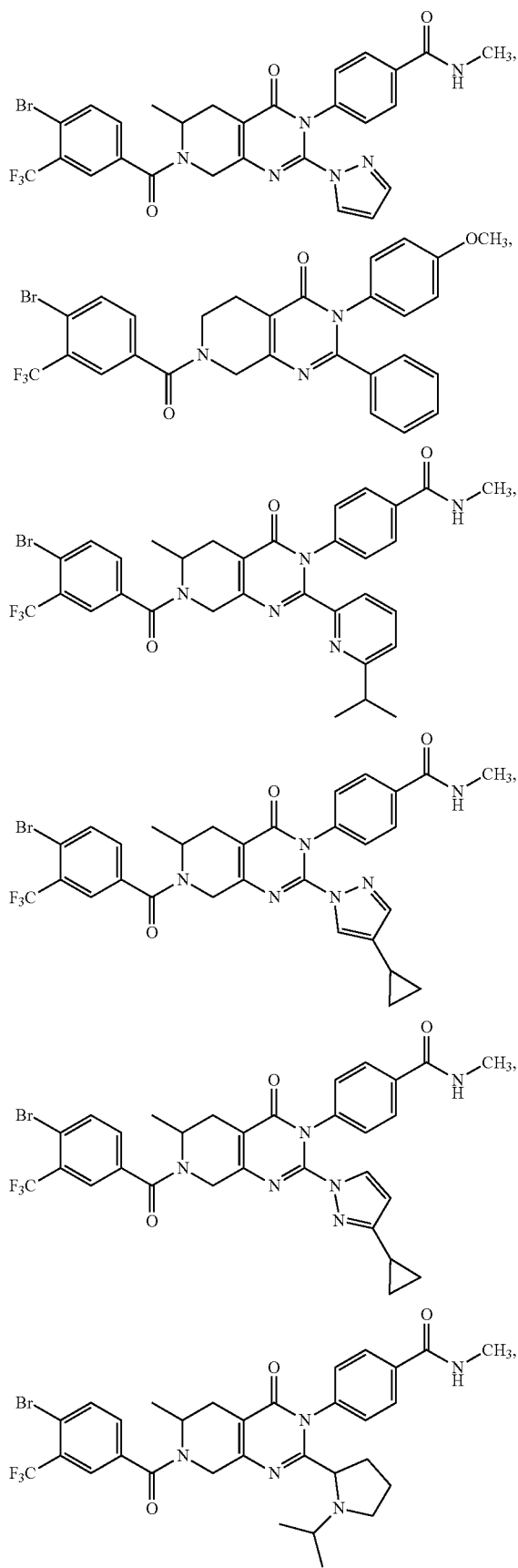
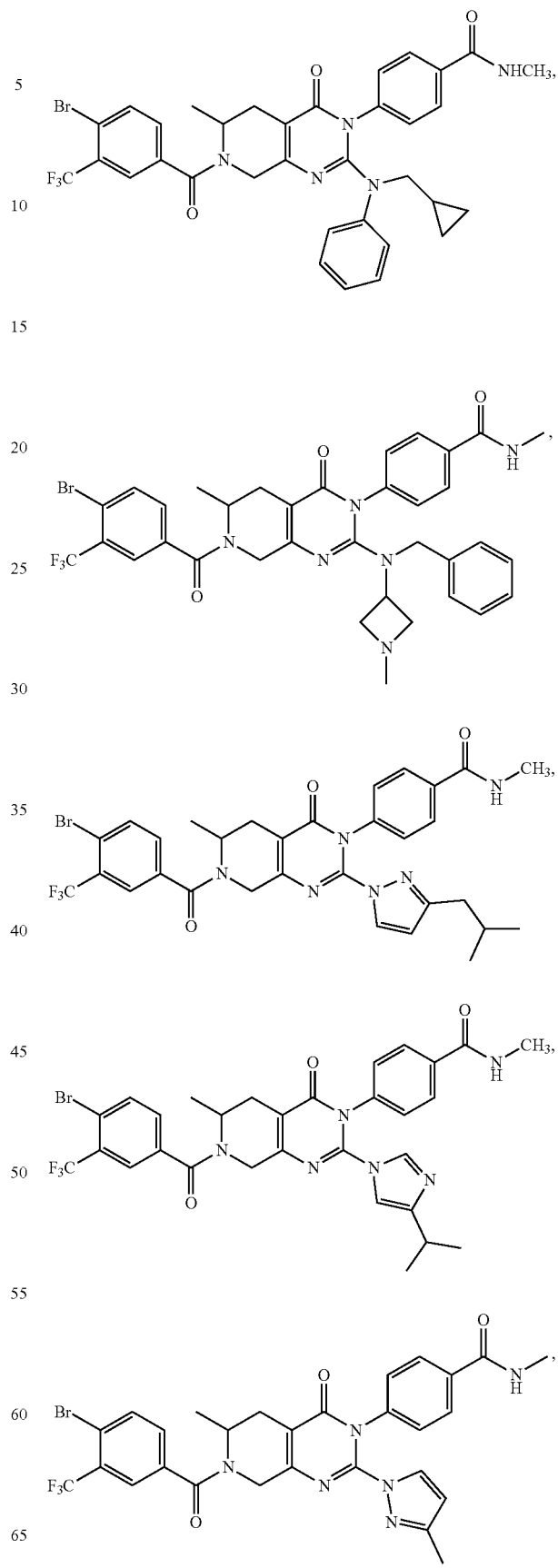

49
-continued
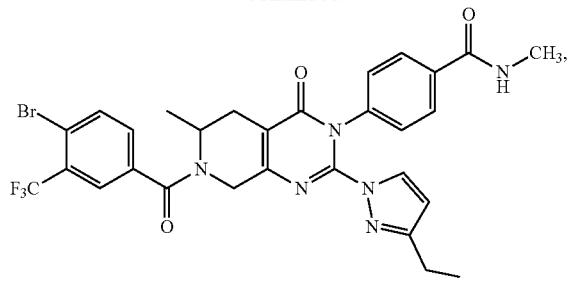
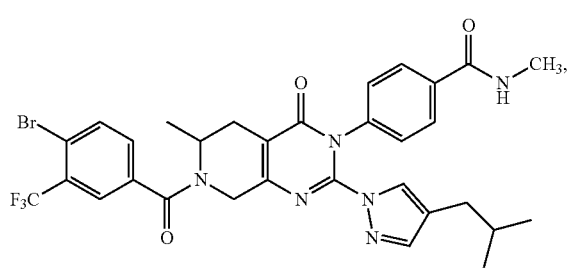
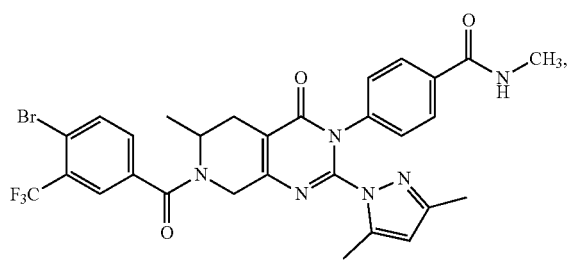
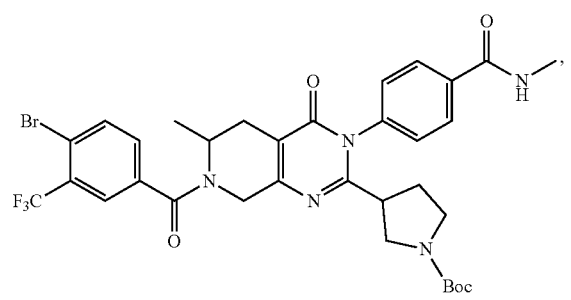
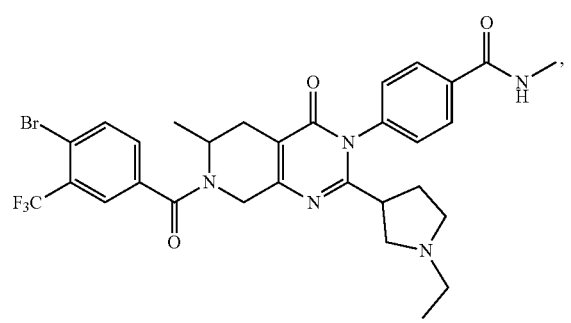
50
-continued
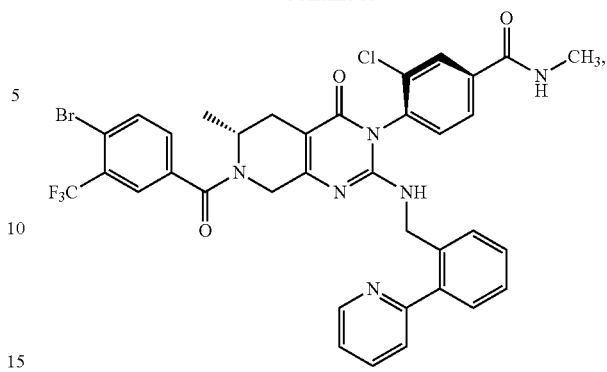
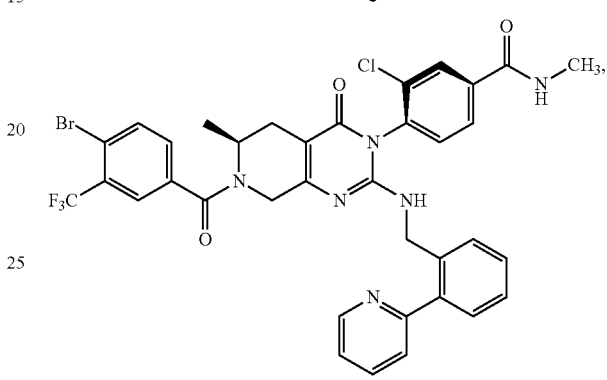
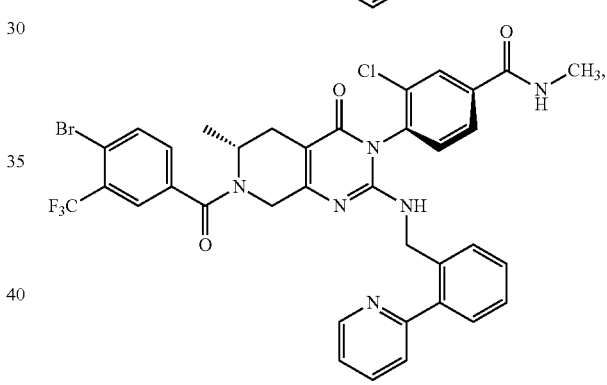
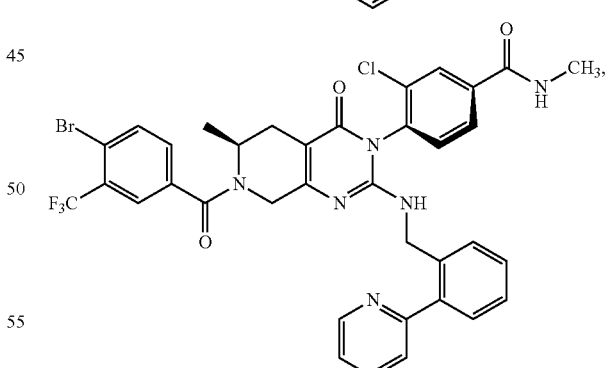
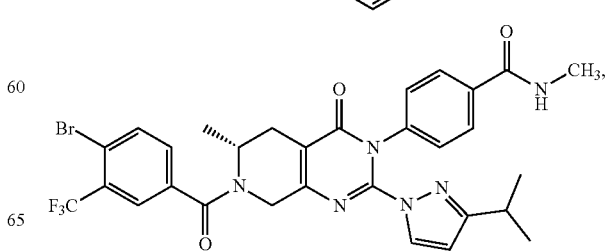

51
-continued
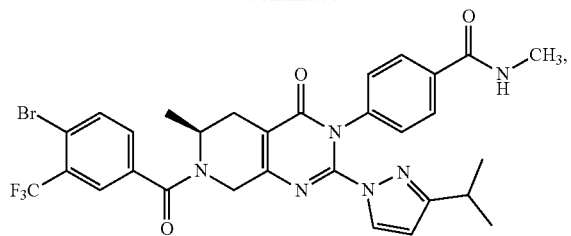
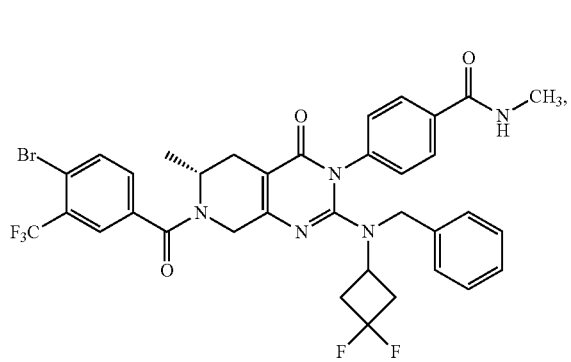
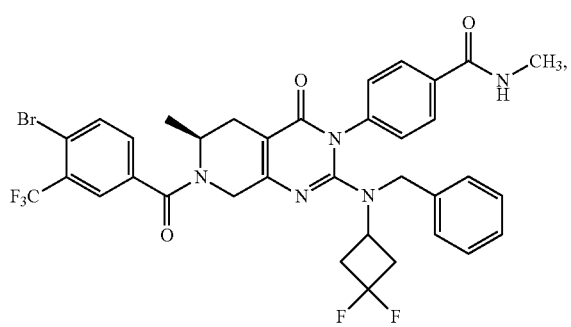
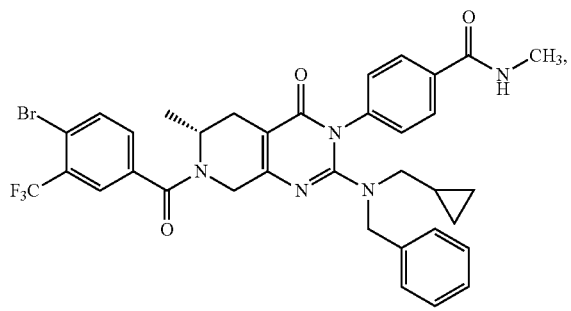
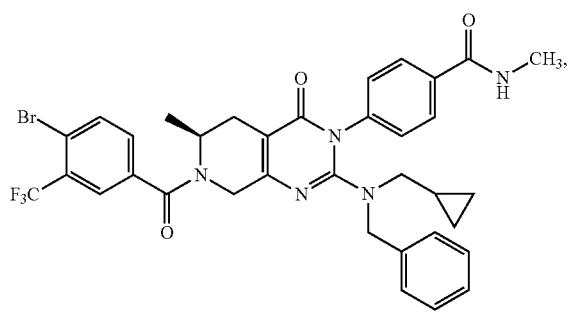
52
-continued
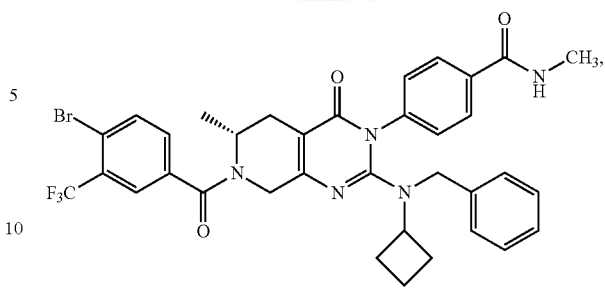
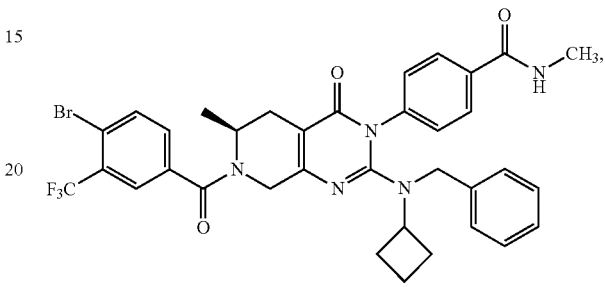
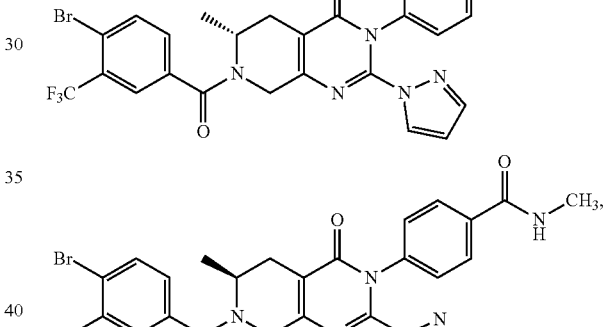
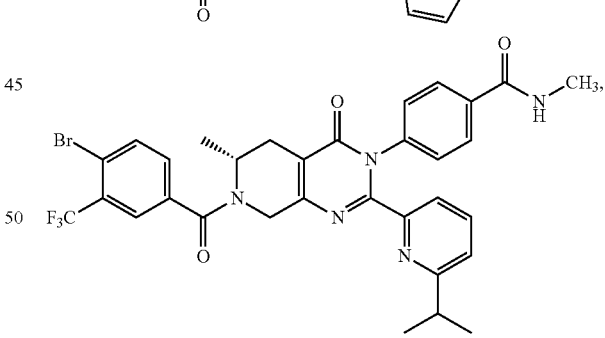
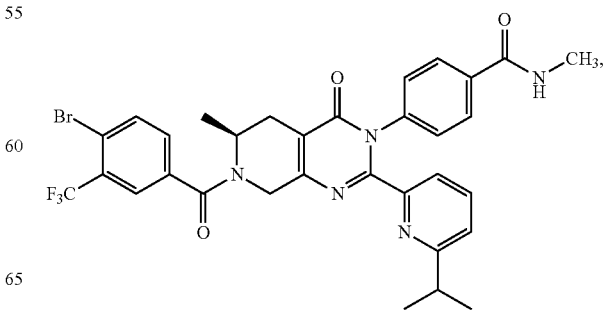

53
-continued
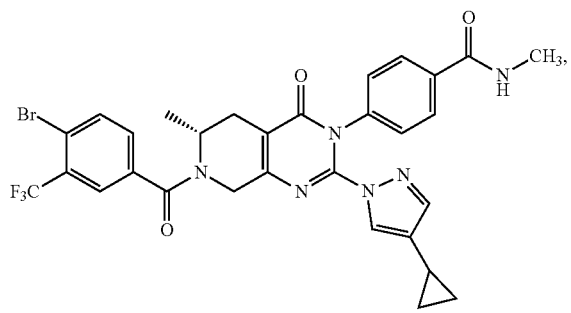
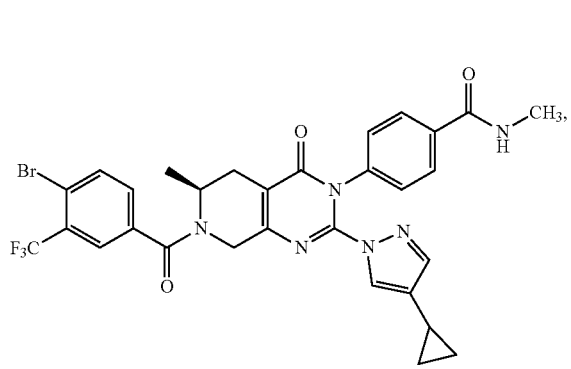
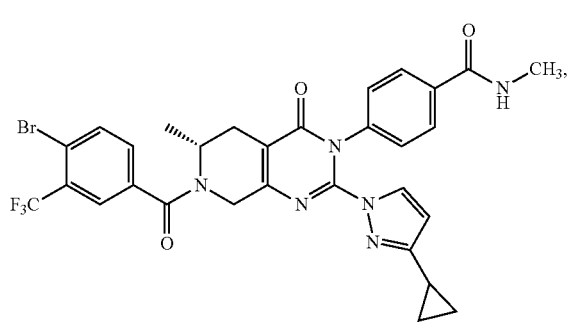 [SMILES: CNC(=O)c1ccc(-n2c(-n3ccc(C4CC4)n3)nc3c(c2=O)C[C@@H](C)N(C(=O)c2ccc(Br)c(C(F)(F)F)c2)C3)cc1]
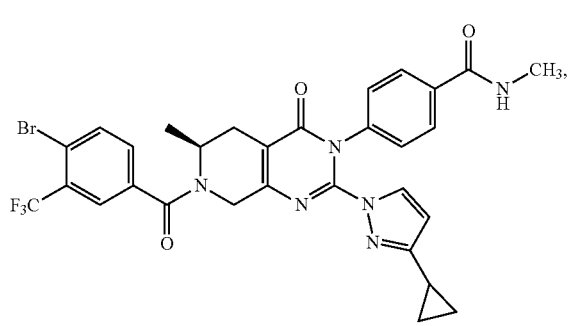
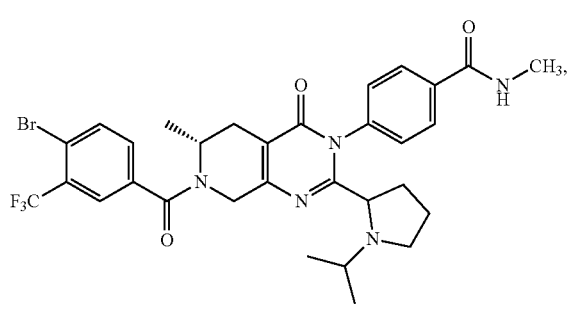
54
-continued
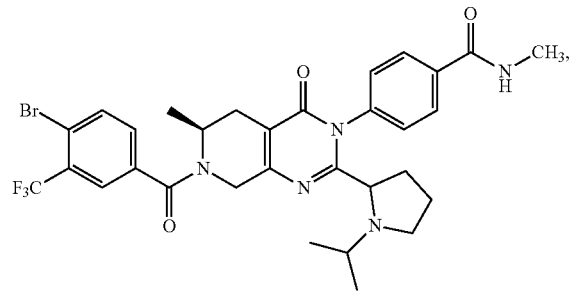
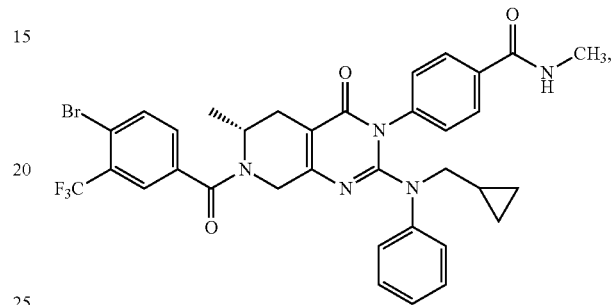
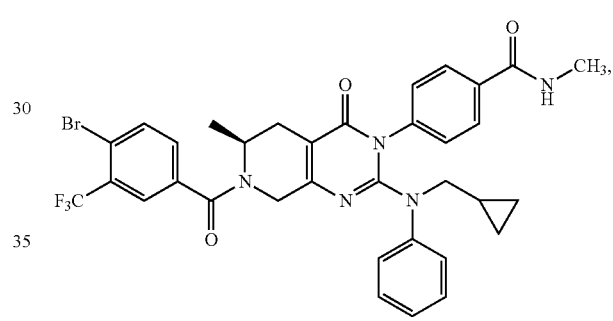
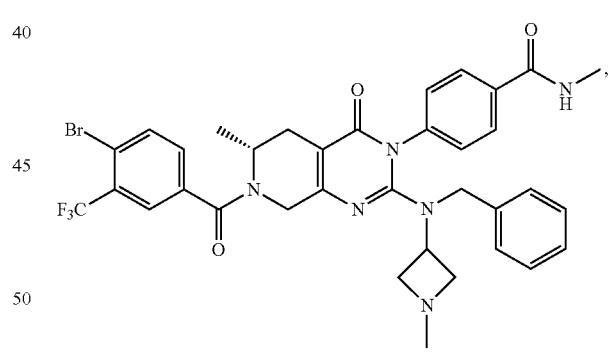
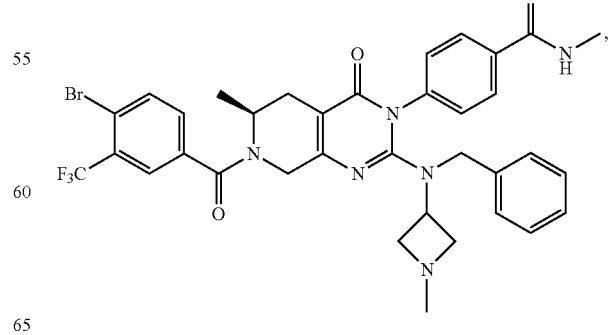

55
-continued
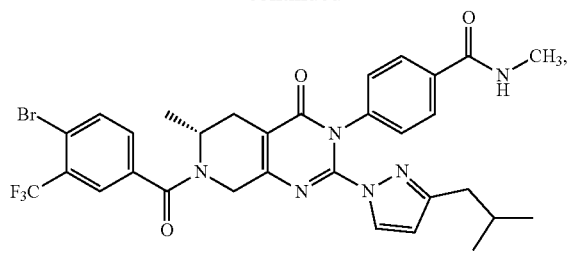
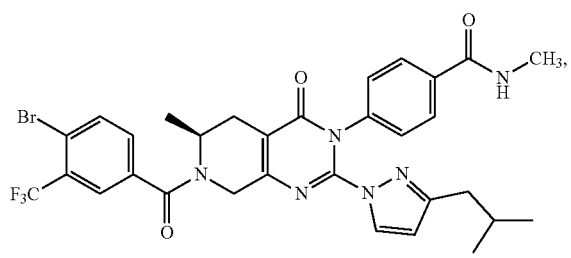
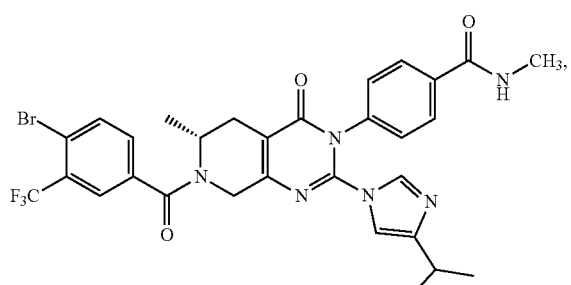
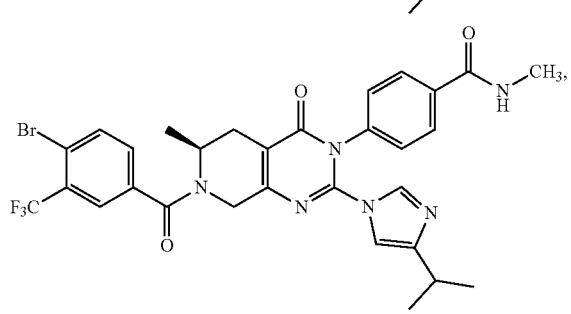
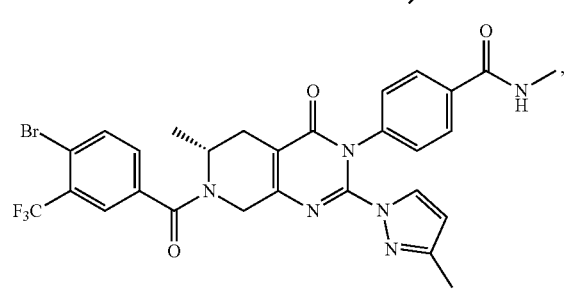
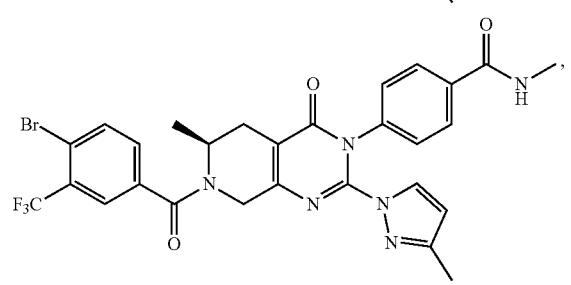
56
-continued
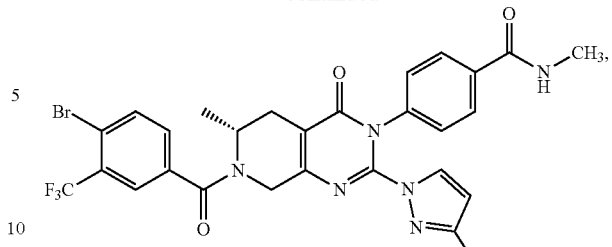
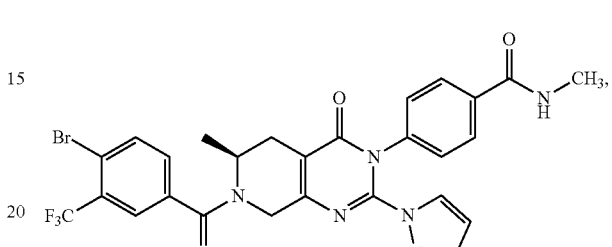
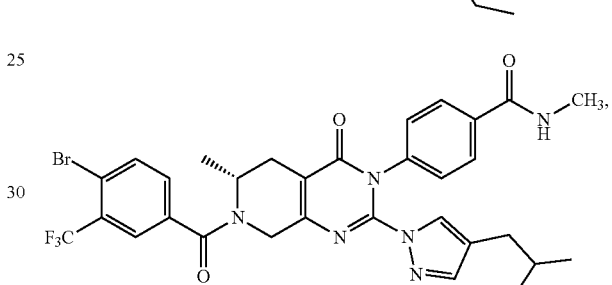
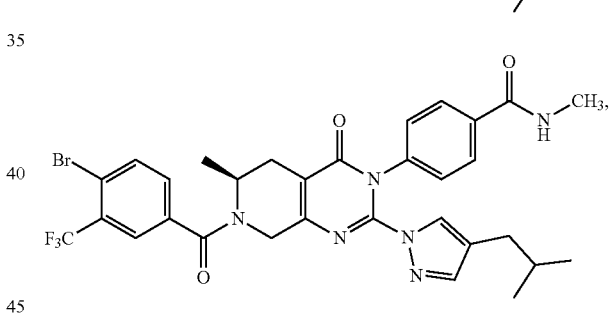
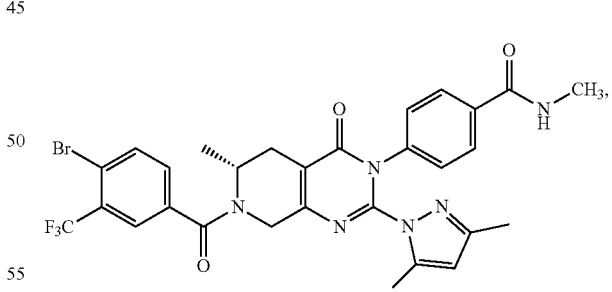
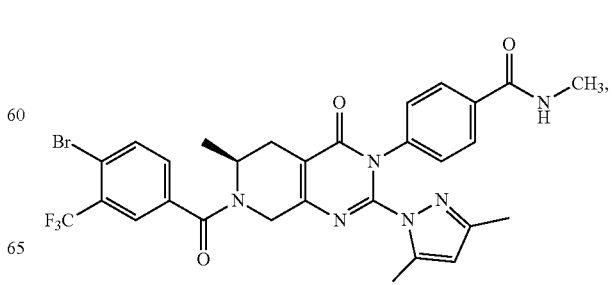

-continued

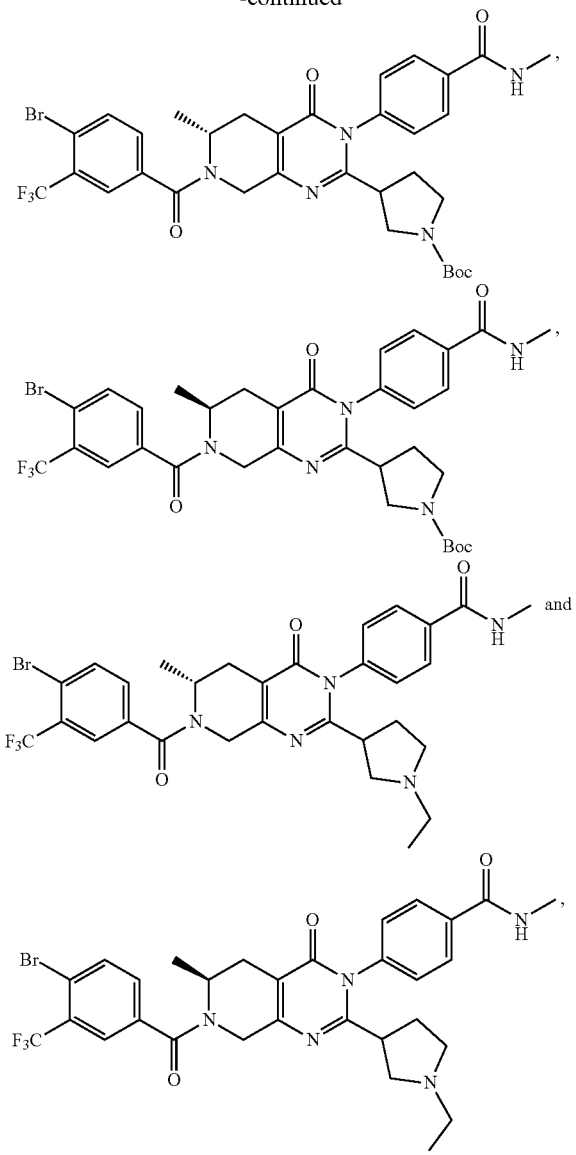

or a pharmaceutically acceptable salt of any of the foregoing.

In some embodiments, when n is 1, then $Z^1$ cannot be —C(=O)—. In other embodiments, when n is 1, then $Z^1$ cannot be —NH—C(=O)—. In some embodiments, $R^8$ cannot be —OR$^{10}$. In other embodiments, $R^8$ cannot be —SR$^{11}$. In still other embodiments, $R^8$ cannot be —NR$^{14A}$R$^{14B}$. In some embodiments, $R^8$ cannot be —OR$^{10}$, wherein $R^{10}$ is an unsubstituted $C_{1-6}$ alkyl. In some embodiments, $R^8$ cannot be —SR$^{11}$, wherein $R^{11}$ is an unsubstituted $C_{1-6}$ alkyl. In some embodiments, $R^8$ cannot be —NR$^{14A}$R$^{14B}$, wherein $R^{14A}$ is a monocyclic $C_{3-6}$ cycloalkyl optionally substituted with one or two halogens, an optionally substituted 5-6 member monocyclic heteroaryl or an optionally substituted 4-6 member monocyclic heterocyclyl; and $R^{14B}$ is an unsubstituted $C_{1-6}$ alkyl. In other embodiments, $R^8$ cannot be —NR$^{14A}$R$^{14B}$, wherein $R^{14A}$ is hydrogen, an unsubstituted $C_{1-6}$ alkyl (including an unsubstituted $C_{1-4}$ alkyl) or an unsubstituted $C_{2-6}$ alkenyl (including an unsubstituted $C_{2-3}$ alkenyl); and $R^{14B}$ is an unsubstituted $C_{1-6}$ alkyl, an optionally substituted aryl, an optionally substituted monocyclic $C_{3-6}$ cycloalkyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl). In some embodiments, $R^9$ can be substituted with a substituted heterocyclyl (such as a 5- to 6-membered monocyclic heterocyclyl), wherein the heterocyclyl can be substituted with one or more moieties independently selected from halogen, an unsubstituted $C_{1-4}$ alkyl, unsubstituted $C_{1-4}$ haloalkyl and an unsubstituted $C_{1-4}$ alkoxy. In some embodiments, when $R^8$ is —NR$^{14A}$R$^{14B}$ then $R^{14B}$ is not —CH$_2$-(phenyl substituted with methoxy). In some embodiments, $R^1$ cannot be selected from

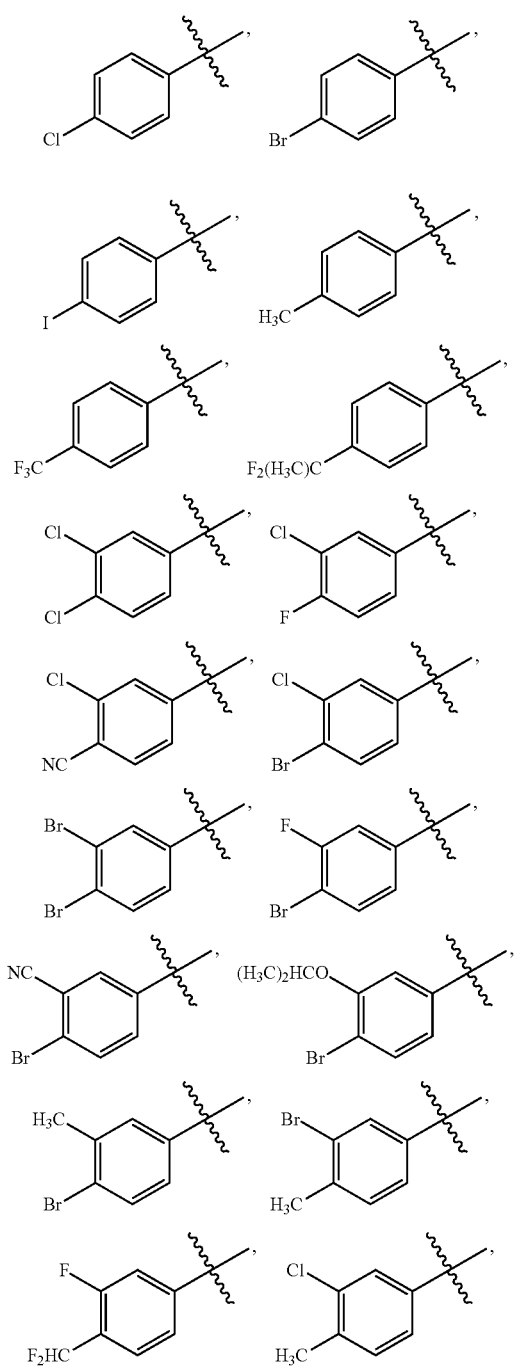

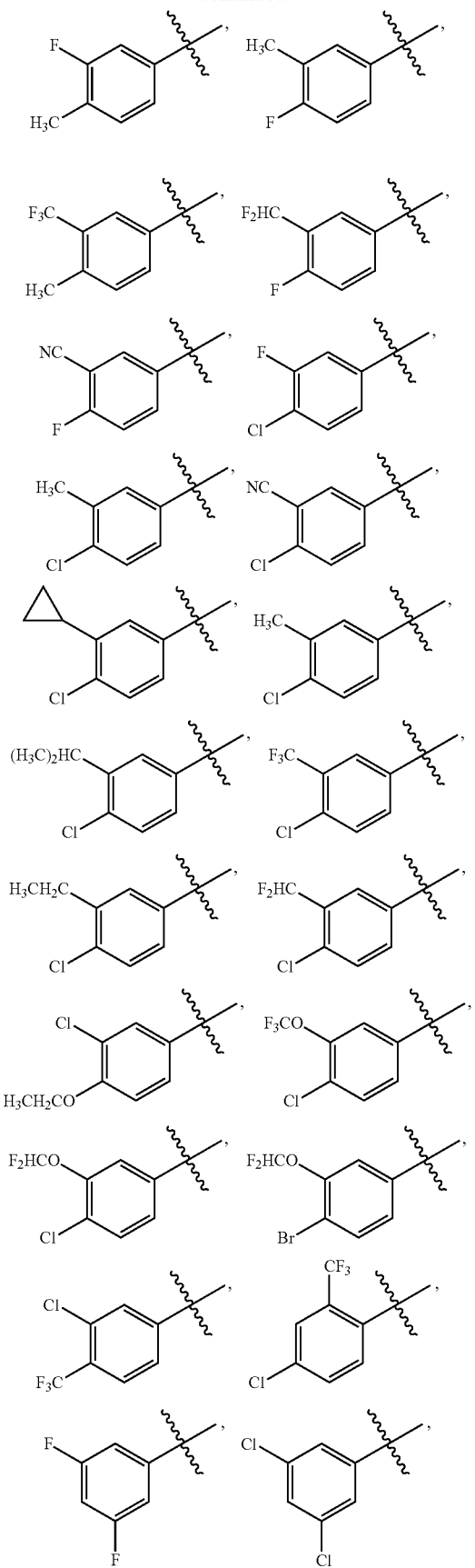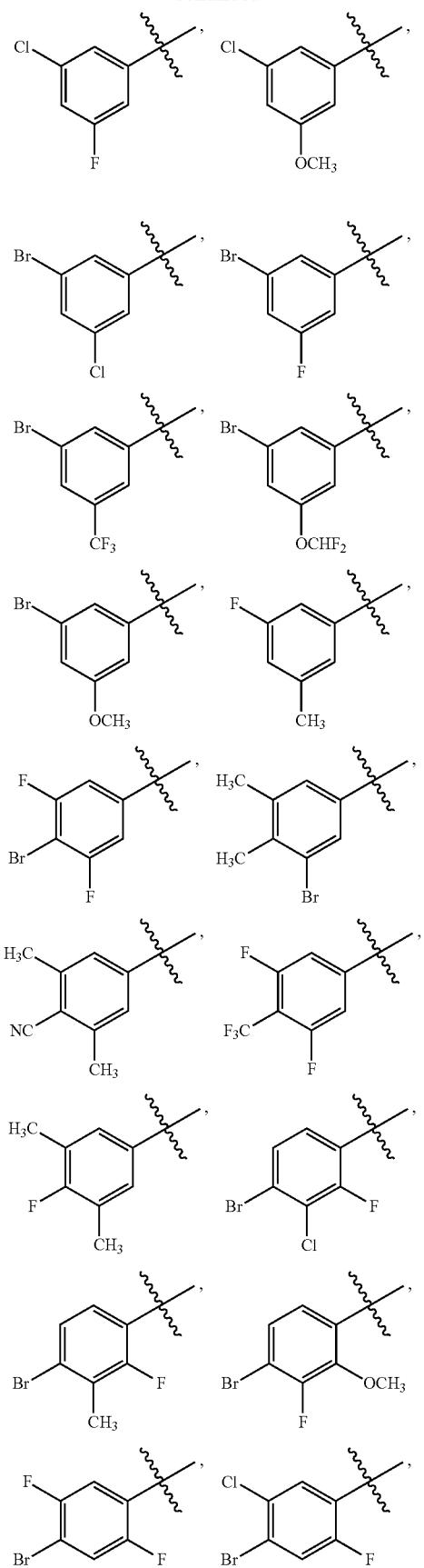

-continued

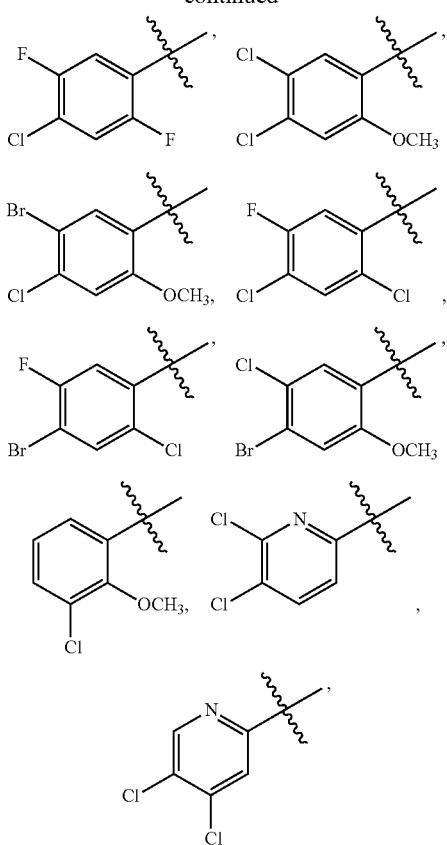

pyrrole, pyrazole, pyridine, thiophene, benzofuran, benzoxazole, benzothiazole, indole, indazole, indoline, indolizine, benzoimidazole, 2,3-dihydrobenzofuran, imidazo[1,2-a]pyridine, imidazo[1,5-a]pyridine, [1,2,4]triazolo[1,5-a]pyridine, isoquinoline, quinoxaline, chromane, pyrrolo[3,2-b]pyridine, pyrrolo[3,2-c]pyridine, thieno[3,2-b]pyrrole, thieno[2,3-c]pyridine, isoindolin-1-one, 1,3-dihydro-2H-benzo[d]imidazol-2-one, benzo[b]thiophene 1,1-dioxide, 1H-benzo[d][1,2,3]triazole and pyrazolo[1,5-a]pyridine, such as when $R^8$ is —$NR^{14A}R^{14B}$, —$OR^{10}$ or —$SR^{11}$. In some embodiments, $R^1$ cannot be

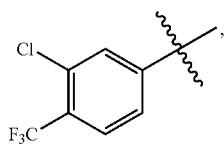

when n is 1, and $Z^1$ is —C(=O)—. In some embodiments, $R^1$ cannot be

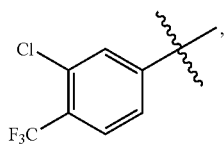

when n is 1, $Z^1$ is —C(=O)— and $R^9$ is a substituted phenyl, for example, when $R^9$ is a substituted phenyl substituted with an unsubstituted $C_{1-4}$ alkoxy (such as methoxy) or —C(=O)$NHR^{15}$, wherein $R^{15}$ is an unsubstituted $C_{1-6}$ alkyl (such as methyl). In some embodiments, when $R^1$ is

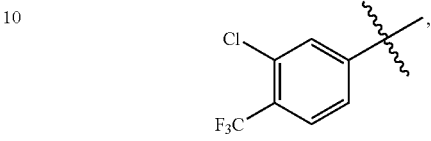

n is 1, $Z^1$ is —C(=O)—, $R^9$ is a substituted phenyl (for example, when $R^9$ is a substituted phenyl substituted with an unsubstituted $C_{1-4}$ alkoxy (such as methoxy) or —C(=O) $NHR^{15}$, wherein $R^{15}$ is an unsubstituted $C_{1-6}$ alkyl (such as methyl)) and $R^8$ is —$NHR^{14B}$, then $R^{14B}$ cannot be an optionally substituted aryl($C_{1-4}$ alkyl) (such as an unsubstituted or a substituted benzyl). In some embodiments, $R^1$ cannot be

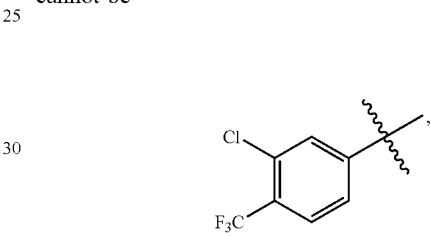

when n is 1, $Z^1$ is —C(=O)— and $R^9$ is a substituted pyrazole, for example, when $R^9$ is a substituted pyrazole substituted with an unsubstituted $C_{1-4}$ alkyl (such as methyl) or —C(=O)$NHR^{15}$, wherein $R^{15}$ is an unsubstituted $C_{1-6}$ alkyl (such as methyl). In some embodiments, when $R^1$ is

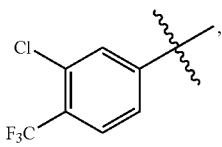

n is 1, $Z^1$ is —C(=O)—, $R^9$ is a substituted pyrazole (for example, when $R^9$ is a substituted pyrazole substituted with an unsubstituted $C_{1-4}$ alkyl (such as methyl) or —C(=O) $NHR^{15}$, wherein $R^{15}$ is an unsubstituted $C_{1-6}$ alkyl (such as methyl)) and $R^8$ is —$NHR^{14B}$, then $R^{14B}$ cannot be an optionally substituted aryl($C_{1-4}$ alkyl) (such as an unsubstituted or a substituted benzyl). In some embodiments, a compound of Formula (I), or a pharmaceutically acceptable salt thereof, cannot be a compound disclosed in WO 2020/182990, which is hereby incorporated by reference. In some embodiments, a compound of Formula (I), or a pharmaceutically acceptable salt thereof, cannot be selected from 4-((R)-7-(4-chloro-3-(trifluoromethyl)benzoyl)-6-methyl-4-oxo-2-(((S)-1-(4-(trifluoromethyl)phenyl)ethyl)amino)-5,6,7,8-tetrahydropyrido[3,4-d]pyrimidin-3(4H)-yl)-N-methylbenzamide

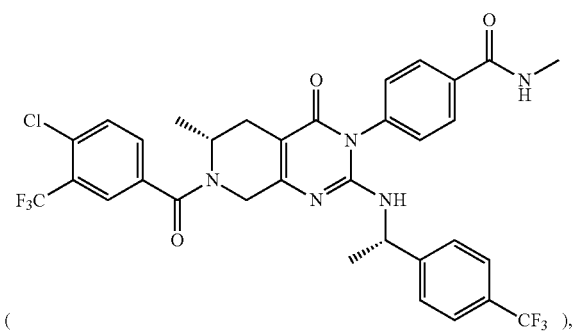

4-((R)-7-(4-chloro-3-(trifluoromethyl)benzoyl)-2-(((S)-1-(4-fluorophenyl)ethyl)amino)-6-methyl-4-oxo-5,6,7,8-tetrahydropyrido[3,4-d]pyrimidin-3(4H)-yl)-N-methylbenzamide (

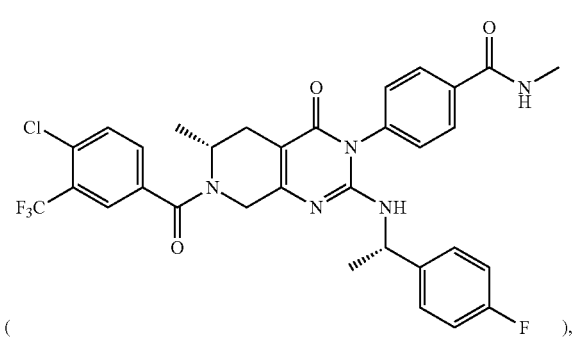 [SMILES: CNC(=O)c1ccc(-n2c(N[C@@H](C)c3ccc(F)cc3)nc3c(c2=O)C[C@@H](C)N(C(=O)c2ccc(Cl)c(C(F)(F)F)c2)C3)cc1]

3-((R)-7-(4-chloro-3-(trifluoromethyl)benzoyl)-2-(((S)-1-(4-fluorophenyl)ethyl)amino)-6-methyl-4-oxo-5,6,7,8-tetrahydropyrido[3,4-d]pyrimidin-3(4H)-yl)-N,1-dimethyl-1H-pyrazole-5-carboxamide

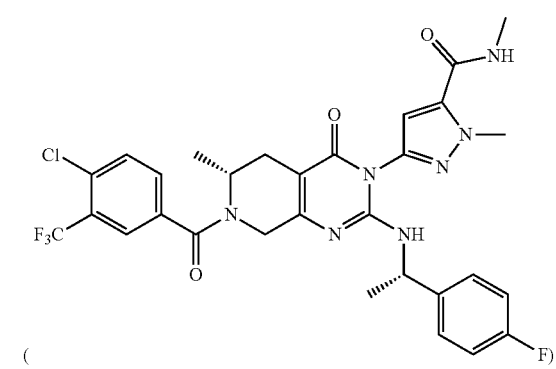

and 5-((R)-7-(4-chloro-3-(trifluoromethyl)benzoyl)-2-(((S)-1-(4-fluorophenyl)ethyl)amino)-6-methyl-4-oxo-5,6,7,8-tetrahydropyrido[3,4-d]pyrimidin-3(4H)-yl)-N,1-dimethyl-1H-pyrazole-3-carboxamide

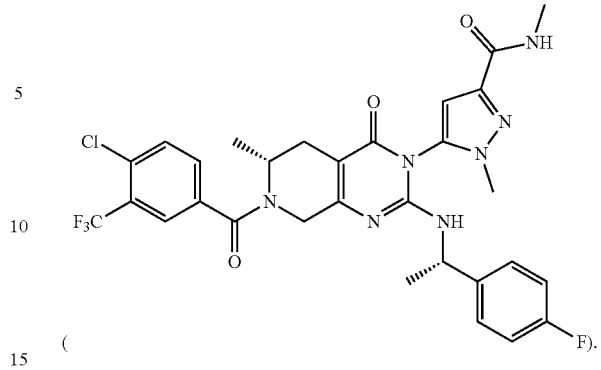

Synthesis

Compounds of Formula (I) along with those described herein may be prepared in various ways. General synthetic routes for preparing compounds of Formula (I) are shown and described herein along with some examples of starting materials used to synthesize compounds described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

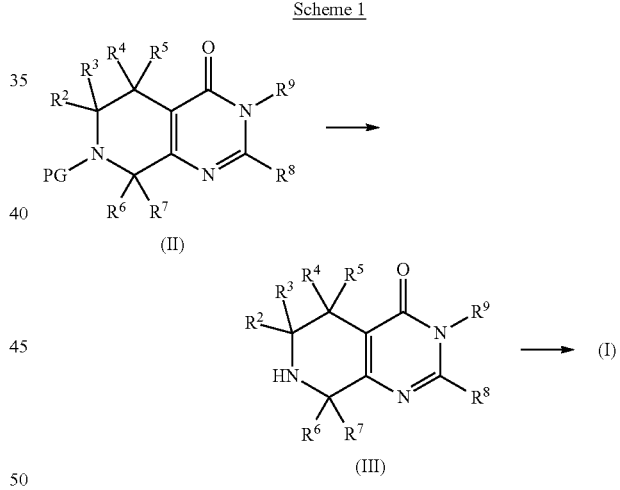

Compounds of Formula (I) can be prepared from an intermediate of Formula (II), in which PG represents an amino protecting group such as Boc. The PG group can be cleaved from a compound of Formula (II) using methods known in the art. For example, when PG represents a Boc group, PG can be cleaved using acidic conditions, for example, in the presence of HCl in a suitable solvent (such as 1,4-dioxane) or in the presence of cupper triflate. The coupling of the intermediate of Formula (III) with a suitable agent can afford a compound of Formula (I), along with pharmaceutically acceptable salts thereof. As an example, compounds of Formula (I), along with pharmaceutically acceptable salts thereof, wherein $Z^1$ represents —NH—C(=O)— and n=1, can be obtained by reacting a compound of Formula (III) with a phenyl carbamate of general formula $R^1$—NH—C(=O)—O— phenyl or with an isocyanate of general formula R¹—N=C=O, in the presence of a suitable base in a suitable solvent. An example of a suitable base is triethylamine and an example of suitable solvent is acetonitrile.

Other compounds of Formula (I), along with pharmaceutically acceptable salts thereof, wherein $Z^1$ represents —C(=O)— and n=1, can be obtained by reacting a compound of Formula (III) with an acyl chloride of general formula R¹—C(=O)—Cl in the presence of a base in a suitable solvent. Additional compounds of Formula (I) and pharmaceutically acceptable salts thereof, wherein $Z^1$ represents —C(=O)— and n=1, can be obtained by reacting compound of Formula (III) with an carboxylic acid of general formula R¹—C(=O)—OH in the presence of an amide coupling agent (such as HATU) in a suitable solvent. Further compounds of Formula (I), along with pharmaceutically acceptable salts thereof, can be prepared from a compound of Formula (III) using methods known in the art.

Scheme 2

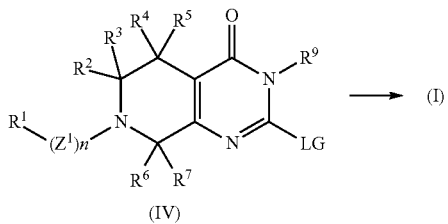

(IV)

Compounds of Formula (I), including pharmaceutically acceptable salts thereof, can also be prepared from an intermediate of Formula (IV), in which LG represents a leaving group (such as sulfhydryl, methylsulfoxide or halo, in particular chloro of bromo). A compound of Formula (I) in which $R^8$ represents —$NR^{14A}R^{14B}$ can be prepared from a compound of Formula (IV) in which LG represents methylsulfoxide by reacting an amine of Formula $HNR^{14A}R^{14B}$, in the presence of a base (such as diisopropylethylamine (DIPEA) or sodium bicarbonate) in a suitable solvent (such as 1,4-dioxane or acetonitrile), optionally in the presence of a catalyst (for example, DMAP). A compound of Formula (I) in which $R^8$ represents —$NR^{14A}R^{14B}$ can be prepared from a compound of Formula (IV) in which LG represents chloro by reacting an amine of Formula $HNR^{14A}R^{14B}$, in the presence of a base (for example, triethylamine, sodium bicarbonate or DIPEA) in a suitable solvent (such as acetonitrile, n-butanol or dioxane), optionally in the presence of a catalyst, such as DMAP. A compound of Formula (I) in which $R^8$ represents —$OR^{10}$ can be prepared from a compound of Formula (IV) in which LG represents chloro by reacting an alcohol of Formula $HOR^{10}$ in the presence or absence of a base (such as NaH) in a suitable solvent (for example, acetonitrile).

Scheme 3

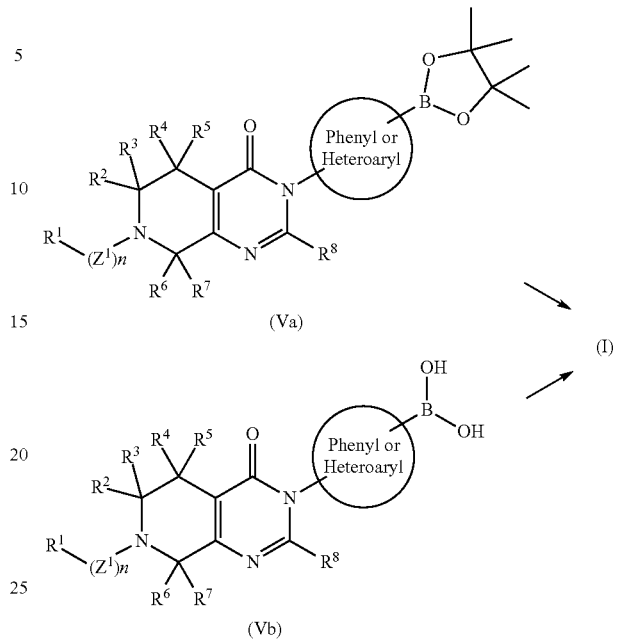

A compound of Formula (I), along with pharmaceutically acceptable salts thereof, in which $R^9$ represents a phenyl or a heteroaryl substituted with an optionally substituted heteroaryl, can be prepared from an intermediate of Formula (Va) and an optionally substituted bromoheteroaryl using a palladium catalyst (such as $Pd(PPh_3)_4$) in the presence of a base (for example, $Cs_2CO_3$) in a suitable solvents (such as 1,4-dioxane/$H_2O$). The optionally substituted bromoheteroaryl can also be replaced in a similar reaction using an optionally substituted iodoheteroaryl. The boronic ester intermediate of Formula (Va) can be replaced with a boronic acid of Formula (Vb) using similar reaction conditions to afford a compound of Formula (I), or a pharmaceutically acceptable salt thereof.

Scheme 4

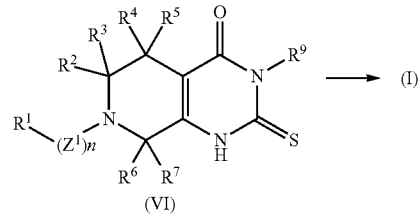

Compounds of Formula (I), including pharmaceutically acceptable salts thereof, wherein $R^8$ represents —$SR^{11}$ can be prepared from an intermediate of Formula (VI) and an halogen derivative of general formula $XR^{11}$, in which X represents an halogen (such as Cl, Br or I) in the presence of a base, such as potassium carbonate or DBU, in a suitable solvent (for example, DMF). Compounds of Formula (I) in which $R^8$ represents —$NR^{14A}R^{14B}$ can be prepared from an intermediate of Formula (VI) and an amine of general formula $HNR^{14A}R^{14B}$ in the presence of tert-Butyl hydroperoxide (TBHP) in a suitable solvent (such as acetonitrile).

Scheme 5

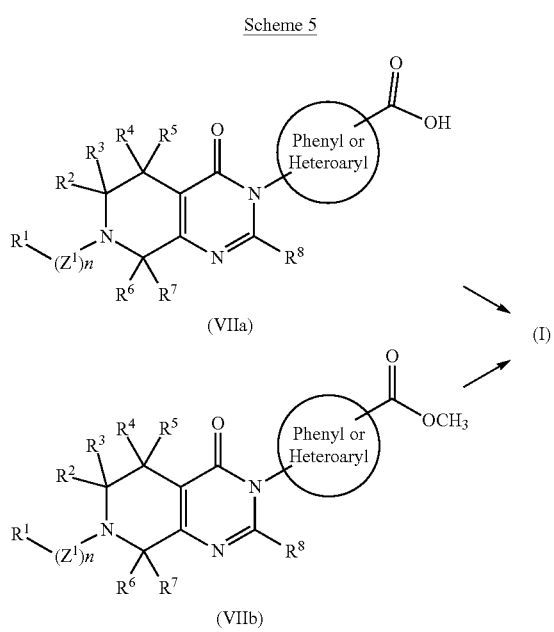

Compounds of Formula (I), including pharmaceutically acceptable salts thereof, in which $R^9$ represents a phenyl substituted with —C(=O)NHR$^{15}$ or $R^9$ represents an heteroaryl substituted with —C(=O)NHR$^{15}$ can be prepared from an acid intermediate of general formula (VIIa) and an amine of Formula NH$_2$—R$^{15}$, using a peptide coupling agent (such as CDI) in the presence of a base (for example, DBU) in a suitable solvent, such as acetonitrile or DMF. Compounds of Formula (I), along with pharmaceutically acceptable salts thereof, in which $R^9$ represents a phenyl substituted with —C(=O)NHR$^{15}$ or $R^9$ represents an heteroaryl substituted with —C(=O)NHR$^{15}$ can be prepared from an ester intermediate of Formula (VIIb) and an amine of general formula NH$_2$—R$^{15}$ in a suitable solvent (such as acetonitrile).

Scheme 6

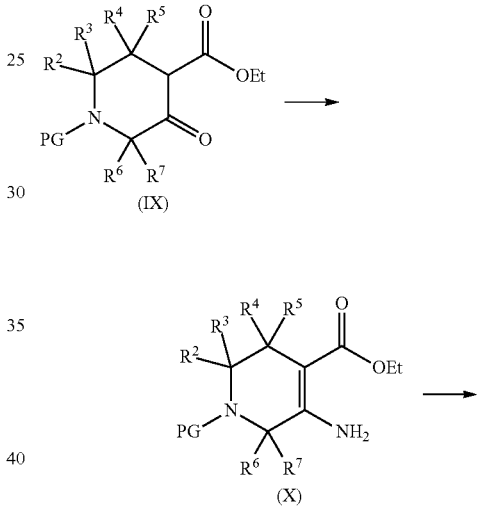

Compounds of Formula (I), or a pharmaceutically acceptable salt thereof, in which $R^9$ represents a phenyl or an heteroaryl substituted with a mono-substituted amine, can be prepared from an intermediate of Formula (VIII) and an mono-substituted amine, using a catalyst (for example, XantPhos Pd G3) in the presence of a base (such as Cs$_2$CO$_3$) in a suitable solvent (such as 1,4-dioxane). Compounds of Formula (I) in which $R^9$ represents a phenyl or an heteroaryl substituted with a di-substituted amine, can be prepared from an intermediate of Formula (VIII) and an di-substituted amine, using a catalyst (such as XantPhos Pd G3) in the presence of a base, such as Cs$_2$CO$_3$, in a suitable solvent (for example, 1,4-dioxane). Compounds of Formula (I), including pharmaceutically acceptable salts thereof, in which $R^9$ represents a phenyl or an heteroaryl substituted with a di-substituted amine, can be prepared from an intermediate of Formula (VIII) and an di-substituted amine, using a catalyst (such as cupper(I) iodide (CuI) and a ligand such as 4,7-dimethoxy-1,10-phenanthroline) in the presence of a base. such as K$_3$PO$_4$, in a suitable solvent (for example, ethanol). Compounds of Formula (I), or a pharmaceutically acceptable salt thereof, in which $R^9$ represents a phenyl or an heteroaryl substituted with an optionally substituted monocyclic heteroaryl, can be prepared from an intermediate of Formula (VIII) and a boronic acid or boronic ester (for example, an optionally substituted monocyclic 4,4,5,5-tetramethyl-1,3,2-dioxaborolan-2-yl heteroaryl) using a catalyst, such as Pd(PPh$_3$)$_4$, in the presence of a base (such as Cs$_2$CO$_3$) in a suitable solvents, such as 1,4-dioxane/H$_2$O.

Scheme 7

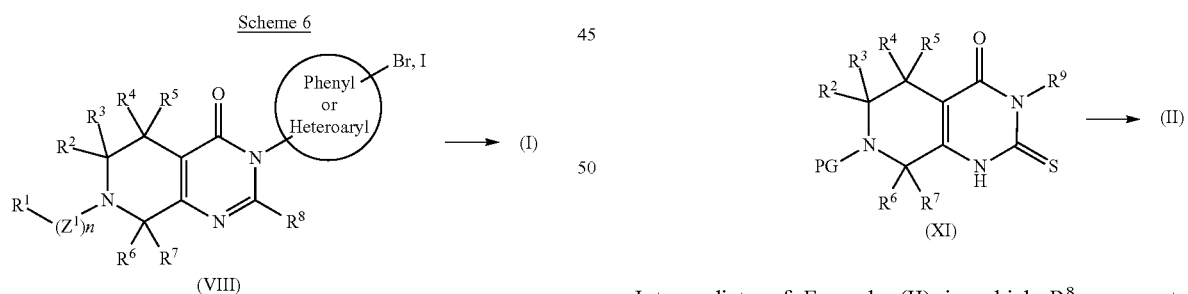

Intermediate of Formula (II) in which $R^8$ represents —SR$^{11}$ can be prepared from a compound of Formula (IX) using ammonium acetate in a suitable solvent (such as ethanol) to afford an intermediate of Formula (X). Treatment of the intermediate of Formula (X) with a strong base, such as NaH, in a suitable solvent (such as THF) followed by the subsequent addition of an isothiocyanate of general formula R$^9$—NCS can give an intermediate of Formula (XI). The intermediate of Formula (XI) can be subsequently alkylated with an iodo intermediate of general formula I-R$^{11}$ in the presence of a base (such as DBU) in a suitable solvent (such as DMF) to afford a compound of Formula (II) in which $R^8$ represents —SR$^{111}$.

Scheme 8

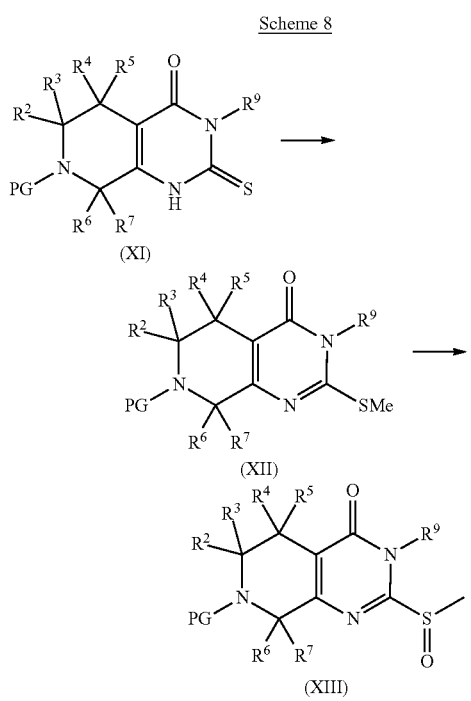

Intermediate of Formula (II) in which R⁸ represents —NR$^{14A}$R$^{14B}$ can be prepared from a compound of Formula (XI) using methyl iodide or methyl bromide, in the presence of a base, such as DBU, in a suitable solvent, such as DMF, to afford an intermediate of Formula (XII). Oxidation of an intermediate of Formula (XII) to a sulfoxide intermediate of Formula (XIII) can be achieved by a treatment with an oxidative agent (such as m-CPBA) in the presence of MgSO$_4$ and NaOAc in a suitable solvent (such as dichloromethane). Treatment of intermediate of Formula (XIII) with an amine of general formula HNR$^{14A}$R$^{14B}$ in the presence of a base (such as DIPEA) in the presence of a catalyst (for example, DMAP) in a suitable solvent (such as 1,4-dioxane) can afford an intermediate of Formula (II) in which R⁸ represents —NR$^{14A}$R$^{14B}$.

Scheme 9

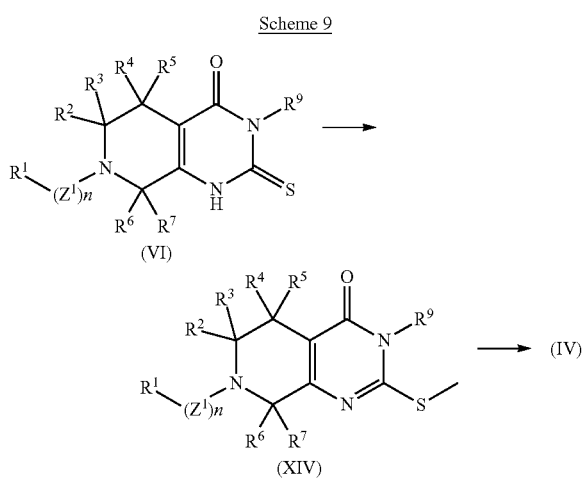

Intermediates of Formula (IV) in which the leaving group LG represents a methylsulfoxide can be prepared from an intermediate of Formula (VI) using methyl iodide or methyl bromide, in the presence of a base (for example, DBU) in a suitable solvent, such as DMF, to afford an intermediate of Formula (XIV). Oxidation of an intermediate of Formula (XIV) to a sulfoxide intermediate of Formula (IV) can be achieved using an oxidative agent, such as m-CPBA, in the presence of MgSO$_4$ and NaOAc in a suitable solvent, such as dichloromethane.

Scheme 10

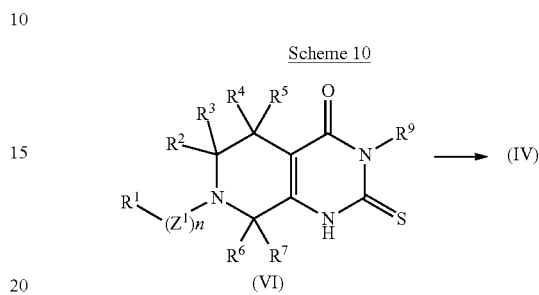

Intermediates of Formula (IV) in which the leaving group LG represents a chloro can be prepared from an intermediate of Formula (VI) using thiophosgene in a suitable solvent (such as 1,4-dioxane).

Scheme 11

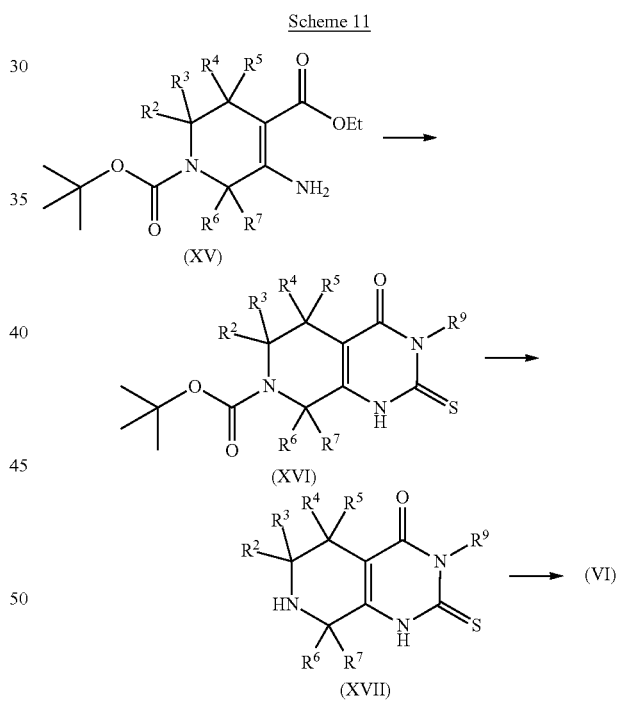

Intermediate of Formula (VI) can be prepared from an intermediate of Formula (XV) in the presence of a strong base, such as NaH, in a suitable solvent (for example, THF or 2-methylTHF) followed by the subsequent addition of an isothiocyanate of general formula R⁹—NCS to afford an intermediate of Formula (XVI). The Boc group of an intermediate of Formula (XVI) can be obtained in the presence of an acid (such as HCl or TFA) in a suitable solvent (for example, 1,4-dioxane) to afford an intermediate of Formula (XVII). Intermediates of Formula (VI) can be prepared from an intermediate of Formula (XVII) following several conditions known to those skilled in the art. For example, compounds of Formula (XVII), wherein $Z^1$ represents —NH—C(=O)— and n=1, can be obtained by reacting a compound of Formula (XVII) with a phenyl carbamate of general formula $R^1$—NH—C(=O)—O— phenyl or with an isocyanate of general formula $R^1$—N=C=O, in the presence of a suitable base in a suitable solvent. An example of a suitable base is triethylamine and an example of suitable solvent is acetonitrile or dichloromethane.

Further compounds of Formula (VI) wherein $Z^1$ represents —C(=O)— and n=1, can be obtained by reacting a compound of Formula (XVII) with an acyl chloride of general formula $R^1$—C(=O)—Cl in the presence of a base in a suitable solvent, including those bases and solvents described herein and/or known to those skilled in the art. Compounds of Formula (VI), wherein $Z^1$ represents —C(=O)— and n=1, can be obtained by reacting compound of Formula (XVII) with an carboxylic acid of general formula $R^1$—C(=O)—OH in the presence of an amide coupling agent (such as HATU) in a suitable solvent. Additional compounds of Formula (VI) can be prepared from a compound of Formula (XVII) using methods known in the art.

Intermediates of Formula (XX) can be prepared from an intermediate of Formula (XI) in the presence of ammonium acetate, in a suitable solvent (such as ethanol). Intermediate of Formula (VI) can be prepared from an intermediate of Formula (XX) in the presence of a strong base (for example, NaH) in a suitable solvent (such as THF or 2-methylTHF) followed by the addition of an isothiocyanate of general formula $R^9$—NCS. An intermediate of Formula (XX) can be treated with thiophosgene/NMM in a suitable solvent, such as dichloromethane, to afford an intermediate isothiocyanate, which can be converted to an intermediate of Formula (VI) by using an amine of general formula $NH_2$—$R^9$, in the presence of a base, such as triethylamine, in a suitable solvent (such as acetonitrile).

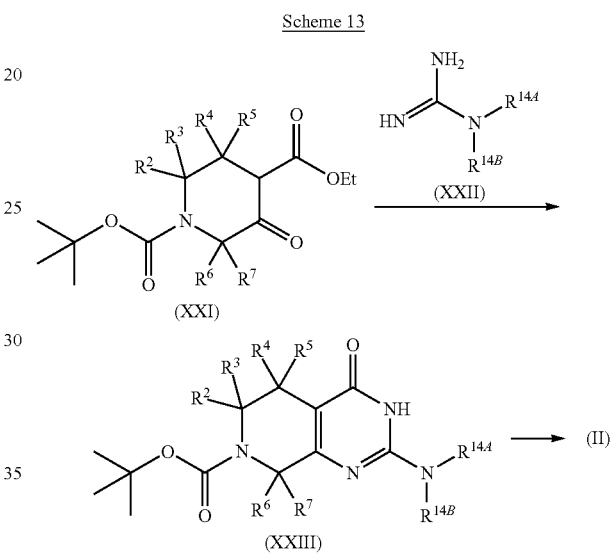

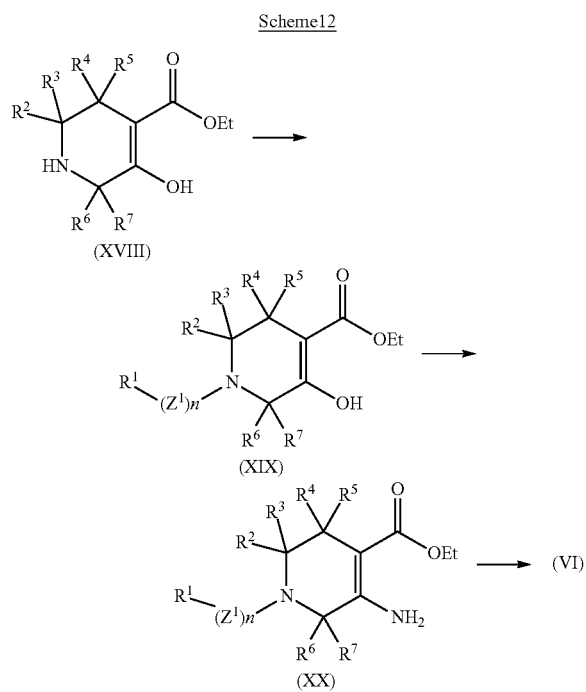

An intermediate of Formula (VI) can be prepared from an intermediate of Formula (XVIII) following other conditions known in the art, similar to the conditions used to convert an intermediate of Formula (XVII) to an intermediate for Formula (VI). For example, intermediates of Formula (XIX) wherein $Z^1$ represents —C(=O)— and n=1, can be obtained by reacting a compound of Formula (XVIII) with an acyl chloride of general formula $R^1$—C(=O)—Cl in the presence of a base in a suitable solvent. Additional compounds of Formula (XIX), wherein $Z^1$ represents —C(=O)— and n=1, can be obtained by reacting compound of Formula (XVIII) with an carboxylic acid of general formula $R^1$—C(=O)—OH in the presence of an amide coupling agent (such as HATU) in a suitable solvent. Suitable solvents are known to those skilled in the art and/or described herein.

Intermediates of Formula (II) in which $R^8$ represents —$NR^{14A}R^{14B}$ and the protecting group PG represents Boc, can be prepared from an intermediate of Formula (XXI) using a guanidine derivative of Formula (XXII), in the presence of a base, such as DBU, in a suitable solvent (such as acetonitrile) to afford an intermediate of Formula (XXIII). An intermediate of Formula (XXIII) can be converted in the intermediate of Formula (II) using methods known in the art. As an example, an intermediate of formula (XXIII) can be reacted with an aryl or heteroaryl boronic acid of general formula $R^9$—$B(OH)_2$, in the presence of TMEDA and $Cu(OAc)_2$ to afford an intermediate of Formula (II) in which $R^9$ represents a substituted phenyl, a substituted monocyclic heteroaryl or a substituted fused-bicyclic heteroaryl.

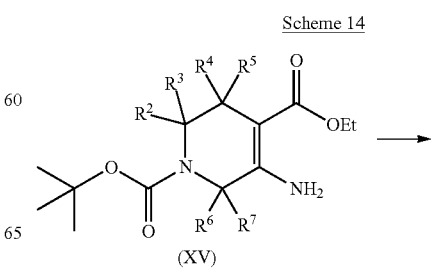

-continued

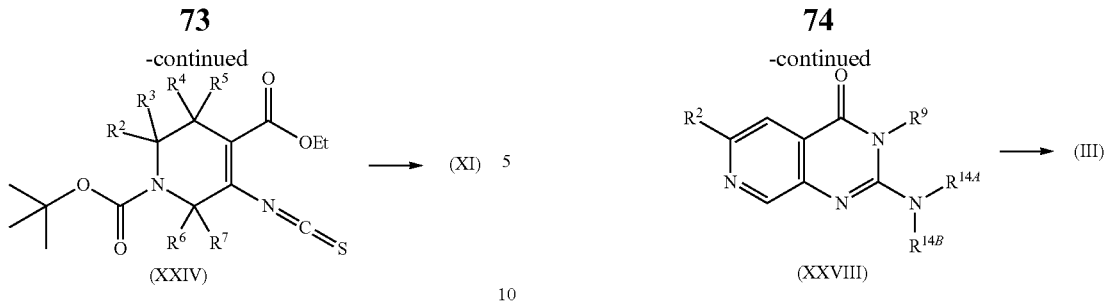

Intermediates of Formula (XI) can be obtained from an intermediate of Formula (XV) using methods known in the art, for example by treating an intermediate of Formula (XV) with thiophosgene and NMM in a suitable solvent (such as dichloromethane). Treatment of an intermediate of Formula (XXIV) with an amine of general formula R$^9$—NH$_2$ affords an intermediate of Formula (XI) in which PG represents a Boc group.

Scheme 15

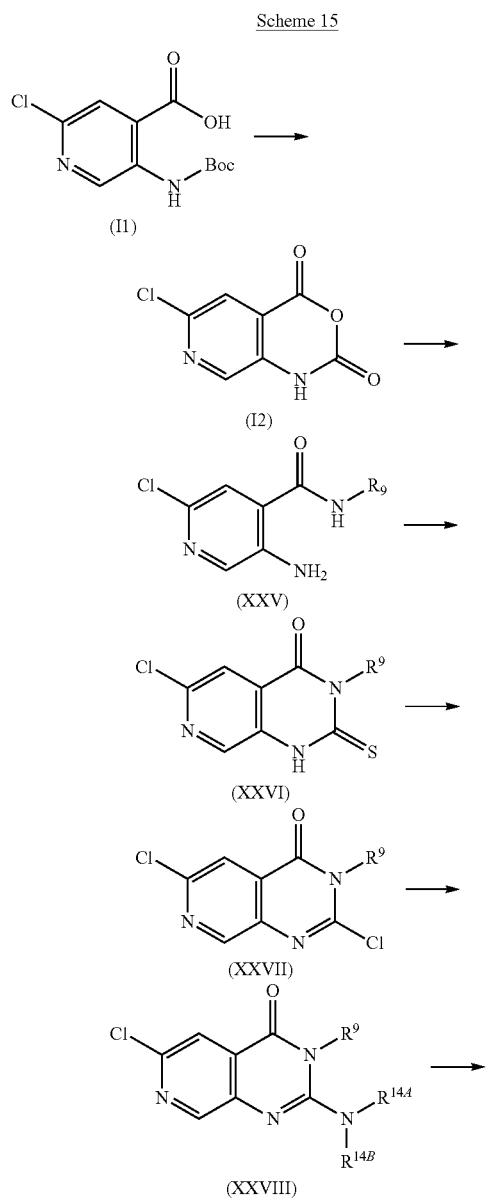

Intermediates of Formula (III) in which R$^3$, R$^4$, R$^5$, R$^6$ and R$^7$ each represent hydrogen, and in which R$^8$ represents —NR$^{14A}$R$^{14B}$, can be prepared from a chloro-N-Boc-aminopyridinecarboxylic acid intermediate of Formula (I1) using a base (such as triethylamine) in the presence of 2-chloro-N-methylpyridinium iodide in a suitable solvent (for example, acetonitrile) to afford an intermediate of Formula (I2). An intermediate of Formula (I2) can be converted to an intermediate of Formula (XXV) using an amine of general formula R$^9$—NH$_2$, in a suitable solvent (for example, acetic acid). Reaction of an intermediate of Formula (XXV) with CDI in DMF can afford the thio intermediate of Formula (XXVI), which can be converted in an intermediate of Formula (XXVII) using thiophosgene in a suitable solvent (such as 1,4-dioxane). Treatment of an intermediate of Formula (XXVII) with an amine of general formula NR$^{14A}$R$^{14B}$ can afford an intermediate of Formula (XXVIII). An intermediate of Formula (XXVIII) can be reacted with an organometallic derivative (such as a tin derivative of general formula R$^2$—Sn(n-Bu)$_3$). An intermediate of Formula (XXVIII) can be converted to an intermediates of Formula (III) in which R$^3$, R$^4$, R$^5$, R$^6$ and R$^7$ each can be hydrogen, and in which R$^8$ represents —NR$^{14A}$R$^{14B}$, by hydrogenation using H$_2$ in the presence of a catalyst (such as Pt/C) in a mixture of solvents (for example, acetic acid/THF/ethanol). In the instance where R$^2$ can be an unsaturated group, such as an alkene, the R$^2$ can be converted to another R$^2$ group, such as an alkyl, by hydrogenation.

Scheme 15

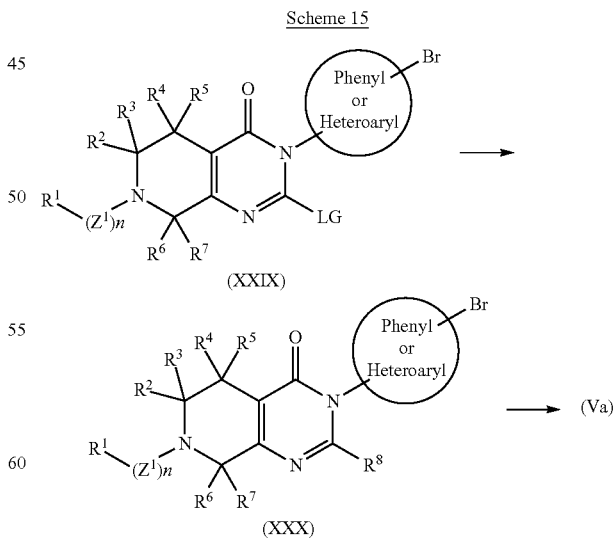

Intermediates of Formula (Va), in which R$^8$ represents —NR$^{14A}$R$^{14B}$, can be prepared from an intermediate of Formula (XXIX), in which LG represents a leaving group (such as sulfhydryl, methylsulfoxide or halo, in particular chloro or bromo). Intermediates of Formula (XXIX) can be reacted with an amine of general formula $HNR^{14A}R^{14B}$, in the presence of a base (for example, triethylamine) in a suitable solvent, such as acetonitrile, to afford an intermediate of Formula (XXX). The conversion of a bromo intermediate of Formula (XXX) to a boronic ester intermediate of Formula (Va) can be achieved using bis(pinacolato) diboron in the presence of a catalyst (such as $Pd(dppf)Cl_2$) in the presence of a base, such as KOAc, in a suitable solvent (for example, 1,4-dioxane). An intermediate of Formula (XXX) in which $R^8$ represents $—OR^{10}$, can be prepared by reacting an intermediate of Formula (XXIX) with an alcohol of general formula $HOR^{10}$, which can then be converted in an intermediate of Formula (Va) in which $R^8$ represents $—OR^{10}$, using bis(pinacolato)diboron in the presence of a catalyst (such as $Pd(dppf)Cl_2$) in the presence of a base (for example, KOAc) in a suitable solvent, such as 1,4-dioxane.

Scheme 16

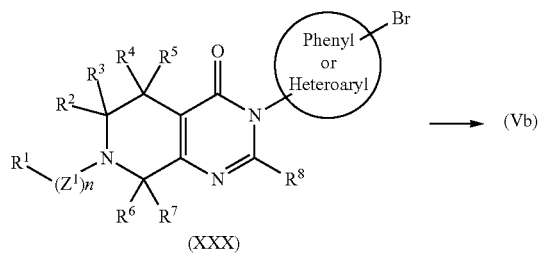

(XXX)

Intermediates of Formula (Vb) can be prepared from an intermediate of Formula (XXX) using bis(pinacolato)diboron, in the presence of a base (such as potassium acetate and 1,1'-bis(diphenylphosphino)ferrocene-palladium(II)dichloride dichloromethane complex) in a suitable solvent, such as 1,4-dioxane, to obtain an intermediate of Formula (Vb).

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a HBV and/or HDV infection.

Some embodiments disclosed herein relate to a method of treating a HBV and/or HDV infection that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of HBV and/or HDV. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of HBV and/or HDV.

In some embodiments, the HBV infection can be an acute HBV infection. In some embodiments, the HBV infection can be a chronic HBV infection.

Some embodiments disclosed herein relate to a method of treating liver cirrhosis that is developed because of a HBV and/or HDV infection that can include administering to a subject suffering from liver cirrhosis and/or contacting a cell infected with the HBV and/or HDV in a subject suffering from liver cirrhosis with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cirrhosis with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cirrhosis.

Some embodiments disclosed herein relate to a method of treating liver cancer (such as hepatocellular carcinoma) that is developed because of a HBV and/or HDV infection that can include administering to a subject suffering from the liver cancer and/or contacting a cell infected with the HBV and/or HDV in a subject suffering from the liver cancer with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cancer (such as hepatocellular carcinoma). Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cancer (such as hepatocellular carcinoma).

Some embodiments disclosed herein relate to a method of treating liver failure that is developed because of a HBV and/or HDV infection that can include administering to a subject suffering from liver failure and/or contacting a cell infected with the HBV and/or HDV in a subject suffering from liver failure with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver failure. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver failure.

Various indicators for determining the effectiveness of a method for treating an HBV and/or HDV infection are also known to those skilled in the art. Examples of suitable indicators include, but are not limited to, a reduction in viral load indicated by reduction in HBV DNA (or load) (e.g., reduction<$10^5$ copies/mL in serum), HBV surface antigen (HBsAg) and HBV e-antigen (HBeAg), a reduction in plasma viral load, a reduction in viral replication, a reduction in time to seroconversion (virus undetectable in patient serum), an increase in the rate of sustained viral response to therapy, an improvement in hepatic function, and/or a reduction of morbidity or mortality in clinical outcomes.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, an effective amount of a compound, or a pharmaceutically acceptable salt thereof, as described herein is an amount that is effective to achieve a sustained virologic response, for example, a sustained viral response 12 month after completion of treatment.

Subjects who are clinically diagnosed with a HBV and/or HDV infection include "naïve" subjects (e.g., subjects not previously treated for HBV and/or HDV) and subjects who have failed prior treatment for HBV and/or HDV ("treatment failure" subjects). Treatment failure subjects include "non-responders" (subjects who did not achieve sufficient reduction in ALT (alanine aminotransferase) levels, for example, subject who failed to achieve more than 1 log 10 decrease from base-line within 6 months of starting an anti-HBV and/or anti-HDV therapy) and "relapsers" (subjects who were previously treated for HBV and/or HDV whose ALT levels have increased, for example, ALT>twice the upper normal limit and detectable serum HBV DNA by hybridization assays). Further examples of subjects include subjects with a HBV and/or HDV infection who are asymptomatic.

In some embodiments, a compound, or a pharmaceutically acceptable salt thereof, as described herein can be provided to a treatment failure subject suffering from HBV and/or HDV. In some embodiments, a compound, or a pharmaceutically acceptable salt thereof, as described herein can be provided to a non-responder subject suffering from HBV and/or HDV. In some embodiments, a compound, or a pharmaceutically acceptable salt thereof, as described herein can be provided to a relapser subject suffering from HBV and/or HDV. In some embodiments, the subject can have HBeAg positive chronic hepatitis B. In some embodiments, the subject can have HBeAg negative chronic hepatitis B. In some embodiments, the subject can have liver cirrhosis. In some embodiments, the subject can be asymptomatic, for example, the subject can be infected with HBV and/or HDV but does not exhibit any symptoms of the viral infection. In some embodiments, the subject can be immunocompromised. In some embodiments, the subject can be undergoing chemotherapy.

Examples of agents that have been used to treat HBV and/or HDV include immunomodulating agents, and nucleosides/nucleotides. Examples of immunomodulating agents include interferons (such as IFN-α and pegylated interferons that include PEG-IFN-αX-2a); and examples of nucleosides/nucleotides include lamivudine, telbivudine, adefovir dipivoxil, clevudine, entecavir, tenofovir alafenamide and tenofovir disoproxil. However, some of the drawbacks associated with interferon treatment are the adverse side effects, the need for subcutaneous administration and high cost. Potential advantages of a compound of Formula (I), or a pharmaceutically acceptable salt of any of the foregoing, can be less adverse side effects, delay in the onset of an adverse side effect and/or reduction in the severity of an adverse side effect. A drawback with nucleoside/nucleotide treatment can be the development of resistance, including cross-resistance.

Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with an HBV and/or HDV strain that is resistant to one or more anti-HBV and/or anti-HDV agents. Examples of anti-viral agents wherein resistance can develop include lamivudine, telbivudine, adefovir dipivoxil, clevudine, entecavir, tenofovir alafenamide and tenofovir disoproxil. In some embodiments, development of resistant HBV and/or HDV strains is delayed when a subject is treated with a compound, or a pharmaceutically acceptable salt thereof, as described herein compared to the development of HBV and/or HDV strains resistant to other HBV and/or HDV anti-viral agents, such as those described.

Combination Therapies

In some embodiments, a compound, or a pharmaceutically acceptable salt thereof, as described herein can be used in combination with one or more additional agent(s) for treating and/or inhibiting replication HBV and/or HDV. Additional agents include, but are not limited to, an interferon, nucleoside/nucleotide analogs, a sequence specific oligonucleotide (such as anti-sense oligonucleotide and siRNA), nucleic acid polymers (NAPs, such as nucleic acid polymers that reduce HBsAg levels including STOPS™ compounds) an entry inhibitor and/or a small molecule immunomodulator. Examples of additional agents include recombinant interferon alpha 2b, IFN-α, PEG-IFN-α-2a, lamivudine, telbivudine, adefovir dipivoxil, clevudine, entecavir, tenofovir a lafenamide and tenofovir disoproxil. Examples of NAPs include, but are not limited to, REP 2139, REP 2165 and those STOPS™ compounds described in U.S. 2020/0147124 A1, which is hereby incorporated by reference for the purpose of describing the STOPS™ compounds provided therein, such as modified oligonucleotides identified as Nos. 1-392.

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Table of Abbreviations

| Abbreviation | Meaning |
| --- | --- |
| EtOAc, or EA | Ethyl Acetate |
| CyH | Cyclohexane |
| DCM | dichloromethane |
| d | Day(s) |
| ACN or MeCN | acetonitrile |
| AcOH | Acetic acid |
| rt | Room temperature |
| h | Hour(s) |
| min | Minute(s) |
| PE | petroleum ether |
| MeOH | methanol |
| SFC | Supercritical fluid chromatography |

Example 1

Compound 1

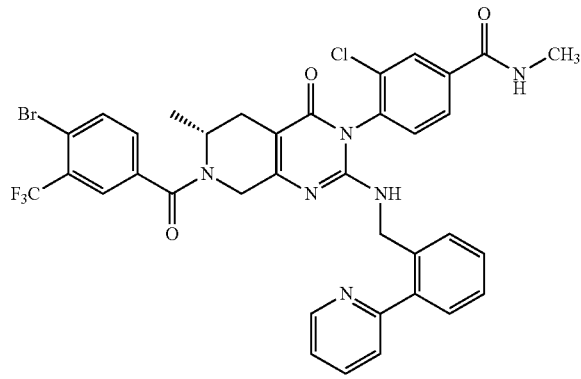 [SMILES: CNC(=O)c1ccc(-n2c(NCc3ccccc3-c3ccccn3)nc3c(c2=O)C[C@@H](C)N(C(=O)c2ccc(Br)c(C(F)(F)F)c2)C3)c(Cl)c1]

To a mixture of ethyl 4-oxopentanoate (120 g, 832.351 mmol) and (S)-α-phenylethylamine (100.87 g, 832.377 mmol) in DCE (2 L) was added Na(CH₃COO)₃BH (264.61 g, 1248.526 mmol). The mixture was stirred at rt for 16 h. Ethyl glyoxylate (169.95 g, 1664.702 mmol) was added, followed by Na(CH₃COO)₃BH (264.61 g, 1248.526 mmol). The mixture was stirred at rt for 2 days. The reaction was quenched with NaHCO₃ until pH 7 at rt. The layers were separated, and the aqueous layer was extracted with DCM (2×800 mL). The organic extracts were combined and concentrated under vacuum to afford ethyl 4-[(2-ethoxy-2-oxoethyl)[(1S)-1-phenylethyl]amino]pentanoate (150 g, 48.35%) as a colorless oil.

t-BuOK (125.44 g, 1117.922 mmol) was added to a solution of ethyl 4-[(2-ethoxy-2-oxoethyl)[(1S)-1-phenylethyl]amino]pentanoate (150 g, 447.169 mmol) in toluene (1.2 L). The mixture was stirred at rt for 30 min, then quenched with NH₄Cl (1 L) and stirred 15 min. The layers were separated. The aqueous layer was extracted with DCM (500 mL×2). The mixture was concentrated under vacuum. The residue was purified by silica gel column chromatography, eluted with PE:EA (100:0 to 97.5:2.5) to afford ethyl (2R)-5-hydroxy-2-methyl-1-[(1S)-1-phenylethyl]-3,6-dihydro-2H-pyridine-4-carboxylate (9 g, 6.26%) as a colorless oil.

To a solution of ethyl (2R)-5-hydroxy-2-methyl-1-[(1S)-1-phenylethyl]-3,6-dihydro-2H-pyridine-4-carboxylate (5 g, 17.279 mmol) in EtOH (130 mL, 2237.760 mmol) was added Pd(OH)₂/C (1.21 g, 1.728 mmol, wet: 20%) under N₂. The mixture was hydrogenated at rt for 40 min under H₂ atmosphere using a hydrogen balloon, filtered through packed Celite and concentrated under reduced pressure to afford ethyl (2R)-5-hydroxy-2-methyl-1,2,3,6-tetrahydropyridine-4-carboxylate (3.0 g, 94%) as a white solid.

To a stirred mixture of ethyl (2R)-5-hydroxy-2-methyl-1,2,3,6-tetrahydropyridine-4-carboxylate (4.0 g, 21.596 mmol) in DCM (80 mL, 1258.404 mmol) was added 4-bromo-3-(trifluoromethyl)benzoyl chloride (5.0 g) dropwise at 0° C. The mixture was stirred overnight at rt and then concentrated under reduced pressure. EtOH (50 mL) was added at rt. The aqueous layer was extracted with DCM (50 mL×2). The organic layers were combined and dried over sodium sulfate. The solids were removed by filtration, and the filtrate was concentrated under reduced pressure. The residue was purified by silica gel column chromatography, using a PE:EA gradient (100:0 to 75:25) to afford ethyl (2R)-1-[4-bromo-3-(trifluoromethyl)benzoyl]-5-hydroxy-2-methyl-3,6-dihydro-2H-pyridine-4-carboxylate (5.0 g, 53%) as a light yellow oil.

A mixture of ethyl (2R)-1-[4-bromo-3-(trifluoromethyl)benzoyl]-5-hydroxy-2-methyl-3,6-dihydro-2H-pyridine-4-carboxylate (5.0 g, 11.462 mmol) and NH₄OAc (4.42 g, 57.310 mmol) in ethanol (40 mL) stirred for 2 h at 50° C. After cooling to rt, the mixture was concentrated under reduced pressure and then diluted with 2-MeTHF (50 mL) and Na₂CO₃ (sat., aq., 50 mL). The layers were separated. The aqueous phase was extracted with 2-MeTHF (50 mL). The combined organic extracts were concentrated under reduced pressure. The crude product was purified by silica gel column chromatography, eluted with PE:EA (100:0 to 70:30) to afford ethyl (2R)-5-amino-1-[4-bromo-3-(trifluoromethyl)benzoyl]-2-methyl-3,6-dihydro-2H-pyridine-4-carboxylate (4.7 g, 94%) as a yellow oil.

To a stirred mixture of ethyl (2R)-5-amino-1-[4-bromo-3-(trifluoromethyl)benzoyl]-2-methyl-3,6-dihydro-2H-pyridine-4-carboxylate (4.7 g, 10.799 mmol) and NMM (1.64 g, 16.198 mmol) in DCM (40 mL) was added thiophosgene (1.55 g, 13.499 mmol) dropwise at 0° C. The mixture was stirred for 8 h at rt and then concentrated under reduced pressure. The residue was purified by silica gel column chromatography, eluted with PE:EA (100:0 to 75:25) to afford ethyl (2R)-1-[4-bromo-3-(trifluoromethyl)benzoyl]-5-isothiocyanato-2-methyl-3,6-dihydro-2H-pyridine-4-carboxylate (4.1 g, 72%) as a yellow solid.

To a stirred mixture of ethyl (2R)-1-[4-bromo-3-(trifluoromethyl)benzoyl]-5-isothiocyanato-2-methyl-3,6-dihydro-2H-pyridine-4-carboxylate (4.1 g, 8.590 mmol) in CH₃CN (25 mL) was added 4-amino-3-chloro-N-methylbenzamide (2.06 g, 11.167 mmol) and Et₃N (1.30 g, 12.885 mmol). The mixture was stirred at 95° C. for 12 h. The residue was purified by silica gel column chromatography, eluted with PE:EA (90:10 to 55:45) to afford 4-[(6R)-7-[4-bromo-3-(trifluoromethyl)benzoyl]-6-methyl-4-oxo-2-sulfanylidene-1H,5H,6H,8H-pyrido[3,4-d]pyrimidin-3-yl]-3-chloro-N-methylbenzamide (1.8 g, 31%) as a yellow solid.

To a stirred mixture of 4-[(6R)-7-[4-bromo-3-(trifluoromethyl)benzoyl]-6-methyl-4-oxo-2-sulfanylidene-1H,5H,6H,8H-pyrido[3,4-d]pyrimidin-3-yl]-3-chloro-N-methylbenzamide (1.8 g, 2.923 mmol) in dioxane (25 mL) was added thiophosgene (0.34 g, 2.923 mmol). The mixture was stirred 1 h at 80° C. The residue was purified by silica gel column chromatography, eluted with PE:EA (100:0 to 65:35) to afford 4-[(6R)-7-[4-bromo-3-(trifluoromethyl)benzoyl]-2-chloro-6-methyl-4-oxo-5H,6H,8H-pyrido[3,4-d]pyrimidin-3-yl]-3-chloro-N-methylbenzamide (1.05 g, 52%) as a light yellow solid.

A mixture of 2-{[(t-butoxycarbonyl)amino]methyl}phenylboronic acid (8 g, 31.861 mmol), 2-bromopyridine (6.04 g, 38.233 mmol), K₂CO₃ (8.81 g, 63.722 mmol) and Pd(dppf)Cl₂ (2.33 g, 3.186 mmol) in 1,4-dioxane/H₂O (5/1, 120 mL) was stirred for 5 h at 110° C. under a nitrogen atmosphere. The mixture cooled to rt. The mixture was diluted with water (100 mL) and then extracted with EtOAc (3×100 mL). The combined organic layers were concentrated under reduced pressure. The residue was purified by silica gel column chromatography, eluted with PE:EA (1:1) to afford t-butyl 2-(pyridin-2-yl)benzylcarbamate (9.0 g, 99%) as a yellow solid.

Into a solution of t-butyl 2-(pyridin-2-yl)benzylcarbamate (2 g) in DCM (20 mL) was added TFA (4 mL). The mixture was stirred for 30 min at rt. The mixture was then concentrated under reduced pressure to afford 1-[2-(pyridin-2-yl)

phenyl]methanamine trifluoroacetate (1.5 g) that was used in the next step without further purification.

Into a mixture of 4-[(6R)-7-[4-bromo-3-(trifluoromethyl)benzoyl]-2-chloro-6-methyl-4-oxo-5H,6H,8H-pyrido[3,4-d]pyrimidin-3-yl]-3-chloro-N-methylbenzamide (400 mg, 0.647 mmol) in CH₃CN (6 mL, 114.148 mmol) was added 1-[2-(pyridin-2-yl)phenyl]methanamine-trifluoroacetate (143.05 mg, 0.776 mmol) and K₂CO₃ (268.26 mg, 1.941 mmol). The crude product was purified by prep-HPLC under the following conditions (column: xBridge Shield RP18 OBD, 30×150 mm, 5 um; Mobile Phase A: water 10 mmol/L NH₄HCO₃+0.1% NH₃·H₂O, Mobile Phase B: ACN; flow rate 60 mL/min; gradient: 53% B to 70% B in 10 min, Wave Length 254 nm; Rt: 4.47 min). The mixture was separated by SFC and resulted in two atropisomers of 4-[(6R)-7-[4-bromo-3-(trifluoromethyl)benzoyl]-6-methyl-4-oxo-2-({[2-(pyridin-2-yl)phenyl]methyl}amino)-5H,6H,8H-pyrido[3,4-d]pyrimidin-3-yl]-3-chloro-N-methylbenzamide.

The first eluting isomer (1a) was isolated as a white solid (176.7 mg, 35.6%). LC-MS (ESI, m/z): 765[M+H]⁺. ¹H NMR (400 MHz, Methanol-d₄) δ 8.06 (d, J=1.9 Hz, 1H), 8.03-7.99 (m, 1H), 7.99-7.90 (m, 2H), 7.88 (d, J=2.0 Hz, 2H), 7.68-7.20 (m, 8H), 5.16 (d, J=75.3 Hz, 1H), 4.62-3.88 (m, 4H), 2.93 (s, 3H), 2.66 (d, J=16.2 Hz, 1H), 2.48 (s, 1H), 1.33 (d, J=54.6 Hz, 3H). The second eluting isomer (1b) isolated as a white solid (16.1 mg, 3.1%).

Example 2

Compound 2

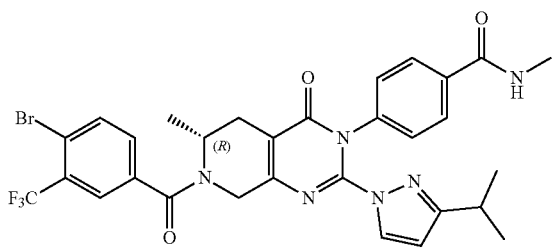

To a solution of oxalyl dichloride (181 g, 1.43 mol, 124 mL) in DCM (1500 mL) at −65° C. was added DMSO (111 mL) in DCM (500 mL). After stirring for 1 h, t-butyl (R)-(1-hydroxypropan-2-yl)carbamate (250 g, 1.43 mol) in DCM (500 mL) was added dropwise. After stirring for 2 h, Et₃N (144 g, 1.43 mol, 198 mL) was added dropwise, and the mixture was warmed to 25° C. gradually. The mixture was stirred at 25° C. for 4 h. The reaction was quenched by the addition of NH₄Cl (sat., aq., 2.5 L), and then extracted with DCM (2×2.5 L). The combined organic layers were dried over Na₂SO₄. The solids were removed by filtration and the filtrate was concentrated under reduced pressure to afford t-butyl (R)-(1-oxopropan-2-yl)carbamate (450 g, 2.60 mol, 91.0% yield, crude) as a colorless oil, which was used in the next step without further purification.

To a solution of t-butyl (R)-(1-oxopropan-2-yl)carbamate (225 g, 1.30 mol) in DCM (2.25 L) was added (carbethoxymethylene)triphenylphosphorane (429 g, 1.23 mol). The mixture was stirred at 25° C. for 12 h. The mixture was concentrated under reduced pressure to give the crude product, purified by silica gel column chromatography (PE:EA=15:1 to 5:1) to afford ethyl (R)-4-((t-butoxycarbonyl)amino)pent-2-enoate (500 g, 2.06 mol, 79.1% yield) as a colorless oil. ¹HNMR (400 MHz, CDCl₃) δ 6.86 (dd, J=15.76, 4.88 Hz, 1H) 5.89 (dd, J=15.70, 1.56 Hz, 1H) 4.58 (br s, 1H) 4.39 (br s, 1H) 4.18 (q, J=7.13 Hz, 2H) 1.44 (s, 9H) 1.24-1.29 (m, 6H).

To a solution of ethyl (R)-4-((t-butoxycarbonyl)amino)pent-2-enoate (125 g, 513 mmol) in CH₃OH (1.25 L) was added 10% Pd/C (6.00 g) and Pd(OH)₂ (6.06 g) under N₂. The suspension was degassed under vacuum and purged with H₂ (1.04 g, 514 mmol) several times. The mixture was stirred under H₂ (50 psi) at 50° C. for 12 h. The solids were removed by filtration under N₂, and the filtrate was evaporated to dryness to afford a colorless oil, ethyl (R)-4-((t-butoxycarbonyl)amino)pentanoate (480 g, 1.96 mol, 95% yield) was obtained as a colorless oil. ¹HNMR (400 MHz, CDCl₃) δ 4.29-4.45 (m, 1H) 4.13 (q, J=7.13 Hz, 2H) 3.57-3.75 (m, 1H) 2.35 (t, J=7.69 Hz, 2H) 1.66-1.84 (m, 3H) 1.43 (s, 9H) 1.25 (t, J=7.13 Hz, 3H) 1.14 (d, J=6.50 Hz, 3H).

A solution of ethyl (R)-4-((t-butoxycarbonyl)amino)pentanoate (480 g, 1.96 mol) in HCl/EA (2.5 L) was stirred at 25° C. for 2 h. The mixture was concentrated under reduced pressure to afford ethyl (R)-4-aminopentanoate HCl (450 g, crude) as a yellow oil, which was used directly in the next step without purification.

To a mixture of ethyl (R)-4-aminopentanoate HCl (225 g, 1.24 mol) in THF (4 L) and H₂O (1 L), was added K₂CO₃ (427 g, 3.10 mol) at 25° C. After addition, the yellow solution was stirred at 25° C. for 30 min. A solution of ethyl 2-bromoacetate (206 g, 1.24 mol, 137 mL) was added dropwise into the reaction system at 25° C. over 30 min. The yellow solution was stirred at 25° C. for 11 h. Ethyl (R)-4-((2-ethoxy-2-oxoethyl)amino)pentanoate (400 g, 1.73 mol, 70% yield, crude) was obtained as a colorless oil, which was used in the next step without work up or purification.

A solution of (Boc)₂O (189 g, 865 mmol, 199 mL) was added dropwise into ethyl (R)-4-((2-ethoxy-2-oxoethyl)amino)pentanoate (200 g, 865 mmol) over 30 min. The yellow solution was stirred for 6 h at 25° C. The solution was pumped onto a filter, and the filter cake was washed with EA (1 L). The filtrate was collected and H₂O (3 L) was added. The mixture was extracted with EA (2×5 L). The combined organic layers were washed with brine (2 L), dried over Na₂SO₄, and the solids were removed by filtration and the filtrate was concentrated under reduced pressure to afford ethyl (R)-4-((t-butoxycarbonyl)(2-ethoxy-2-oxoethyl)amino)pentanoate (400 g, 1.21 mol, 70% yield, crude) as a yellow oil, which used in the next step without purification. ¹HNMR (400 MHz, CDCl₃) δ 4.06-4.22 (m, 4H) 3.54-3.93 (m, 2H) 2.26-2.55 (m, 2H) 1.71 (qd, J=7.48, 3.69 Hz, 2H) 1.45-1.55 (m, 6H) 1.42 (s, 4H) 1.22-1.35 (m, 6H).

To a mixture of ethyl (R)-4-((t-butoxycarbonyl)(2-ethoxy-2-oxoethyl)amino)pentanoate (200 g, 603 mmol) in THF (2 L) was added t-BuOK (135 g, 1.21 mol) at 0° C. under N₂. The yellow mixture was stirred at 25° C. for 12 h under N₂. The reaction was quenched with aq. citric acid (250 g in 3 L of H₂O) below 10° C., then extracted with EA (3×2.5 L). The combined organic layers were washed with brine (2 L), dried over Na₂SO₄. The solids were removed by filtration and the filtrate was concentrated under reduced pressure. The crude product was purified by silica column chromatography (PE:EA=15:1 to 10:1) to afford 1-(t-butyl) 4-ethyl 5-oxo-2-(R)-methyl-3,6-dihydropyridine-1,4(2H)-dicarboxylate (210 g, 736 mmol, 61% yield) as a yellow oil. ¹H NMR (400 MHz, CDCl₃) δ 12.06 (s, 1H) 4.54 (br s, 1H) 4.33 (br d, J=19.39 Hz, 1H) 4.23 (dtt, J=10.62, 7.07, 7.07, 3.63, 3.63 Hz, 2H) 3.64 (br d, J=19.26 Hz, 1H) 2.45-2.55 (m, 1H) 2.18 (d, J=15.63 Hz, 1H) 1.47 (s, 9H) 1.31 (t, J=7.13 Hz, 3H) 1.11 (d, J=6.88 Hz, 3H).

To a solution of 1-(t-butyl) 4-ethyl 5-oxo-2-(R)-methyl-3,6-dihydropyridine-1,4(2H)-dicarboxylate (210 g, 736 mmol) in EA (1 L) was added a solution of HCl/EA (4 M, 2 L) dropwise at 25° C. The mixture was stirred at 25° C. for 3 h, and then concentrated under reduced pressure. The crude product was triturated with EA (500 mL) at 25° C. for 30 min to afford ethyl (R)-5-hydroxy-2-methyl-1,2,3,6-tetrahydropyridine-4-carboxylate HCl (140 g, 631 mmol, 85.9% yield, 100% purity) as a white solid. $^1$H NMR (400 MHz, Methanol-$d_4$) δ 4.29 (q, J=6.96 Hz, 2H) 3.92-4.01 (m, 1H) 3.77-3.87 (m, 1H) 3.42-3.54 (m, 1H) 2.66-2.76 (m, 1H) 2.23-2.39 (m, 1H) 1.43 (d, J=6.50 Hz, 3H) 1.32 (t, J=7.07 Hz, 3H).

A solution of ethyl (R)-5-hydroxy-2-methyl-1,2,3,6-tetrahydropyridine-4-carboxylate HCl (115 g, 519 mmol) in DMF (1 L) was cooled to 0° C. DIPEA (268 g, 2.08 mol, 361 mL) and $T_3P$ (495 g, 778 mmol, 463 mL, 50.0% purity) were added. The mixture was stirred at 25° C. for 12 h. The reaction was quenched with water (2 L) at 25° C. The mixture was diluted with EA (1.5 L) and then extracted with EA (3×1 L). The combined organic layers were washed with brine (500 mL), dried over $Na_2SO_4$. The solids were removed by filtration and the filtrate was concentrated under reduced pressure. The crude product was purified by silica gel chromatography (eluent of 0 to 10% EA:PE gradient) to afford ethyl (R)-1-(4-bromo-3-(trifluoromethyl)benzoyl)-5-hydroxy-2-methyl-1,2,3,6-tetrahydropyridine-4-carboxylate (130 g, 259 mmol, 50% yield, 87% purity) as a yellow oil. $^1$H NMR: ($CDCl_3$) δ 12.10 (br s, 1H) 7.80 (d, J=8.13 Hz, 1H) 7.74 (d, J=1.88 Hz, 1H) 7.42 (dd, J=8.13, 1.88 Hz, 1H) 4.64-5.30 (m, 1H) 4.19-4.34 (m, 2H) 4.08-4.17 (m, 1H) 3.81 (br dd, J=12.13, 2.75 Hz, 1H) 2.58 (br d, J=14.76 Hz, 1H) 2.24 (br d, J=16.01 Hz, 1H) 1.32 (t, J=7.13 Hz, 3H) 1.25 (br t, J=3.13 Hz, 3H).

To a solution of ethyl (R)-1-(4-bromo-3-(trifluoromethyl)benzoyl)-5-hydroxy-2-methyl-1,2,3,6-tetrahydropyridine-4-carboxylate (90.0 g, 206 mmol) in EtOH (900 mL) was added $NH_4OAc$ (79.5 g, 1.03 mol). The mixture was stirred at 60° C. for 2 h. The mixture was concentrated under reduced pressure to remove EtOH. The residue was diluted with water (200 mL) and extracted with EA (3×200 mL). The combined organic layers were washed with brine (200 mL), dried over $Na_2SO_4$. The solids were removed by filtration and the filtrate was concentrated under reduced pressure. The crude product was purified by silica gel chromatography (eluent of 0 to 50% EA:PE gradient) to afford ethyl (R)-5-amino-1-(4-bromo-3-(trifluoromethyl)benzoyl)-2-methyl-1,2,3,6-tetrahydropyridine-4-carboxylate (55.0 g, 125 mmol, 60.7% yield, 99.1% purity) as a yellow solid. $^1$H-NMR (DMSO-$d_6$, 400 MHz) δ 7.98 (d, J=8.13 Hz, 1H) 7.84 (d, J=1.75 Hz, 1H) 7.63 (dd, J=8.19, 1.56 Hz, 1H) 6.74-7.47 (m, 2H) 4.63-4.91 (m, 1H) 4.00-4.08 (m, 2H) 3.80-3.95 (m, 1H) 3.59-3.75 (m, 1H) 2.45 (br d, J=5.75 Hz, 1H) 2.14 (br d, J=1.25 Hz, 1H) 1.06-1.20 (m, 6H).

To a solution of ethyl (R)-5-amino-1-(4-bromo-3-(trifluoromethyl)benzoyl)-2-methyl-1,2,3,6-tetrahydropyridine-4-carboxylate (100 g, 230 mmol) and NMM (102 g, 1.01 mol, 111 mL) in $CH_2Cl_2$ (1 L) was added $SCCl_2$ (55.5 g, 483 mmol, 37.0 mL) at 0° C. The mixture was stirred at 0° C. for 1 h. The reaction was quenched with ice-water (100 mL) at 0° C. The mixture was diluted with $CH_2Cl_2$ (150 mL) and extracted with $CH_2Cl_2$ (3×500 mL). The combined organic layers were washed with brine (500 mL) and dried over $Na_2SO_4$. The solids were removed by filtration and the filtrate was concentrated under reduced pressure. The crude product was purified by silica gel chromatography (0 to 20% EA:PE gradient) to afford ethyl (R)-1-(4-bromo-3-(trifluoromethyl)benzoyl)-5-isothiocyanato-2-methyl-1,2,3,6-tetrahydropyridine-4-carboxylate (100 g, 163 mmol, 71.0% yield, 77.9% purity) as a yellow oil. $^1$H-NMR ($CDCl_3$, 400 MHz) δ 7.74 (d, J=8.13 Hz, 1H) 7.66 (d, J=1.75 Hz, 1H) 7.34 (dd, J=8.13, 2.00 Hz, 1H) 4.55-5.18 (m, 1H) 4.14-4.26 (m, 3H) 3.67-3.85 (m, 2H) 2.51-2.70 (m, 1H) 2.31-2.47 (m, 1H) 1.29 (t, J=7.13 Hz, 3H) 1.18 (dd, J=7.00, 3.38 Hz, 4H).

To a solution of ethyl (R)-1-(4-bromo-3-(trifluoromethyl)benzoyl)-5-isothiocyanato-2-methyl-1,2,3,6-tetrahydropyridine-4-carboxylate (100 g, 210 mmol) in $CH_3CN$ (1 L) was added 4-amino-N-methylbenzamide (31.5 g, 210 mmol) and $Et_3N$ (53.0 g, 524 mmol, 72.9 mL). The mixture was stirred at 95° C. for 12 h to obtain a yellow suspension. The mixture was concentrated under reduced pressure. The crude product was triturated with EA (500 mL) at 25° C. for 1 h to afford (R)-4-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-N-methylbenzamide (80.0 g, 119 mmol, 57% yield, 86% purity) as a white solid. $^1$H-NMR (DMSO-$d_6$, 400 MHz) δ 8.49-8.57 (m, 1H) 8.02 (br d, J=7.63 Hz, 1H) 7.88 (br d, J=8.76 Hz, 3H) 7.69 (br d, J=7.63 Hz, 1H) 7.29 (br d, J=8.88 Hz, 1H) 7.25 (br s, 1H) 5.08-5.27 (m, 1H) 4.18-4.35 (m, 1H) 4.05-4.14 (m, 1H) 2.80 (d, J=4.50 Hz, 3H) 2.53-2.62 (m, 1H) 2.17-2.36 (m, 1H) 1.18-1.20 (m, 3H).

To a solution of (R)-4-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-N-methylbenzamide (80.0 g, 138 mmol) in dioxane (880 mL) was added $SCCl_2$ (31.6 g, 275 mmol, 21.1 mL). The mixture was stirred at 100° C. for 2 h. The mixture was concentrated under reduced pressure. The residue was purified by silica gel chromatography (eluent of 0-80% EA:PE gradient) to afford 4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide (49.0 g, 81.5 mmol, 59.2% yield, 97.1% purity) as an off-white solid. $^1$H-NMR ($CD_3OD$, 400 MHz) δ 7.94-8.03 (m, 3H) 7.90 (d, J=1.75 Hz, 1H) 7.61-7.68 (m, 1H) 7.42-7.54 (m, 2H) 5.02-5.49 (m, 1H) 4.13-4.56 (m, 2H) 2.95 (s, 3H) 2.72-2.86 (m, 1H) 2.56 (br d, J=17.89 Hz, 1H) 1.24-1.38 (m, 3H).

3-(propan-2-yl)-1H-pyrazole (226.44 mg, 0.23 mL, 2.056 mmol) was added to a solution of 4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide (400 mg, 0.69 mmol) in anhydrous acetonitrile (6.4 mL). The mixture was stirred at 130° C. under $N_2$ for 16 h. After cooling to rt, the mixture was diluted with sat. aq. $NaHCO_3$ and then extracted with EA (3×). The combined organic layers were washed with water (2×) and brine (2×) and dried over $Na_2SO_4$. The solids were removed by filtration and the filtrate was evaporated to dryness. The crude mixture was purified by chromatography on silica gel to afford (R)-4-(7-(4-bromo-3-(trifluoromethyl)benzoyl)-2-(3-isopropyl-1H-pyrazol-1-yl)-6-methyl-4-oxo-5,6,7,8-tetrahydropyrido[3,4-d]pyrimidin-3(4H)-yl)-N-methylbenzamide (248 mg, 55%) as a white powder. $^1$H-NMR (DMSO-$d_6$, 600 MHz, 80° C.) δ 0.89 (m, 6H), 1.26 (m, 3H), 2.56 (m, 1H), 2.57-2.62 (m, 1H), 2.72-2.76 (m, 1H), 2.80 (d, J=4.5 Hz, 3H), 4.25-4.28 (m, 1H), 4.59-4.76 (m, 2H), 6.17 (d, J=2.5 Hz, 1H), 7.26 (d, J=8.0 Hz, 2H), 7.70 (d, J=8.4 Hz, 1H), 7.80 (d, J=8.4 Hz, 2H), 7.88 (s, 1H), 8.00 (d, J=8.4 Hz, 1H), 8.03 (d, J=1.8 Hz, 1H), 8.19 (d, J=3.6 Hz, 1H) ppm. LC-MS: $C_{30}H_{28}BrF_3N_6O_3$ $[M+H]^+$: 657/659.

Example 3

Compound 3

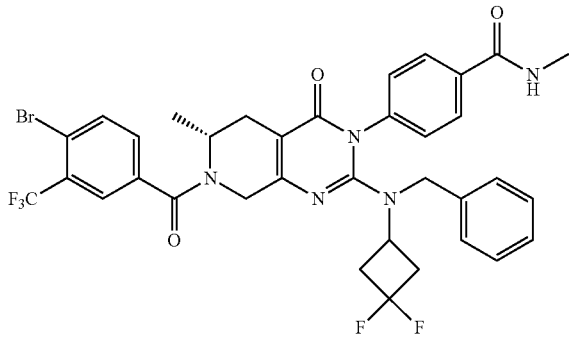 [SMILES: CNC(=O)c1ccc(-n2c(N(Cc3ccccc3)C3CC(F)(F)C3)nc3c(c2=O)C[C@@H](C)N(C(=O)c2ccc(Br)c(C(F)(F)F)c2)C3)cc1]

DIPEA (1.42 mL, 8.56 mmol) was added to a mixture of 4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide (500 mg, 0.86 mmol) and N-benzyl-3,3-difluorocyclobutan-1-amine HCl (1.0 g, 4.28 mmol) in anhydrous MeCN (8.6 mL) under N₂. The mixture was stirred at 170° C. for 22 h. Additional N-benzyl-3,3-difluorocyclobutan-1-amine HCl (1.0 g, 4.28 mmol) and DIPEA (2.12 mL, 12.85 mmol) were added. The mixture was stirred at 170° C. for 23 h. After cooling to rt, the mixture was diluted with EA, washed with sat. aq. NH₄Cl (5×) and brine and dried over Na₂SO₄. The solids were removed by filtration and the filtrate was evaporated to dryness. The crude mixture was purified by chromatography on silica gel (0% to 5% CH₃OH in DCM) to afford (R)-4-(2-(benzyl(3,3-difluorocyclobutyl)amino)-7-(4-bromo-3-(trifluoromethyl)benzoyl)-6-methyl-4-oxo-5,6,7,8-tetrahydropyrido[3,4-d]pyrimidin-3(4H)-yl)-N-methylbenzamide (97 mg, 15%) as a yellow solid. $^1$H-NMR (DMSO-d₆, 600 MHz, 80° C.) δ 1.20 (d, J=6.8 Hz, 3H), 2.41 (d, J=17.0 Hz, 1H), 2.52-2.66 (m, 5H), 2.85 (d, J=4.6 Hz, 3H), 3.63-3.70 (m, 1H), 3.86 (d, J=15.3 Hz, 1H), 3.91 (d, J=15.3 Hz, 1H), 4.03-4.10 (m, 1H), 4.54 (br s, 2H), 6.93-6.97 (m, 2H), 7.12-7.26 (m, 3H), 7.48 (d, J=8.4 Hz, 2H), 7.66 (m, 1H), 7.85 (d, J=1.6 Hz, 1H), 7.94-8.00 (m, 3H), 8.29-8.33 (m, 1H) ppm. LCMS: $C_{35}H_{31}BrF_5N_5O_3$ [M+H]⁺: 744/746.

Example 4

Compound 4

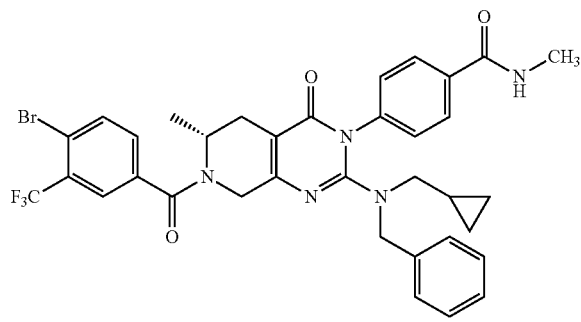 [SMILES: CNC(=O)c1ccc(-n2c(N(Cc3ccccc3)CC3CC3)nc3c(c2=O)C[C@@H](C)N(C(=O)c2ccc(Br)c(C(F)(F)F)c2)C3)cc1]

Triethylamine (0.67 mL, 4.8 mmol) was added to a solution of 4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide (400 mg, 0.69 mmol) and benzyl(cyclopropylmethyl)amine (331.45 mg, 2.056 mmol) in anhydrous acetonitrile (12 mL) under N₂. The mixture was stirred at 110° C. for 20 h. After cooling to rt, the mixture was diluted with water and extracted with EA (3×). The combined organic phases were washed with water (2×) and brine (2×) and dried over Na₂SO₄. The solids were removed by filtration and the filtrate was evaporated to dryness. The crude mixture was purified by silica column chromatography (0% to 10% CH₃OH in DCM, then 0% to 100% EA in CyH) to afford (R)-4-(2-(benzyl(cyclopropylmethyl)amino)-7-(4-bromo-3-(trifluoromethyl)benzoyl)-6-methyl-4-oxo-5,6,7,8-tetrahydropyrido[3,4-d]pyrimidin-3(4H)-yl)-N-methylbenzamide (112 mg, 23%) as a white solid. $^1$H-NMR (DMSO-d₆, 600 MHz, 80° C.) δ -0.08--0.01 (m, 2H), 0.31-0.39 (m, 2H), 0.69-0.77 (m, 1H), 1.21 (d, J=6.8 Hz, 3H), 2.34-2.42 (m, 1H), 2.58-2.65 (m, 1H), 2.77 (d, J=6.8 Hz, 2H), 2.84 (d, J=4.6 Hz, 3H), 4.07-4.17 (m, 1H), 4.24 (d, J=14.9 Hz, 1H), 4.32 (d, J=14.9 Hz, 1H), 4.38-4.84 (m, 2H), 7.09 (d, J=7.3 Hz, 2H), 7.18-7.30 (m, 3H), 7.39 (d, J=8.1 Hz, 2H), 7.68 (d, J=8.1 Hz, 1H), 7.87 (s, 1H), 7.94 (d, J=8.3 Hz, 2H), 7.99 (d, J=8.3 Hz, 1H), 8.28 (br s, 1H) ppm. LC-MS: $C_{35}H_{33}BrF_3N_5O_3$ [M+H]⁺: 708/710.

Example 5

Compound 5

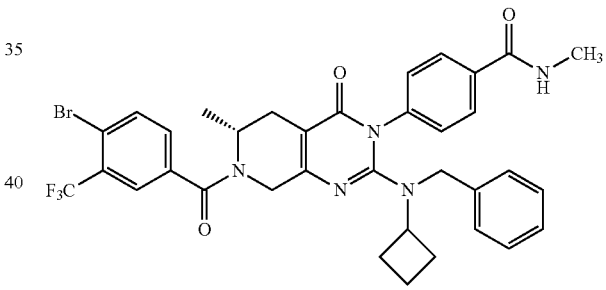

DIPEA (3.77 mL, 22.82 mmol) and N-cyclobutylbenzenemethanamine (883 mg, 5.48 mmol) were added to a solution of 4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide (533 mg, 0.91 mmol) in anhydrous MeCN (11 mL) under N₂. The mixture was stirred at 170° C. for 24 h. After cooling to rt, the mixture was diluted with water and extracted with EA (3×). The combined organic phases were washed with water (2×) and brine (2×) and dried over Na₂SO₄. The solids were removed by filtration and the filtrate was evaporated to dryness. The crude mixture was purified by chromatography on silica gel (0% to 10% CH₃OH in DCM then 0% to 100% EA in CyH). The resulting solid was dissolved in EA, washed with aq. HCl 1N (3×) and water (20 mL) and dried over Na₂SO₄. The solids were removed by filtration and the filtrate was evaporated to dryness to afford (R)-4-(2-(benzyl(cyclobutyl)amino)-7-(4-bromo-3-(trifluoromethyl)benzoyl)-6-methyl-4-oxo-5,6,7,8-tetrahydropyrido[3,4-d]pyrimidin-3(4H)-yl)-N-methylbenzamide (125 mg, 19%) as a white solid. $^1$H-NMR (DMSO-d₆, 600 MHz, 80° C.) δ 1.18 (d, J=6.8 Hz, 3H), 1.35-1.44 (m, 1H), 1.48-1.58 (m, 1H), 1.63-1.70 (m, 1H), 1.78-2.00 (m, 3H), 2.32-2.42 (m, 1H), 2.55-2.64 (m, 1H), 2.84 (d, J=4.6 Hz, 3H), 3.76-3.87 (m, 1H), 3.96-4.16 (m, 3H), 4.51 (br s, 2H), 7.05 (d, J=7.3 Hz, 2H), 7.18-7.30 (m, 3H), 7.35 (d, J=8.1 Hz, 2H), 7.66 (d, J=8.1 Hz, 1H), 7.86 (s, 1H), 7.94 (d, J=8.3 Hz, 2H), 7.98 (d, J=8.3 Hz, 1H), 8.30 (br s, 1H) ppm. LC-MS: $C_{35}H_{33}BrF_3N_5O_3$ [M+H]+: 708/710.

Example 6

Compound 6

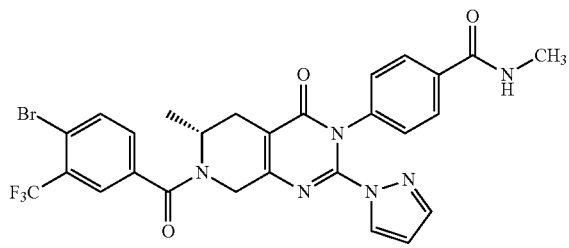 [SMILES: CNC(=O)c1ccc(-n2c(-n3cccn3)nc3c(c2=O)C[C@@H](C)N(C(=O)c2ccc(Br)c(C(F)(F)F)c2)C3)cc1]

A solution of (R)-4-(7-(4-bromo-3-(trifluoromethyl)benzoyl)-2-chloro-6-methyl-4-oxo-5,6,7,8-tetrahydropyrido[3,4-d]pyrimidin-3(4H)-yl)-N-methylbenzamide (400 mg, 0.69 mmol) and pyrazole (140 mg, 2.06 mmol) in anhydrous MeCN (6.4 mL) was stirred at 130° C. for 5 h under $N_2$. After cooling to rt, the mixture was diluted with EA, washed with sat. aq. $NaHCO_3$ and brine (2×) and dried over $Na_2SO_4$. The solids were removed by filtration and the filtrate was evaporated to dryness to give the crude product, purified by chromatography on silica gel (0% to 5% MeOH in DCM) to give (R)-4-(7-(4-bromo-3-(trifluoromethyl)benzoyl)-6-methyl-4-oxo-2-(1H-pyrazol-1-yl)-5,6,7,8-tetrahydropyrido[3,4-d]pyrimidin-3(4H)-yl)-N-methylbenzamide (329 mg, 78%) as a white solid. $^1$H-NMR (DMSO-$d_6$, 400 MHz, 80° C.) δ 1.27 (d, J=6.9 Hz, 3H), 2.56 (m, 1H), 2.71-2.78 (m, 1H), 2.79 (d, J=4.6 Hz, 3H), 4.20-4.36 (m, 1H), 4.60 (br s, 1H), 4.76 (br s, 1H), 6.29-6.34 (m, 1H), 7.30 (d, J=8.2 Hz, 2H), 7.42 (d, J=1.6 Hz, 1H), 7.70 (dd, J=8.2, 2.1 Hz, 1H), 7.78 (d, J=8.7 Hz, 2H), 7.89 (d, J=2.1 Hz, 1H), 8.00 (d, J=8.2 Hz, 1H), 8.12 (d, J=2.7 Hz, 1H), 8.22-8.29 (m, 1H) ppm. LCMS: $C_{27}H_{22}BrF_3N_6O_3$ [M+H]+: 615/617.

Example 7

Compound 7

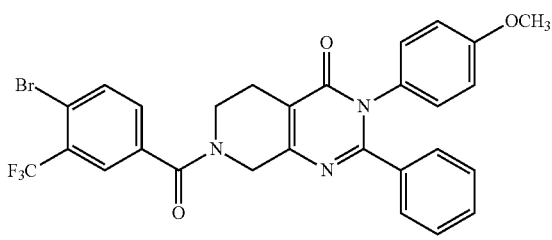 [SMILES: COc1ccc(-n2c(-c3ccccc3)nc3c(c2=O)CCN(C(=O)c2ccc(Br)c(C(F)(F)F)c2)C3)cc1]

$NH_4OAc$ (7.103 g, 92.14 mmol) was added to a solution of 1-t-butyl 4-ethyl 3-oxopiperidine-1,4-dicarboxylate (5 g, 18.43 mmol) in EtOH (60 mL) under $N_2$. The mixture was stirred at rt for 1 h and at 50° C. for 1 h. The mixture was evaporated to dryness. The residue was taken up into 2-MeTHF and washed with sat. aq. $K_2CO_3$. The organic layer was separated, and the aqueous phase was re-extracted with 2-MeTHF. The combined organic layers were dried over $MgSO_4$. The solids were removed by filtration and the filtrate was evaporated to dryness. The residue was triturated in cyclohexane to afford 1-(t-butyl) 4-ethyl 5-imino-3,6-dihydropyridine-1,4(2H)-dicarboxylate (4.02 g, 81%) as a white solid. $^1$H-NMR (DMSO-$d_6$, 300 MHz) δ 1.17 (t, J=7.2 Hz, 3H), 1.40 (s, 9H), 2.17-2.20 (m, 2H), 3.34-3.37 (m, 2H), 3.95 (s, 2H), 4.03 (q, J=7.2 Hz, 2H), 7.10 (br s, 2H) ppm.

Thiophosgene (2.18 mL, 24.36 mmol) was added dropwise at 0° C. to a solution of p-anisidine (2.5 g, 2.36 mL, 20.3 mmol) in anhydrous DCM (75 mL) under $N_2$. The mixture was stirred at rt for 4 h. The mixture was diluted with sat. aq. $K_2CO_3$ and extracted with DCM (3×). The combined organic phases were washed with water and brine and dried over $Na_2SO_4$. The solids were removed by filtration and the filtrate was evaporated to dryness to afford 1-isothiocyanato-4-methoxybenzene (3.3 g, 98%), which was used without purification in the next step. $^1$H-NMR (DMSO-$d_6$, 300 MHz) δ 3.77 (s, 3H), 6.98 (d, J=8.7 Hz, 2H), 7.39 (d, J=8.7 Hz, 2H) ppm.

NaH (0.89 g, 60%, 22.2 mmol) was added portionwise to a solution of 1-(t-butyl) 4-ethyl 5-imino-3,6-dihydropyridine-1,4(2H)-dicarboxylate (3 g, 11.10 mmol) in anhydrous THF (30 mL) at 0° C. under $N_2$. The mixture was stirred at rt for 15 min and then 1-isothiocyanato-4-methoxybenzene (2.38 g, 14.43 mmol) was added. The mixture was stirred at 50° C. for 4 h. After cooling to rt, the reaction was quenched with HCl 1M. The mixture was extracted with 2-MeTHF (2×). The combined organic layers were washed with sat. aq. $NaHCO_3$ (3×) and brine and dried over $MgSO_4$. The solids were removed by filtration and the filtrate was evaporated to dryness. The crude mixture was purified by chromatography on silica gel (0% to 100% EA in CyH) to afford t-butyl 3-(4-methoxyphenyl)-4-oxo-2-thioxo-2,3,4,5,6,8-hexahydropyrido[3,4-d]pyrimidine-7(1H)-carboxylate (1.4 g, 32%) as a yellow solid. $^1$H-NMR (DMSO-$d_6$, 300 MHz) δ 1.43 (s, 9H), 2.26-2.31 (m, 2H), 3.48-3.53 (m, 2H), 3.79 (s, 3H), 4.25 (br s, 2H), 6.96 (d, J=8.7 Hz, 2H), 7.03 (d, J=8.7 Hz, 2H) ppm. LCMS: $C_{19}H_{23}N_3O_4S$ [M+H]+: 390.

Thiophosgene (0.38 g, 0.25 mL, 2.82 mmol) was added to a solution of t-butyl 3-(4-methoxyphenyl)-4-oxo-2-thioxo-2,3,4,5,6,8-hexahydropyrido[3,4-d]pyrimidine-7(1H)-carboxylate (1.1 g, 2.82 mmol) in anhydrous dioxane (20 mL) under $N_2$. The mixture was stirred at rt for 30 min and then at 100° C. for 30 min. The mixture was evaporated to dryness and purified by chromatography on silica gel (0% to 10% MeOH in DCM) to afford t-butyl 2-chloro-3-(4-methoxyphenyl)-4-oxo-4,5,6,8-tetrahydropyrido[3,4-d]pyrimidine-7(3H)-carboxylate (523 mg, 47%) as a yellow solid. $^1$H-NMR (DMSO-$d_6$, 300 MHz) δ 1.43 (s, 9H), 2.39-2.46 (m, 2H), 3.52-3.57 (m, 2H), 3.81 (s, 3H), 4.29 (s, 2H), 7.06 (d, J=8.7 Hz, 2H), 7.32 (d, J=8.7 Hz, 2H) ppm. LCMS: $C_{19}H_{22}ClN_3O_4$[M+H]+: 392.

Pd(dppf)$Cl_2$·DCM (218 mg, 0.27 mmol) and phenylboronic acid (244 mg, 2.00 mmol) were added to a solution of t-butyl 2-chloro-3-(4-methoxyphenyl)-4-oxo-4,5,6,8-tetrahydropyrido[3,4-d]pyrimidine-7(3H)-carboxylate (523 mg, 1.33 mmol) in dioxane (8 mL) and $Na_2CO_3$ (2M, aq., 2.67 mL, 5.34 mmol). The mixture was stirred at 110° C. for 1 h. After cooling to rt, the mixture was diluted with EA and filtered through a pad of celite. The filtrate was washed with water (2×) and brine (2×) and dried over $MgSO_4$. The solids were removed by filtration and the filtrate was evaporated to dryness. The crude mixture was purified by chromatography on silica gel (0% to 100% EA in CyH) to afford t-butyl 3-(4-methoxyphenyl)-4-oxo-2-phenyl-4,5,6,8-tetrahydropyrido[3,4-d]pyrimidine-7(3H)-carboxylate (544 mg, 94%) as a brown oil. LCMS: $C_{25}H_{27}N_3O_4$ [M+H]+: 434.

HCl (4N in dioxane, 6.3 mL, 25.1 mmol) was added to a solution of t-butyl 3-(4-methoxyphenyl)-4-oxo-2-phenyl-4,5,6,8-tetrahydropyrido[3,4-d]pyrimidine-7(3H)-carboxylate (544 mg, 1.25 mmol) in anhydrous DCM (11 mL) under $N_2$. The mixture stirred at rt for 1 h, then evaporated to dryness to afford 3-(4-methoxyphenyl)-2-phenyl-5,6,7,8-tetrahydropyrido[3,4-d]pyrimidin-4(3H)-one (418 mg, 100%) as a beige solid, which was used without further purification in the next step. LCMS: $C_{20}H_{19}N_3O_2$ [M+H]+: 334.

DIPEA (0.62 mL, 3.75 mmol) and HATU (713 mg, 1.88 mmol) were added to a solution of 3-(4-methoxyphenyl)-2-phenyl-5,6,7,8-tetrahydropyrido[3,4-d]pyrimidin-4(3H)-one (418 mg, 1.25 mmol) and 4-bromo-3-(trifluoromethyl)benzoic acid (336 mg, 1.25 mmol) in anhydrous DMF (32 mL) under $N_2$. The mixture was stirred at rt for 1 h. The mixture was diluted with water and extracted with EA (3×). The combined organic phases were washed with water and brine and dried over $Na_2SO_4$. The solids were removed by filtration and the filtrate was evaporated to dryness under reduced pressure. The crude mixture was purified by chromatography on silica gel (0% to 10% MeOH in DCM then 50% to 100% EA in CyH) to afford 7-(4-bromo-3-(trifluoromethyl)benzoyl)-3-(4-methoxyphenyl)-2-phenyl-5,6,7,8-tetrahydropyrido[3,4-d]pyrimidin-4(3H)-one (290 mg, 40%) as a white powder. $^1$H-NMR (DMSO-$d_6$, 600 MHz, 80° C.): 2.61-2.62 (m, 2H), 3.72 (s, 3H), 3.74 (s, 2H), 4.53 (s, 2H), 6.83 (d, J=9.0 Hz, 2H), 7.10 (d, J=9.0 Hz, 2H), 7.22-7.28 (m, 5H), 7.71 (d, J=8.2 Hz, 1H), 7.90 (s, 1H), 7.98 (d, J=8.7 Hz, 1H) ppm. LCMS: $C_{28}H_{21}BrF_3N_3O_3$ [M+H]+: 584/586.

Example 8

Compound 8

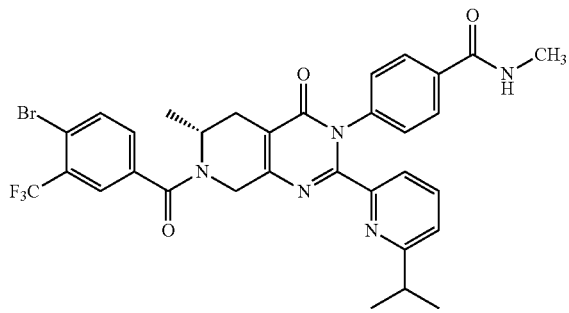 [SMILES: CNC(=O)c1ccc(-n2c(-c3cccc(C(C)C)n3)nc3c(c2=O)C[C@@H](C)N(C(=O)c2ccc(Br)c(C(F)(F)F)c2)C3)cc1]

NEt$_3$ (9.38 mL, 67.49 mmol) was added to a solution of ethyl (R)-5-hydroxy-2-methyl-1,2,3,6-tetrahydropyridine-4-carboxylate (5 g, 26.99 mmol) and Boc$_2$O (8.84 g, 40.49 mmol) in anhydrous THF (125 mL) at 0° C. under $N_2$. The mixture was stirred at rt for 2 h. The mixture was diluted with sat. aq. NH$_4$Cl and extracted with DCM (2×). The combined organic layers were washed with HCl (1M, aq.), sat. aq. NaHCO$_3$, water and brine and dried over $Na_2SO_4$. The solids were removed by filtration and the filtrate was evaporated to dryness. The crude mixture was purified by chromatography on silica gel (0 to 10% EA in CyH) to afford 1-(t-butyl) 4-ethyl 5-keto-2-(R)-methyl-3,6-dihydropyridine-1,4(2H)-dicarboxylate (7.70 g, 100%) as a colorless oil. LC-MS: $C_{14}H_{23}NO_5$ [M-tBu]+: 230.

NH$_4$OAc (10.4 g, 134.93 mmol) was added to a solution of 1-(t-butyl) 4-ethyl 5-keto-2-(R)-methyl-3,6-dihydropyridine-1,4(2H)-dicarboxylate (7.7 g, 26.99 mmol) in EtOH (88 mL) under $N_2$. The mixture was stirred at 60° C. for 1 h. and then evaporated to dryness. The residue was dissolved in EA, washed with sat. aq. NH$_4$Cl and brine and dried over $Na_2SO_4$. The solids were removed by filtration and the filtrate was evaporated to dryness to afford 1-(t-butyl) 4-ethyl 5-imino-2-(R)-methyl-3,6-dihydropyridine-1,4(2H)-dicarboxylate (7.7 g, 100%) as a yellow oil, which was used without further purification in the next step. $^1$H-NMR (DMSO-$d_6$, 400 MHz) δ 1.10 (d, J=6.8 Hz, 3H), 1.17 (t, J=7.2 Hz, 3H), 1.40 (s, 9H), 2.11-2.16 (m, 1H), 2.33-2.38 (m, 1H), 3.58 (d, J=18.0 Hz, 1H), 4.03 (q, J=6.8 Hz, 2H), 4.18 (d, J=18.0 Hz, 1H), 4.19-4.33 (m, 1H), 6.12 (m, 1H), 7.11 (m, 1H) ppm.

Thiophosgene (4.03 g, 2.67 mL, 29.79 mmol) was added to a solution of 1-(t-butyl) 4-ethyl 5-imino-2-(R)-methyl-3,6-dihydropyridine-1,4(2H)-dicarboxylate (7.7 g, 27.08 mmol) and N-methylmorpholine (5.48 g, 5.95 mL, 54.16 mmol) in anhydrous DCM (70 mL) at 0° C. under $N_2$. The mixture was stirred at rt for 3 h. The mixture was diluted with sat. aq. Na$_2$CO$_3$ and extracted with DCM (2×). The combined organic layers were washed with brine and dried over $Na_2SO_4$. The solids were removed by filtration and the filtrate was evaporated to dryness. The crude mixture was purified by chromatography on silica gel (0% to 1% MeOH in DCM) to give (2R)-1,4(2H)-pyridinedicarboxylic acid, 3,6-dihydro-5-isothiocyanato-2-methyl-, 1-(1,1-dimethylethyl) 4-ethyl ester (5.5 g, 62%) as an orange oil. LCMS: $C_{15}H_{22}N_2O_4S$ [M-tBu]+: 271.

NEt$_3$ (3.51 mL, 25.27 mmol) was added to a solution of (2R)-1,4(2H)-pyridinedicarboxylic acid, 3,6-dihydro-5-isothiocyanato-2-methyl-, 1-(1,1-dimethylethyl) 4-ethyl ester (5.5 g, 16.85 mmol) and 4-amino-N-methylbenzamide (3.04 g, 20.22 mmol) in anhydrous CH$_3$CN (128 mL) under $N_2$. The mixture was stirred at 110° C. for 18 h. Additional NEt$_3$ (1.17 mL, 8.42 mmol) was added. The mixture was stirred at 110° C. for 1 h. The mixture was evaporated to dryness and purified by chromatography on silica gel (0% to 6% MeOH in DCM) to afford t-butyl (R)-6-methyl-3-(4-(methylcarbamoyl)phenyl)-4-oxo-2-thioxo-2,3,4,5,6,8-hexahydropyrido[3,4-d]pyrimidine-7(1H)-carboxylate (4.7 g, 65%) as a yellow solid. LCMS: $C_{21}H_{26}N_4O_4S$ [M+H]+: 431.

Thiophosgene (1.48 g, 0.98 mL, 10.92 mmol) was added to a solution of t-butyl (R)-6-methyl-3-(4-(methylcarbamoyl)phenyl)-4-oxo-2-thioxo-2,3,4,5,6,8-hexahydropyrido[3,4-d]pyrimidine-7(1H)-carboxylate (4.7 g, 10.92 mmol) in anhydrous dioxane (85 mL) under $N_2$. The mixture was stirred at rt for 30 min and at 100° C. for 30 min. The mixture was evaporated to dryness and purified by chromatography on silica gel (0% to 10% MeOH in DCM) to afford t-butyl (R)-2-chloro-6-methyl-3-(4-(methylcarbamoyl)phenyl)-4-oxo-4,5,6,8-tetrahydropyrido[3,4-d]pyrimidine-7(3H)-carboxylate (1.1 g, 23%) as a yellow solid. $^1$H-NMR (DMSO-$d_6$, 400 MHz): 1.08 (d, J=6.8 Hz, 3H), 1.44 (s, 9H), 2.38-2.50 (m, 1H), 2.81 (d, J=4.8 Hz, 3H), 3.95-4.15 (m, 2H), 4.47-4.67 (m, 2H), 7.51-7.57 (m, 2H), 7.76 (d, J=8.8 Hz, 2H), 8.57 (q, J=4.8 Hz, 1H) ppm. LCMS: $C_{21}H_{25}ClN_4O_4$ [M+H]+: 433.

t-BuLi (1.7 M in pentane, 3.23 mL, 5.5 mmol) was added dropwise to a solution of 2-bromo-6-(propan-2-yl)pyridine (500 mg, 2.5 mmol) in anhydrous THF (12 mL) under $N_2$ at −78° C. The mixture was stirred at −78° C. for 30 min. Chlorotributyltin (854 mg, 0.71 mL, 2.62 mmol) was added dropwise. The mixture was stirred at −78° C. for 1 h and at rt for 3 h. The mixture was hydrolyzed with sat. aq. NH₄Cl and extracted with EA. The organic phase was washed with sat. aq. NH₄Cl (2×) and brine and dried over Na₂SO₄. The solids were removed by filtration and the filtrate was evaporated to dryness to afford 2-isopropyl-6-(tributylstannyl)pyridine (1.02 g, 100%) as a colorless oil, which was used without further purification in the next step. LCMS: C₂₀H₃₇NSn [M+H]⁺: 412.

Bis(tri-t-butylphosphine)palladium(0) (5.90 mg, 0.012 mmol) was added to a mixture of t-butyl (R)-2-chloro-6-methyl-3-(4-(methylcarbamoyl)phenyl)-4-oxo-4,5,6,8-tetrahydropyrido[3,4-d]pyrimidine-7(3H)-carboxylate (50 mg, 0.12 mmol) and 2-isopropyl-6-(tributylstannyl)pyridine (95 mg, 0.23 mmol) in anhydrous DMF (1 mL) under N₂. The mixture was stirred at 100° C. for 3 h. After cooling to rt, the mixture was diluted with sat. aq. NaHCO₃ and extracted with EA. The organic layer was washed with water and brine and dried over Na₂SO₄. The solids were removed by filtration and the filtrate was evaporated to dryness. The crude mixture was purified by chromatography on silica gel (0 to 10% MeOH in DCM) to afford t-butyl (R)-2-(6-isopropylpyridin-2-yl)-6-methyl-3-(4-(methylcarbamoyl)phenyl)-4-oxo-4,5,6,8-tetrahydropyrido[3,4-d]pyrimidine-7(3H)-carboxylate (32 mg, 54%) as a beige solid. ¹H-NMR (DMSO-d₆, 400 MHz) δ0.83-0.87 (m, 6H), 1.12 (d, J=6.8 Hz, 3H), 1.45 (s, 9H), 2.54-2.67 (m, 2H), 2.74 (d, J=4.8 Hz, 3H), 4.04-4.10 (m, 1H), 4.56-4.70 (m, 2H), 7.14 (d, J=7.6 Hz, 1H), 7.17-7.22 (m, 1H), 7.31-7.34 (m, 1H), 7.59 (d, J=7.6 Hz, 1H), 7.66-7.77 (m, 3H), 8.39 (q, J=4.8 Hz, 1H) ppm. LCMS: C₂₉H₃₅N₅O₄ [M+H]⁺: 517.

A solution of t-butyl (R)-2-(6-isopropylpyridin-2-yl)-6-methyl-3-(4-(methylcarbamoyl)phenyl)-4-oxo-4,5,6,8-tetrahydropyrido[3,4-d]pyrimidine-7(3H)-carboxylate (96 mg, 0.19 mmol) in HCl 4N in dioxane (0.93 mL, 3.71 mmol) was stirred at rt under N₂ for 2 h. The mixture was evaporated to dryness to afford (R)-4-(2-(6-isopropylpyridin-2-yl)-6-methyl-4-oxo-5,6,7,8-tetrahydropyrido[3,4-d]pyrimidin-3(4H)-yl)-N-methylbenzamide (84 mg, 100%) as a beige solid, which was used without further purification in the next step. LCMS: C₂₄H₂₇N₅O₂ [M+H]⁺: 417.

4-bromo-3-(trifluoromethyl)benzoic acid (56 mg, 0.21 mmol), HATU (87 mg, 0.23 mmol) and DIPEA (0.16 mL, 0.95 mmol) were added to a solution of (R)-4-(2-(6-isopropylpyridin-2-yl)-6-methyl-4-oxo-5,6,7,8-tetrahydropyrido[3,4-d]pyrimidin-3(4H)-yl)-N-methylbenzamide (86 mg, 0.19 mmol) in anhydrous DMF (1.7 mL) under N₂. The mixture was stirred at rt for 1 h. The mixture was diluted with sat. aq. Na₂CO₃ and extracted with EA (3×). The combined organic phases were washed with water (3×) and brine (3×) and dried over Na₂SO₄. The solids were removed by filtration and the filtrate was evaporated to dryness. The crude mixture was purified by chromatography on silica gel (0% to 10% MeOH in DCM) to afford (R)-4-(7-(4-bromo-3-(trifluoromethyl)benzoyl)-2-(6-isopropylpyridin-2-yl)-6-methyl-4-oxo-5,6,7,8-tetrahydropyrido[3,4-d]pyrimidin-3(4H)-yl)-N-methylbenzamide (90 mg, 71%) as a beige solid. ¹H-NMR (DMSO-d₆, 400 MHz, 80° C.) δ0.86-0.94 (m, 6H), 1.28 (d, J=7.0 Hz, 3H), 2.53-2.61 (m, 1H), 2.68-2.81 (m, 5H), 4.31 (d, J=18.7 Hz, 1H), 4.45-4.98 (m, 2H), 7.13 (d, J=7.6 Hz, 1H), 7.17-7.31 (m, 2H), 7.57 (d, J=7.6 Hz, 1H), 7.67-7.77 (m, 4H), 7.89 (d, J=1.8 Hz, 1H), 8.00 (d, J=8.2 Hz, 1H), 8.11-8.22 (m, 1H) ppm. LC-MS: C₃₂H₂₉BrF₃N₅O₃ [M+H]⁺: 668/670.

Example 9

Compound 9

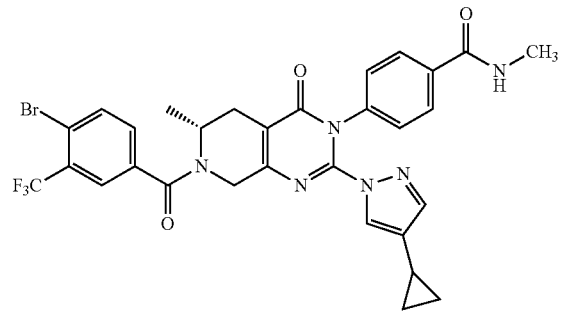 [SMILES: CNC(=O)c1ccc(-n2c(-n3cc(C4CC4)cn3)nc3c(c2=O)C[C@@H](C)N(C(=O)c2ccc(Br)c(C(F)(F)F)c2)C3)cc1]

A solution of (R)-4-(7-(4-bromo-3-(trifluoromethyl)benzoyl)-2-chloro-6-methyl-4-oxo-5,6,7,8-tetrahydropyrido[3,4-d]pyrimidin-3(4H)-yl)-N-methylbenzamide (300 mg, 0.51 mmol) and 4-cyclopropyl-1H-pyrazole (167 mg, 1.54 mmol) in anhydrous MeCN (5 mL) was stirred at 130° C. under N₂ for 2 h. After cooling to rt, the mixture was diluted with EA, washed with aq. sat. NaHCO₃ and brine (2×) and dried over Na₂SO₄. The solids were removed by filtration and the filtrate was evaporated to dryness. The crude mixture was purified by chromatography on silica gel (0% to 5% MeOH in DCM). The resulting solid was triturated in isopropanol to afford (R)-4-(7-(4-bromo-3-(trifluoromethyl)benzoyl)-2-(4-cyclopropyl-1H-pyrazol-1-yl)-6-methyl-4-oxo-5,6,7,8-tetrahydropyrido[3,4-d]pyrimidin-3(4H)-yl)-N-methylbenzamide (33 mg, 10%) as a white solid. ¹H-NMR (DMSO-d₆, 400 MHz, 80° C.) δ 0.42-0.46 (m, 2H), 0.77-0.81 (m, 2H), 1.25 (d, J=6.8 Hz, 1H), 1.60-1.67 (m, 1H), 2.52 (m, 1H), 2.70-2.76 (m, 1H), 2.80 (d, J=4.6 Hz, 3H), 4.22-4.29 (m, 2H), 4.60-4.73 (m, 2H), 7.24 (s, 1H), 7.28 (d, J=7.9 Hz, 2H), 7.70 (dd, J=8.2 Hz, 2.0 Hz, 2H), 7.79 (d, J=8.4 Hz, 2H), 7.88 (s, 2H), 8.00 (d, J=8.2 Hz, 1H), 8.25 (br s, 1H) ppm. LC-MS: C₃₀H₂₆BrF₃N₆O₃ [M+H]⁺: 655/657.

Example 10

Compound 10

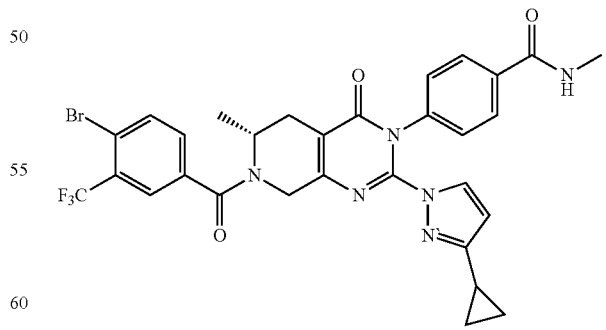

A solution of (R)-4-(7-(4-bromo-3-(trifluoromethyl)benzoyl)-2-chloro-6-methyl-4-oxo-5,6,7,8-tetrahydropyrido[3,4-d]pyrimidin-3(4H)-yl)-N-methylbenzamide (300 mg, 0.51 mmol) and 3-cyclopropyl-1H-pyrazole (167 mg, 1.54 mmol) in anhydrous MeCN (5 mL) was stirred at 130° C.

under N₂ for 2 d. After cooling to rt, the mixture was diluted with EA, washed with sat. aq. NaHCO₃ and brine and dried over Na₂SO₄. The solids were removed by filtration and the filtrate was evaporated to dryness. The crude mixture was purified by chromatography on silica gel (0% to 5% MeOH in DCM) to afford (R)-4-(7-(4-bromo-3-(trifluoromethyl)benzoyl)-2-(3-cyclopropyl-1H-pyrazol-1-yl)-6-methyl-4-oxo-5,6,7,8-tetrahydropyrido[3,4-d]pyrimidin-3(4H)-yl)-N-methylbenzamide (148 mg, 48%) as a white solid. ¹H-NMR (DMSO-d₆, 400 MHz, 80° C.) δ 0.21-0.36 (m, 2H), 0.60-0.73 (m, 2H), 1.25 (d, J=7.1 Hz, 3H), 1.55-1.67 (m, 1H), 2.53 (br s, 1H), 2.68-2.77 (m, 1H), 2.81 (d, J=4.6 Hz, 3H), 4.25 (d, J=20.1 Hz, 1H), 4.39-4.91 (m, 2H), 6.15 (d, J=2.6 Hz, 1H), 7.26 (d, J=7.8 Hz, 2H), 7.70 (dd, J=8.2 Hz, 1.8 Hz, 1H), 7.79-7.83 (m, 2H), 7.88 (d, J=1.5 Hz, 1H), 7.96-8.04 (m, 2H), 8.20-8.26 (m, 1H) ppm. LC-MS: C₃₀H₂₆BrF₃N₆O₃ [M+H]⁺: 655/657.

Example 11

Compounds 11a and 11b

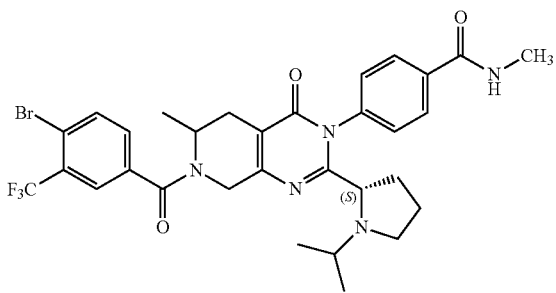

Triphenyl phosphite (22.5 g, 72.43 mmol) was added to a solution of 5-amino-2-chloropyridine-4-carboxylic acid (5 g, 28.97 mmol) and N-boc-L-proline (6.24 g, 28.97 mmol) in anhydrous pyridine (100 mL) under N₂. The mixture was stirred at 70° C. for 5 h. 4-amino-N-methylbenzamide (5.22 g, 34.77 mmol) was added. The mixture was stirred at 70° C. for 1 h. After cooling to rt, the mixture was diluted with water and extracted with EA (3×). The combined organic phases were washed with water, sat. aq. NaHCO₃ and brine and dried over MgSO₄. The solids were removed by filtration and the filtrate was evaporated to dryness. The crude mixture was purified by chromatography on silica gel (0% to 2% MeOH in DCM) to afford t-butyl (S)-2-(6-chloro-3-(4-(methylcarbamoyl)phenyl)-4-oxo-3,4-dihydropyrido[3,4-d]pyrimidin-2-yl)pyrrolidine-1-carboxylate (1.7 g, 12%) as a yellow solid. LC-MS: C₂₄H₂₆ClN₅O₄[M+H]⁺: 484.

Pd(dppf)Cl₂·DCM (0.29 g, 0.35 mmol), K₂CO₃ (1.46 g, 10.54 mmol) and trimethylboroxine 50% (4.41 g, 17.56 mmol) were added to a solution of t-butyl (S)-2-(6-chloro-3-(4-(methylcarbamoyl)phenyl)-4-oxo-3,4-dihydropyrido[3,4-d]pyrimidin-2-yl)pyrrolidine-1-carboxylate (1.7 g, 3.51 mmol) in 1,4-dioxane (26 mL) under N₂. The mixture was stirred at 110° C. for 1 h. After cooling to rt, the mixture was diluted with water and extracted with EA (3×). The combined organic phases were washed with sat. aq. NaHCO₃ and brine and dried over Na₂SO₄. The solids were removed by filtration and the filtrate was evaporated to dryness. The crude mixture was purified by silica gel column chromatography (0 to 10% MeOH in DCM) to afford t-butyl (S)-2-(6-methyl-3-(4-(methylcarbamoyl)phenyl)-4-oxo-3,4-dihydropyrido[3,4-d]pyrimidin-2-yl)pyrrolidine-1-carboxylate (1.4 g, 86%) as a yellow solid. LC-MS: C₂₅H₂₉N₅O₄ [M+H]⁺: 464.

HCl 4N in dioxane (13 mL, 51.78 mmol) was added to a solution of t-butyl (S)-2-(6-methyl-3-(4-(methylcarbamoyl)phenyl)-4-oxo-3,4-dihydropyrido[3,4-d]pyrimidin-2-yl)pyrrolidine-1-carboxylate (1.2 g, 2.59 mmol) in anhydrous dioxane (15 mL) under N₂. The mixture was stirred at rt for 2 h, then diluted with sat. aq. NaHCO₃ and extracted with EA:isopropanol (85:15) (6×). The combined organic layers were washed with water and brine and dried over MgSO₄. The solids were removed by filtration and the filtrate was evaporated to dryness to afford (S)—N-methyl-4-(6-methyl-4-oxo-2-(pyrrolidin-2-yl)pyrido[3,4-d]pyrimidin-3(4H)-yl)benzamide (604 mg, 64%) as a brown oil, which was used as such in the next step. LC-MS: C₂₀H₂₁N₅O₂ [M+H]⁺: 364.

Acetone (0.86 mL, 11.63 mmol), AcOH (0.048 mL, 0.83 mmol) and NaCNBH₃ (209 mg, 3.32 mmol) were added to a solution of (S)—N-methyl-4-(6-methyl-4-oxo-2-(pyrrolidin-2-yl)pyrido[3,4-d]pyrimidin-3(4H)-yl)benzamide (604 mg, 1.66 mmol) in methanol (7 mL) under N₂. The mixture was stirred at rt for 2 h, then diluted with water and extracted with EA:isopropanol (85:15) (3×). The combined organic phases were washed with water and brine and dried over Na₂SO₄. The solids were removed by filtration and the filtrate was evaporated to dryness to afford (S)-4-(2-(1-isopropylpyrrolidin-2-yl)-6-methyl-4-oxopyrido[3,4-d]pyrimidin-3(4H)-yl)-N-methylbenzamide (626 mg, 93%) as a brown oil, which was used as such in the next step. LC-MS: C₂₃H₂₇N₅O₂ [M+H]⁺: 406.

Pd/C 10% (236 mg, 0.22 mmol) and AcOH (1.3 mL) were added to a solution of (S)-4-(2-(1-isopropylpyrrolidin-2-yl)-6-methyl-4-oxopyrido[3,4-d]pyrimidin-3(4H)-yl)-N-methylbenzamide (450 mg, 1.11 mmol) in THF (7 mL) and EtOH (7 mL) under N₂. The mixture was purged with H₂ and stirred under H₂ (1 atm) at rt for 3 days. The mixture was filtered over packed celite and the filtrate was evaporated to dryness to afford 4-(2-((S)-1-isopropylpyrrolidin-2-yl)-6-methyl-4-oxo-5,6,7,8-tetrahydropyrido[3,4-d]pyrimidin-3 (4H)-yl)-N-methylbenzamide (454 mg, 100%) as a brown oil, which used in the next step without further purification. LC-MS: C₂₃H₃₁N₅O₂ [M+H]⁺: 410.

A solution of 4-bromo-3-(trifluoromethyl)benzoyl chloride (105 mg, 0.37 mmol) in anhydrous DCM (1.2 mL) was added dropwise to a solution of 4-(2-((S)-1-isopropylpyrrolidin-2-yl)-6-methyl-4-oxo-5,6,7,8-tetrahydropyrido[3,4-d]pyrimidin-3(4H)-yl)-N-methylbenzamide (50 mg, 0.12 mmol) and DMAP (149 mg, 1.22 mmol) in anhydrous DCM (1.2 mL) at 0° C. under N₂. The mixture was stirred at rt for 10 min, then diluted with water and sat. aq. NaHCO₃ and extracted with DCM (2×). The combined organic layers were dried over Na₂SO₄. The solids were removed by filtration and the filtrate was evaporated to dryness. The crude product was purified by silica gel chromatography (0 to 10% MeOH in DCM), followed by prep-HPLC (15 to 100% MeCN in water [0.2% v/v NH₃]) and SFC purification (30:70 MeOH/CO₂ [0.2% v/v NH₃]) to afford two diastereomers of 4-(7-(4-bromo-3-(trifluoromethyl)benzoyl)-2-((S)-1-isopropylpyrrolidin-2-yl)-6-methyl-4-oxo-5,6,7,8-tetrahydropyrido[3,4-d]pyrimidin-3(4H)-yl)-N-methylbenzamide.

The first eluting (11a) (white solid, 3 mg, 4%) LC-MS: C₃₁H₃₃BrF₃N₅O₃ [M+H]⁺: 660/662, and second eluting (11b) (white solid, 17 mg, 21%). ¹H-NMR (DMSO-d₆, 400 MHz, 80° C.): 0.50 (d, J=6.4 Hz, 3H), 0.91 (d, J=6.3 Hz, 3H), 1.21 (d, J=7.1 Hz, 3H), 1.52-1.63 (m, 1H), 1.66-1.79 (m, 2H), 1.81-1.91 (m, 1H), 2.46-2.52 (m, 2H), 2.61-2.71

(m, 1H), 2.73-2.82 (m, 1H), 2.84 (d, J=4.4 Hz, 3H), 2.90-2.97 (m, 1H), 3.38-3.46 (m, 1H), 4.14-4.29 (m, 1H), 4.35-4.96 (m, 2H), 7.34-7.39 (m, 1H), 7.40-7.45 (m, 1H), 7.66-7.72 (m, 1H), 7.85-7.88 (m, 1H), 7.94-8.02 (m, 3H), 8.31-8.40 (m, 1H) ppm. LC-MS: $C_{31}H_{33}BrF_3N_5O_3$ [M+H]$^+$: 660/662.

Example 12

Compound 12

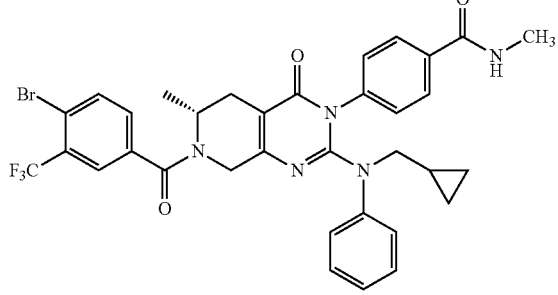

Aniline (0.48 g, 5.14 mmol) was added to a solution of (R)-4-(7-(4-bromo-3-(trifluoromethyl)benzoyl)-2-chloro-6-methyl-4-oxo-5,6,7,8-tetrahydropyrido[3,4-d]pyrimidin-3(4H)-yl)-N-methylbenzamide (1 g, 1.71 mmol) in anhydrous MeCN (10 mL) under N$_2$. The mixture was stirred at 130° C. for 4 h. After cooling to rt, the mixture was diluted with sat. aq. NaHCO$_3$ and extracted with EA (3×). The combined organic layers were washed with sat. aq. NaHCO$_3$ and brine and dried over Na$_2$SO$_4$. The solids were removed by filtration and the filtrate was evaporated to dryness to afford (R)-4-(7-(4-bromo-3-(trifluoromethyl)benzoyl)-6-methyl-4-oxo-2-(phenylamino)-5,6,7,8-tetrahydropyrido[3,4-d]pyrimidin-3(4H)-yl)-N-methylbenzamide (990 mg, 90%) as a light-brown solid, which was used as such in the next step. LC-MS: $C_{30}H_{25}BrF_3N_5O_3$ [M+H]$^+$: 640/642.

DIAD (331 mg, 1.64 mmol) was added to a solution of PPh$_3$ (430 mg, 1.64 mmol), cyclopropylmethanol (307 mg, 3.28 mmol) and (R)-4-(7-(4-bromo-3-(trifluoromethyl)benzoyl)-6-methyl-4-oxo-2-(phenylamino)-5,6,7,8-tetrahydropyrido[3,4-d]pyrimidin-3(4H)-yl)-N-methylbenzamide (700 mg, 1.093 mmol) in anhydrous toluene (7 mL) at 0° C. under N$_2$. The mixture was stirred at rt for 2 days, and then DIAD (331 mg, 0.33 mL, 1.64 mmol), PPh$_3$ (430 mg, 1.64 mmol) and cyclopropylmethanol (307 mg, 3.28 mmol) were added. The mixture was stirred at rt for 3 days. The mixture was diluted with water and extracted with EA (3×). The combined organic layers were washed with brine and dried over Na$_2$SO$_4$. The solids were removed by filtration and the filtrate was evaporated to dryness. The crude product was purified by chromatography on silica gel (0 to 10% MeOH in DCM, and prep-HPLC (10 to 100% MeCN in water [0.2% v/v NH$_3$]) to afford (R)-4-(7-(4-bromo-3-(trifluoromethyl)benzoyl)-2-((cyclopropylmethyl)(phenyl)amino)-6-methyl-4-oxo-5,6,7,8-tetrahydropyrido[3,4-d]pyrimidin-3(4H)-yl)-N-methylbenzamide (12) (34 mg, 4%) as a white solid. $^1$H-NMR (DMSO-d$_6$, 400 MHz, 80° C.): 0.10-0.23 (m, 2H), 0.35-0.52 (m, 2H), 1.11-1.22 (m, 2H), 1.26 (d, J=6.8 Hz, 3H), 2.56-2.66 (m, 1H), 2.78 (d, J=4.8 Hz, 3H), 3.34-3.45 (m, 2H), 4.11-4.30 (m, 1H), 4.36-4.99 (m, 2H), 6.59-6.64 (m, 2H), 6.85 (d, J=7.6 Hz, 2H), 6.94-7.07 (m, 3H), 7.51-7.59 (m, 2H), 7.71 (dd, J=8.0 Hz, 1.3 Hz, 1H), 7.89 (d, J=1.3 Hz, 1H), 8.00 (d, J=8.1 Hz, 1H), 8.07-8.13 (m, 1H) ppm. LC-MS: $C_{34}H_{31}BrF_3N_5O_3$ [M+H]$^+$: 694/696.

Example 13

Compound 13

1-methylazetidin-3-amine (801 mg, 9.3 mmol) was added to a solution of (R)-4-(7-(4-bromo-3-(trifluoromethyl)benzoyl)-2-chloro-6-methyl-4-oxo-5,6,7,8-tetrahydropyrido[3,4-d]pyrimidin-3(4H)-yl)-N-methylbenzamide (1.08 g, 1.86 mmol) and DIPEA (3 mL, 18.6 mmol) in anhydrous MeCN (19 mL) under N$_2$. The mixture was stirred at 110° C. for 3 h, cooled to rt, and then diluted with water and extracted with EA (3×). The combined organic layers were washed with brine (2×) and dried over Na$_2$SO$_4$. The solids were removed by filtration and the filtrate was evaporated to dryness. The crude product was purified by silica gel chromatography (2 to 8% [MeOH:NH$_4$OH (9:1)] in DCM) to afford (R)-4-(7-(4-bromo-3-(trifluoromethyl)benzoyl)-6-methyl-2-((1-methylazetidin-3-yl)amino)-4-oxo-5,6,7,8-tetrahydropyrido[3,4-d]pyrimidin-3(4H)-yl)-N-methylbenzamide (809 mg, 69%) as a yellow solid. LC-MS: $C_{28}H_{28}BrF_3N_6O_3$ [M+H]$^+$: 633/635.

DIPEA (0.25 mL, 1.52 mmol) was added to a mixture of (R)-4-(7-(4-bromo-3-(trifluoromethyl)benzoyl)-6-methyl-2-((1-methylazetidin-3-yl)amino)-4-oxo-5,6,7,8-tetrahydropyrido[3,4-d]pyrimidin-3(4H)-yl)-N-methylbenzamide (480 mg, 0.76 mmol) and BnBr (130 mg, 0.76 mmol) in anhydrous DMF (8 mL) under N$_2$. The mixture was stirred at rt for 18 h, and then diluted with water and extracted EA (3×). The combined organic layers were washed with water (2×), brine (2×) and dried over Na$_2$SO$_4$. The solids were removed by filtration and the filtrate was evaporated to dryness. The crude product was purified by chromatography on silica gel (0 to 10% MeOH in DCM) to afford (R)-4-(2-(benzyl(1-methylazetidin-3-yl)amino)-7-(4-bromo-3-(trifluoromethyl)benzoyl)-6-methyl-4-oxo-5,6,7,8-tetrahydropyrido[3,4-d]pyrimidin-3(4H)-yl)-N-methylbenzamide (13) (36 mg, 7%) as a beige solid. LC-MS: $C_{35}H_{34}BrF_3N_6O_3$ [M+H]$^+$: 723/725.

The following compounds in Table 1 were made using procedures analogous to those described for the synthesis of Compounds 2, 6, 9 and 10.

TABLE 1

| Compound | Structure | LC-MS [M + H]⁺ | NMR |
|---|---|---|---|
| 14 | 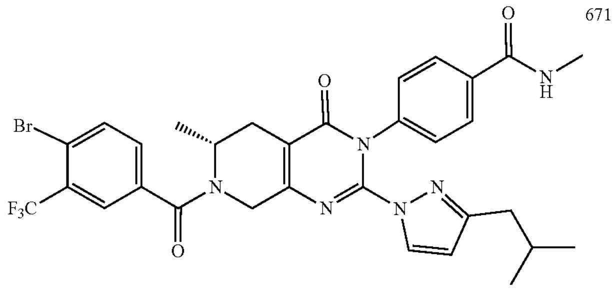 | 671 | |
| 15 | 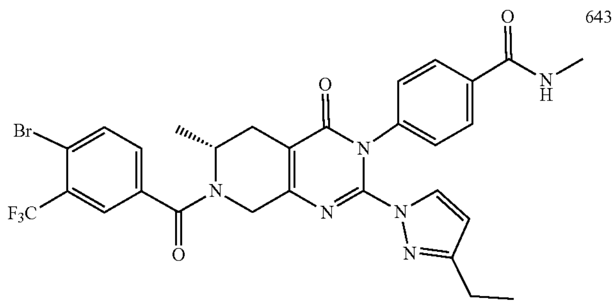 | 643 | ¹H-NMR (DMSO-d₆, 400 MHz, 80° C.): 0.79-0.90 (m, 3H), 1.26 (d, J = 6.9 Hz, 3H), 2.28 (q, J = 7.6 Hz, 2H), 2.50-2.54 (m, 1H), 2.64-2.78 (m, 1H), 2.80 (d, J = 4.4 Hz, 3H), 4.08-4.40 (m, 1H), 4.40-4.96 (m, 2H), 6.14 (d, J = 2.0 Hz, 1H), 7.28 (d, J = 8.0 Hz, 2H), 7.70 (d, J = 7.9 Hz, 1H), 7.79 (d, J = 8.0 Hz, 2H), 7.89 (s, 1H), 7.95-8.04 (m, 2H), 8.18-8.27 (m, 1H) ppm. |
| 16 | 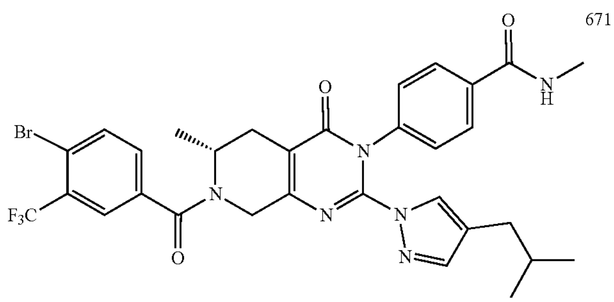 | 671 | ¹H-NMR (DMSO-d₆, 400 MHz, 80° C.): 0.78 (d, J = 6.6 Hz, 6H), 1.26 (d, J = 6.9 Hz, 3H), 1.62-1.66 (m, 1H), 2.22 (d, J = 6.8 Hz, 2H), 2.50-2.54 (m, 1H), 2.64-2.78 (m, 1H), 2.80 (d, J = 4.5 Hz, 3H), 4.11-4.39 (m, 1H), 4.38-5.00 (m, 2H), 7.25 (s, 1H), 7.28 (d, J = 8.0 Hz, 2H), 7.70 (dd, J = 8.3 Hz, 1.4 Hz, 1H), 7.78 (d, J = 8.6 Hz, 2H), 7.85-7.91 (m, 2H), 8.00 (d, J = 8.3 Hz, 1H), 8.20-8.27 (m, 1H) ppm |
| 19 | 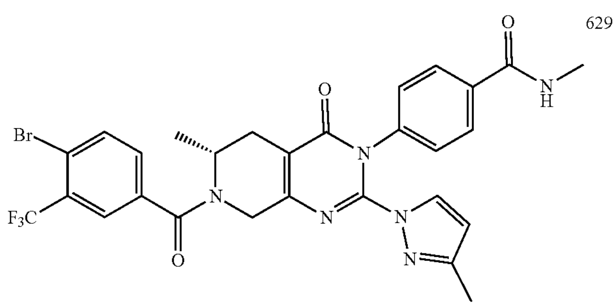 | 629 | ¹H-NMR (DMSO-d₆, 400 MHz, 80° C.): 1.26 (d, J = 6.9 Hz, 3H), 1.92 (s, 3H), 2.48-2.56 (m, 1H), 2.69-2.78 (m, 1H), 2.80 (d, J = 4.6 Hz, 3H), 4.20-4.33 (m, 1H), 4.45-4.99 (m, 2H), 6.11 (d, J = 2.7 Hz, 1H), 7.30 (d, J = 8.5 Hz, 2H), 7.67-7.72 (m, 1H), 7.79 (d, J = 8.6 Hz, 2H), 7.87-7.90 (m, 1H), 7.93-7.97 (m, 1H), 8.00 (d, J = 8.5 Hz, 1H), 8.21-8.29 (m, 1H) ppm |
| 20 | 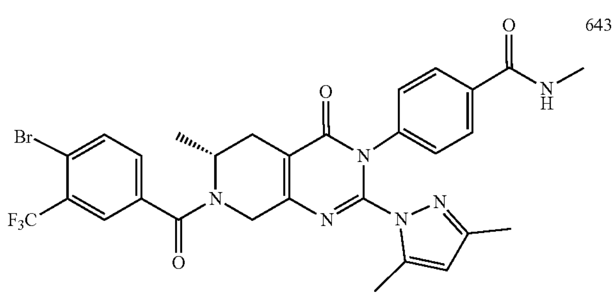 | 643 | |

TABLE 1-continued

| Compound | Structure | LC-MS [M + H]+ | NMR |
|---|---|---|---|
| 21 | (structure shown) | 657 | |

Example 14

Compound 17

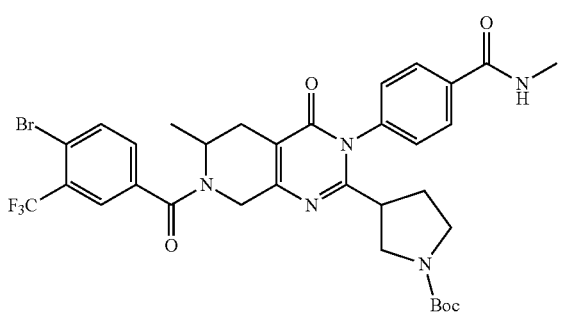 [SMILES: CNC(=O)c1ccc(-n2c(C3CCN(C(=O)OC(C)(C)C)C3)nc3c(c2=O)CC(C)N(C(=O)c2ccc(Br)c(C(F)(F)F)c2)C3)cc1]

Triphenyl phosphite (22.48 g, 72.43 mmol) was added to a solution of 5-amino-2-chloropyridine-4-carboxylic acid (5 g, 28.97 mmol) and 1-[(t-butoxy)carbonyl]pyrrolidine-3-carboxylic acid (6.24 g, 28.97 mmol) in pyridine (100 mL) under $N_2$. The mixture was stirred at 70° C. for 4 h, at which point 4-amino-N-methylbenzamide (5.22 g, 34.77 mmol) was added. The mixture was stirred at 70° C. for 16 h. After cooling to rt, the mixture was diluted with water and extracted with EA (3×). The combined organic phases were washed with water, sat. aq. $NaHCO_3$ and brine and dried over $MgSO_4$. The solids were removed by filtration and the filtrate was evaporated to dryness. The crude mixture was purified by flash chromatography on silica gel (0% to 4% MeOH in DCM) to give tert-butyl 3-(6-chloro-3-(4-(methylcarbamoyl)phenyl)-4-oxo-3,4-dihydropyrido[3,4-d]pyrimidin-2-yl)pyrrolidine-1-carboxylate (4.7 g) as a yellow solid. $^1$H-NMR (DMSO-$d_6$, 400 MHz): 1.37 (s, 9H), 1.84-1.96 (m, 1H), 2.11-2.34 (m, 1H), 2.83 (d, J=4.4 Hz, 3H), 2.99-3.15 (m, 2H), 3.24-3.33 (m, 1H), 3.39-3.49 (m, 1H), 3.50-3.63 (m, 1H), 7.58-7.63 (m, 2H), 8.00 (s, 1H), 8.00-8.04 (m, 2H), 8.57-8.63 (m, 1H), 8.93 (s, 1H) ppm. LC-MS: $C_{24}H_{26}ClN_5O_4$ [M+H]+: 484.

Pd(dppf)$Cl_2$·DCM (0.506 g, 0.62 mmol), $K_2CO_3$ (2.57 g, 18.6 mmol) and trimethylboroxine 50% (8.65 mL, 30.99 mmol) were added to a solution of t-butyl 3-(6-chloro-3-(4-(methylcarbamoyl)phenyl)-4-oxo-3,4-dihydropyrido[3,4-d]pyrimidin-2-yl)pyrrolidine-1-carboxylate (3 g, 6.2 mmol) in 1,4-dioxane (47 mL) under $N_2$. The mixture was stirred at 110° C. for 1 h. After cooling to rt, the mixture was diluted with water and extracted with EA (3×). The combined organic phases were washed with sat. aq. $NaHCO_3$ and brine and dried over $Na_2SO_4$. The solids were removed by filtration and the filtrate was evaporated to dryness. The crude mixture was purified by flash chromatography on silica gel (0 to 10% MeOH in DCM) to give 3-(6-methyl-3-(4-(methylcarbamoyl)phenyl)-4-oxo-3,4-dihydropyrido[3,4-d]pyrimidin-2-yl)pyrrolidine-1-carboxylate (2.76 g, 96%) as a yellow solid. $^1$H-NMR (DMSO-$d_6$, 400 MHz): 1.37 (s, 9H), 1.84-1.96 (m, 1H), 2.11-2.34 (m, 1H), 2.63 (s, 3H), 2.83 (d, J=4.4 Hz, 3H), 2.99-3.15 (m, 2H), 3.24-3.33 (m, 1H), 3.39-3.49 (m, 1H), 3.50-3.63 (m, 1H), 7.58-7.63 (m, 2H), 7.81 (s, 1H), 7.98-8.04 (m, 2H), 8.57-8.63 (m, 1H), 8.95 (s, 1H) ppm. LC-MS: $C_{25}H_{29}N_5O_4$ [M+H]+: 464.

Pd/C 10% (3.5 g) was added to a solution of tert-butyl 3-(6-methyl-3-(4-(methylcarbamoyl)phenyl)-4-oxo-3,4-dihydropyrido[3,4-d]pyrimidin-2-yl)pyrrolidine-1-carboxylate (4 g, 8.63 mmol) in THF (80 mL), EtOH (80 mL) and AcOH (10 mL). The mixture was stirred at 40° C. under $H_2$ atmosphere (balloon) for 8 d. The mixture was filtered over a pad of celite and the filtrate was evaporated to dryness. The residue was dissolved in EA/iPrOH (85:15), washed with water (2×) and brine (2×) and dried over $Na_2SO_4$. The solids were removed by filtration and the filtrate was evaporated to dryness to give tert-butyl 3-(6-methyl-3-(4-(methylcarbamoyl)phenyl)-4-oxo-3,4,5,6,7,8-hexahydropyrido[3,4-d]pyrimidin-2-yl)pyrrolidine-1-carboxylate (3.23 g, 80%) as a yellow oil, which was used as such in the next step. LC-MS: $C_{25}H_{33}N_5O_4$ [M+H]+: 468.

DIPEA (3.43 mL, 20.72 mmol) and HATU (3.94 g, 10.36 mmol) were added to a solution of t-butyl 3-(6-methyl-3-(4-(methylcarbamoyl)phenyl)-4-oxo-3,4,5,6,7,8-hexahydropyrido[3,4-d]pyrimidin-2-yl)pyrrolidine-1-carboxylate (3.23 g, 6.91 mmol) and 4-bromo-3-(trifluoromethyl)benzoic acid (1.86 g, 6.91 mmol) in anhydrous DMF (150 mL) under $N_2$. The mixture was stirred at rt for 16 h. The mixture was diluted with water and extracted with EA (3×). The combined organic phases were washed with water and brine and dried over $Na_2SO_4$. The solids were removed by filtration and the filtrate was evaporated to dryness. The crude product was purified by chromatography on silica gel (0 to 5% MeOH in DCM) to give t-butyl 3-(7-(4-bromo-3-(trifluoromethyl)benzoyl)-6-methyl-3-(4-(methylcarbamoyl)phenyl)-4-oxo-3,4,5,6,7,8-hexahydropyrido[3,4-d]pyrimidin-2-yl)pyrrolidine-1-carboxylate (17) (0.65 g, 13%) as a white solid. $^1$H-NMR (DMSO-$d_6$, 400 MHz, 80° C.): 1.20 (d, J=7.1 Hz, 3H), 1.37 (d, J=6.5 Hz, 9H), 1.82-1.93 (m, 1H), 2.02-2.16 (m, 1H), 2.63-2.70 (m, 1H), 2.84 (d, J=4.5 Hz, 3H), 2.95-3.03 (m, 1H), 3.22-3.32 (m, 1H), 3.34-3.45 (m, 1H), 3.47-3.55 (m, 1H), 4.16-4.21 (m, 1H), 4.58-4.65 (m, 2H), 7.43-7.51 (m, 2H), 7.66-7.69 (m, 1H), 7.86-7.87 (m, 1H), 7.97-8.00 (m, 3H), 8.34-8.35 (m, 1H) ppm. LC-MS: $C_{33}H_{35}BrF_3N_5O_5[M+H]^+$: 718/720.

Example 15

Compound 18

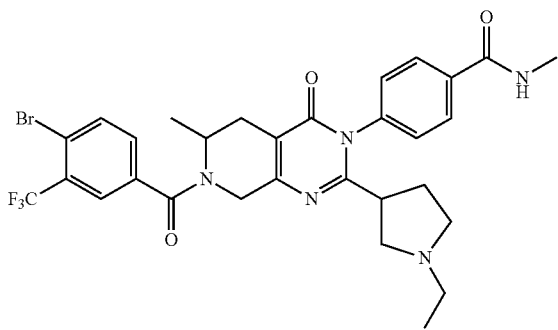 [SMILES: CCN1CCC(c2nc3c(c(=O)n2-c2ccc(C(=O)NC)cc2)CC(C)N(C(=O)c2ccc(Br)c(C(F)(F)F)c2)C3)C1]

TFA (1 mL) was added to a solution of tert-butyl 3-(7-(4-bromo-3-(trifluoromethyl)benzoyl)-6-methyl-3-(4-(methylcarbamoyl)phenyl)-4-oxo-3,4,5,6,7,8-hexahydropyrido[3,4-d]pyrimidin-2-yl)pyrrolidine-1-carboxylate (17) (493 mg, 0.69 mmol) in DCM (6 mL) under $N_2$. The mixture was stirred at rt for 1 h. The mixture was diluted with sat. aq. $Na_2CO_3$ and extracted with DCM (3×). The combined organic layers were washed with sat. aq. $Na_2CO_3$ (2×) and dried over $Na_2SO_4$. The solids were removed by filtration and the filtrate was evaporated to dryness to afford 4-(7-(4-bromo-3-(trifluoromethyl)benzoyl)-6-methyl-4-oxo-2-(pyrrolidin-3-yl)-5,6,7,8-tetrahydropyrido[3,4-d]pyrimidin-3 (4H)-yl)-N-methylbenzamide (370 mg, 87%) as a red solid, which was used as such in the next step. LC-MS: $C_{28}H_{27}BrF_3N_5O_3$ $[M+H]^+$: 618/620.

Acetaldehyde (155 mg, 0.2 mL, 3.51 mmol), AcOH (0.014 mL, 0.25 mmol) and $NaCNBH_3$ (63 mg, 1.00 mmol) were added to a solution of 4-(7-(4-bromo-3-(trifluoromethyl)benzoyl)-6-methyl-4-oxo-2-(pyrrolidin-3-yl)-5,6,7,8-tetrahydropyrido[3,4-d]pyrimidin-3(4H)-yl)-N-methylbenzamide (310 mg, 0.50 mmol) in MeOH (4 mL) under $N_2$. The mixture was stirred at rt for 1 h. The mixture was diluted with water and sat. aq. $Na_2CO_3$ and extracted with EA (3×). The combined organic phases were washed with sat aq. $Na_2CO_3$ and brine and dried over $Na_2SO_4$. The solids were removed by filtration and the filtrate was evaporated to dryness. The crude mixture was purified by chromatography on silica gel (0 to 10% [MeOH/$NH_4OH$ (9:1)] in DCM) and prep-HPLC (20% to 100% MeCN in water [0.2% v/v $NH_3$]) to give 4-(7-(4-bromo-3-(trifluoromethyl)benzoyl)-2-(1-ethylpyrrolidin-3-yl)-6-methyl-4-oxo-5,6,7,8-tetrahydropyrido[3,4-d]pyrimidin-3(4H)-yl)-N-methylbenzamide (18) (10 mg, 3%) as a white solid. $^1$H-NMR (DMSO-$d_6$, 400 MHz, 80° C.): 0.91-1.00 (m, 3H), 1.16-1.25 (m, 3H), 1.59-1.70 (m, 1H), 1.99-2.11 (m, 1H), 2.26-2.44 (m, 5H), 2.60-2.71 (m, 3H), 2.80-2.87 (m, 3H), 2.88-2.96 (m, 1H), 4.11-4.29 (m, 1H), 4.32-4.90 (m, 2H), 7.36-7.43 (m, 1H), 7.43-7.50 (m, 1H), 7.64-7.72 (m, 1H), 7.82-7.91 (m, 1H), 7.93-8.05 (m, 3H), 8.32-8.39 (m, 1H) ppm. LC-MS: $C_{30}H_{31}BrF_3N_5O_3$ $[M+H]^+$: 646/648.

Example A

HBV-DNA Antiviral Assay Using HepG2.117 Cells

The following assay procedure describes the HBV antiviral assay, using HepG2.117 cells, which carry a stably integrated genotype D HBV genome under the control of a Tet-off promoter, and intracellular HBV DNA quantification as endpoint. Cell viability is assessed in parallel by measuring the intracellular ATP content using CellTiter-Glo 2.0 (Promega).

On day 0, HepG2.117 cells (which are maintained in routine cell culture with doxycycline present in the medium at a final concentration of 1 μg/mL) are seeded in 96-well plates (white with clear bottom) at a density of $2.0 \times 10^4$ cells/well (0.1 mL/well) in medium without doxycycline to induce pgRNA transcription and subsequent formation of HBV particles. The cells are incubated at 37° C. and 5% $CO_2$.

On day 1, medium is removed from each well, the test articles are diluted in culture medium without doxycycline and 100 μL was added to cell culture wells (9 concentrations, 4-fold dilution). For each plate, 6 untreated (merely DMSO) wells are included. The final concentration of DMSO in the culture medium is 2%. Each plate is prepared in duplicate (one for HBV DNA extraction, one for CellTiter-Glo 2.0 measurement). The cells are incubated at 37° C. and 5% $CO_2$ for 3 days.

On day 4, cell viability is assessed using CellTiter-Glo 2.0 and cell lysates are prepared for HBV DNA extraction and subsequent quantification by qPCR.

HBV DNA Quantification by qPCR

Medium is removed from each well and 100 μL of 0.33% NP-40 in $H_2O$ was added to each well. Plates are sealed, incubated at 4° C. for 5 mins, vortexed extensively and centrifuged briefly. Next, 35 μL of lysate is added to 65 μL QuickExtract DNA Extraction Solution (Epicentre) in a PCR plate for each well. PCR plate is incubated at 65° C. for 6 mins, 98° C. for 2 mins and finally cooled to 4° C. HBV DNA is then quantified by qPCR with HBV-specific primers and probes as specified in Table 2 using the Bio-Rad SSOAdvanced Universal Probes Supermix on a CFX96 machine (Bio-Rad). The PCR cycle program consisted of 95° C. for 3 mins, followed by 40 cycles at 95° C. for 10 sec and 60° C. for 30 sec.

TABLE 2

| HBV DNA Primers and Probe for HepG2.117 assay | | |
|---|---|---|
| Items | Name | Sequence (5'→3') |
| HBV Primer | HBV-forward | GTGTCTGCGGCGTTTTATCA (SEQ ID NO: 1) |
|  | HBV-reverse | GACAAACGGGCAACATACCTT (SEQ ID NO: 2) |
| HBV Probe | HBV probe | FAM/CCTCTKCAT/ZEN/CCTGC TGCTATGCCTCATC/3IABkFQ/ (SEQ ID NO: 3) |

A DNA standard is prepared by dilution of an IDT gBlock corresponding to the amplicon with concentrations ranging from $10^{42}$ to $10^{48}$ copies/input (i.e. per 4 μL) and used to generate a standard curve by plotting Cq values vs. HBV DNA standard concentration. The quantity of HBV DNA in each sample is determined by interpolating from the standard curve.

Cell Viability

Using the other plates, the cell viability is quantified by CellTiter-Glo 2.0 according to the manufacturer's manual. In brief, 100 μL of reagent solution is added to the culture plates and shaken for 2'. The plates are incubated at room temperature for 10 min and luminescence signal is subsequently measured on a VarioSkan Lux (ThermoFisher) plate reader.

Data Analysis

Cell viability is calculated as follows: % Cell viability= (luminescence value of test sample)/(average luminescence value of 2% DMSO control)×100%. HBV DNA inhibition was calculated as follows: 100−(HBV DNA copy number of test sample)/(average HBV DNA copy number of 2% DMSO control)×100%. No normalization to entecavir is required due to the excellent dynamic window of this assay. The $CC_{50}$, $EC_{50}$ and $EC_{90}$ values were determined by dose-response curves fitted using non-linear regression.

As shown in Table 3, compounds of Formula (I) are active against HBV, where 'A' indicates an $EC_{50} \leq 50$ nM, 'B' indicates an $EC_{50} > 50$ nM and $\leq 500$ nM, 'C' indicates an $EC_{50} > 500$ nM and $\leq 5000$ nM, and 'D' indicates an $EC_{50} > 5000$ nM. Cell viability assessments indicated a large window between effective antiviral concentrations and cytotoxic compound concentrations.

TABLE 3

| Compound | $EC_{50}$ (nM) | CC50 (nM) |
|---|---|---|
| 1a | A | >50000 |
| 1b | A | >50000 |
| 2 | A | >50000 |
| 3 | A | >50000 |
| 4 | A | >50000 |
| 5 | A | >500 |
| 6 | A | >50000 |
| 7 | C | >500 |
| 8 | A | 30046 |
| 9 | B | 27758 |
| 10 | A | >50000 |
| 11a | C | >50000 |
| 11b | C | >50000 |
| 12 | A | 10849 |
| 13 | C | 26977 |
| 14 | A | >50000 |
| 15 | A | >50000 |
| 16 | B | >50000 |
| 17 | B | 24213 |
| 18 | D | >50000 |
| 19 | A | >50000 |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof, having the structure:

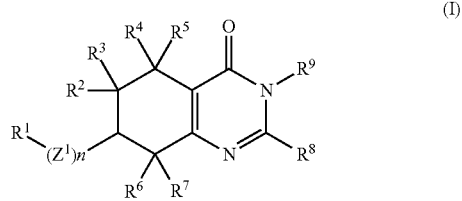

wherein:
n is 1;
$Z^1$ is —C(=O)—;
$R^1$ is selected from the group consisting of

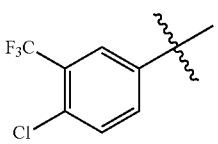 and 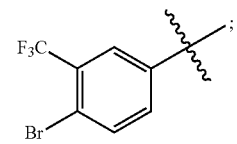

$R^2$ and $R^3$ are independently selected from the group consisting of hydrogen and an unsubstituted $C_{1-4}$ alkyl;
$R^4$, $R^5$, $R^6$ and $R^7$ are each hydrogen;
$R^8$ is selected from the group consisting of an optionally substituted monocyclic heteroaryl and —NR$^{14A}$R$^{14B}$;
$R^9$ is a substituted phenyl, a substituted monocyclic heteroaryl or a substituted fused-bicyclic heteroaryl, wherein the substituted phenyl, the substituted monocyclic heteroaryl or the substituted fused-bicyclic heteroaryl is substituted with one or more substituents selected from the group consisting of halogen, an unsubstituted $C_{1-4}$ alkyl, an unsubstituted $C_{1-4}$ haloalkyl, an unsubstituted $C_{1-4}$ alkoxy, an optionally substituted monocyclic heteroaryl, an optionally substituted monocyclic heterocyclyl, amino, a mono-substituted amine, a di-substituted amine and —C(=O)NHR$^{15}$;
$R^{14A}$ is a monocyclic $C_{3-6}$ cycloalkyl optionally substituted with one or two halogens, a monocyclic $C_{3-6}$ cycloalkyl($C_{1-4}$ alkyl) optionally substituted with one or two halogens, an optionally substituted 4-6 member monocyclic heterocyclyl or an optionally substituted monocyclic 4- to 6-membered heterocyclyl($C_{1-4}$ alkyl);
$R^{14B}$ is selected from the group consisting of an optionally substituted aryl and an optionally substituted aryl($C_{1-4}$ alkyl); and
$R^{15}$ is hydrogen, an unsubstituted $C_{1-6}$ alkyl, an optionally substituted $C_{2-6}$ alkenyl, an optionally substituted $C_{1-6}$ alkynyl or an optionally substituted $C_{3-6}$ monocyclic cycloalkyl.

2. The compound of claim 1, wherein $R^1$ is

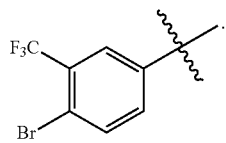

3. The compound of claim 1, wherein $R^1$ is

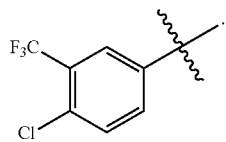 [SMILES: *c1ccc(Cl)c(C(F)(F)F)c1]

4. The compound of claim 1, wherein $R^2$ is an unsubstituted $C_{1-4}$ alkyl; and $R^3$ is hydrogen.

5. The compound of claim 1, wherein $R^8$ is an optionally substituted monocyclic heteroaryl.

6. The compound of claim 1, wherein $R^8$ is —$NR^{14A}R^{14B}$.

7. The compound of claim 6, wherein $R^{14A}$ is a monocyclic $C_{3-6}$ cycloalkyl($C_{1-4}$ alkyl) optionally substituted with one or two halogens or an optionally substituted 4-6 member monocyclic heterocyclyl.

8. The compound of claim 6, wherein $R^{14A}$ is a monocyclic $C_{3-6}$ cycloalkyl optionally substituted with one or two halogens.

9. The compound of claim 6, wherein $R^{14B}$ is an optionally substituted aryl.

10. The compound of claim 6, wherein $R^{14B}$ is an optionally substituted aryl($C_{1-4}$ alkyl), and wherein the aryl of the aryl($C_{1-4}$ alkyl) is optionally substituted with a substituents selected from the group consisting of halogen, an unsubstituted $C_{1-6}$ alkyl, an optionally substituted a $C_{2-5}$ alkenyl, an optionally substituted a $C_{2-5}$ alkynyl and an optionally substituted monocyclic heteroaryl.

11. The compound of claim 10, wherein the optionally substituted aryl($C_{1-4}$ alkyl) is an optionally substituted benzyl.

12. The compound of claim 1, wherein $R^9$ is a substituted phenyl.

13. The compound of claim 12, wherein $R^9$ is substituted with —C(=O)NHR$^{15}$.

14. The compound of claim 13, wherein $R^{15}$ is an unsubstituted $C_{1-6}$ alkyl.

15. The compound of claim 1 selected from the group consisting of:

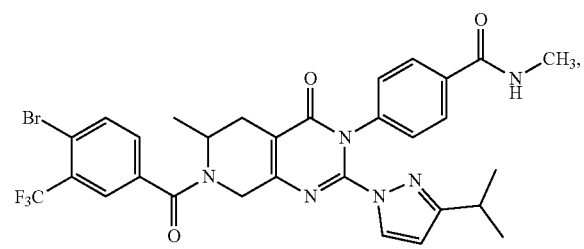

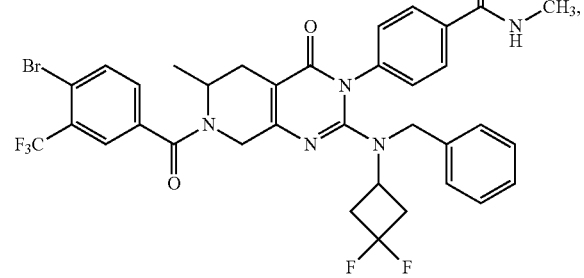

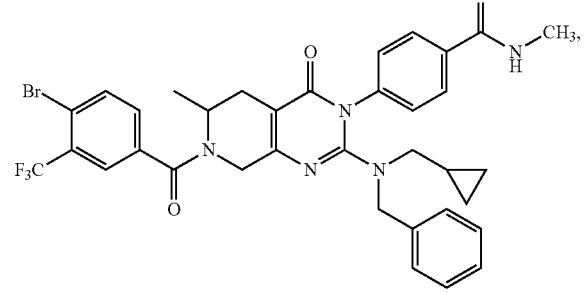

-continued

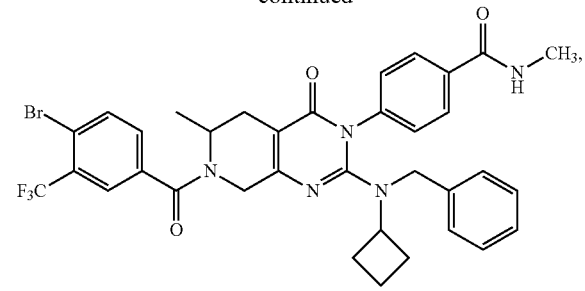

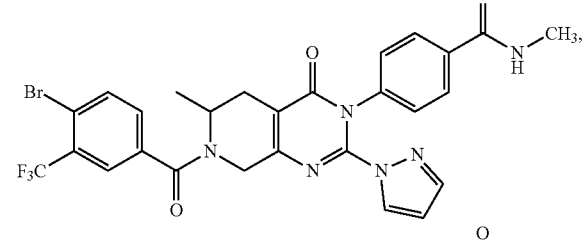

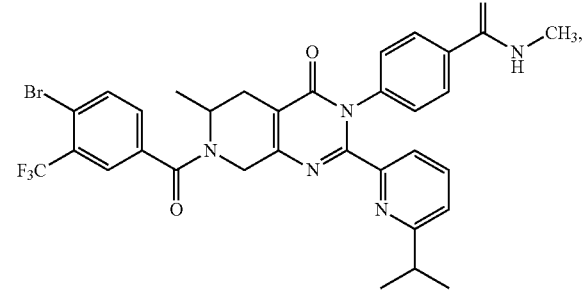

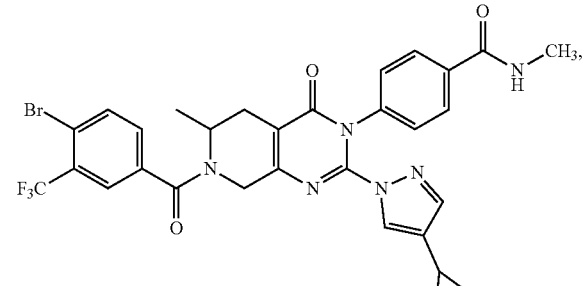

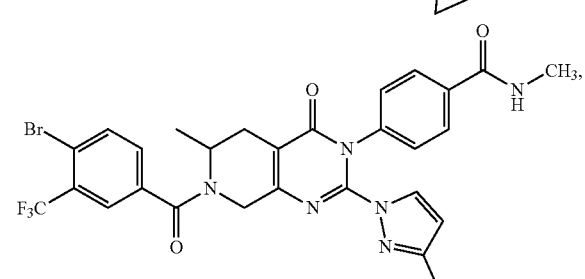

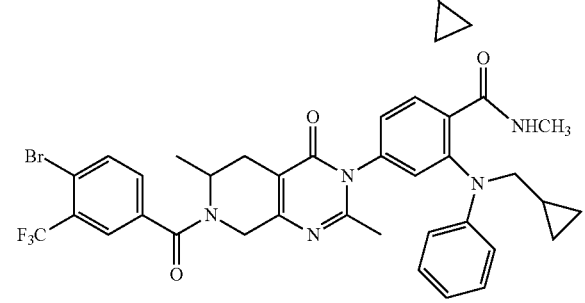

115
-continued
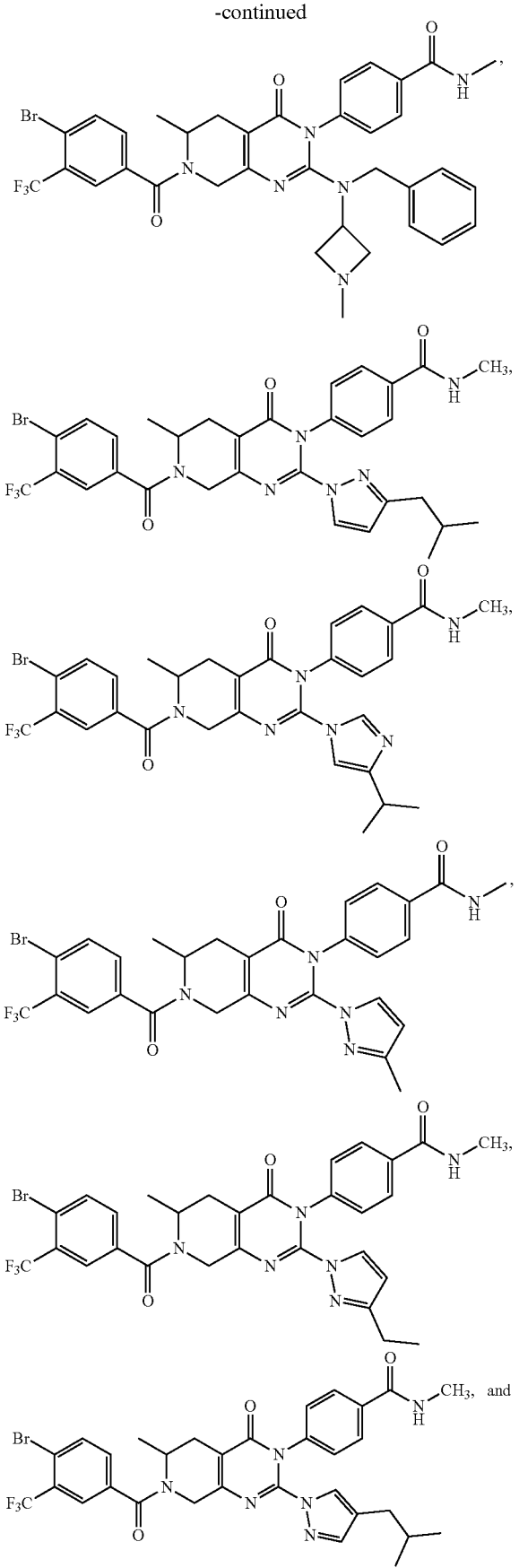
116
-continued
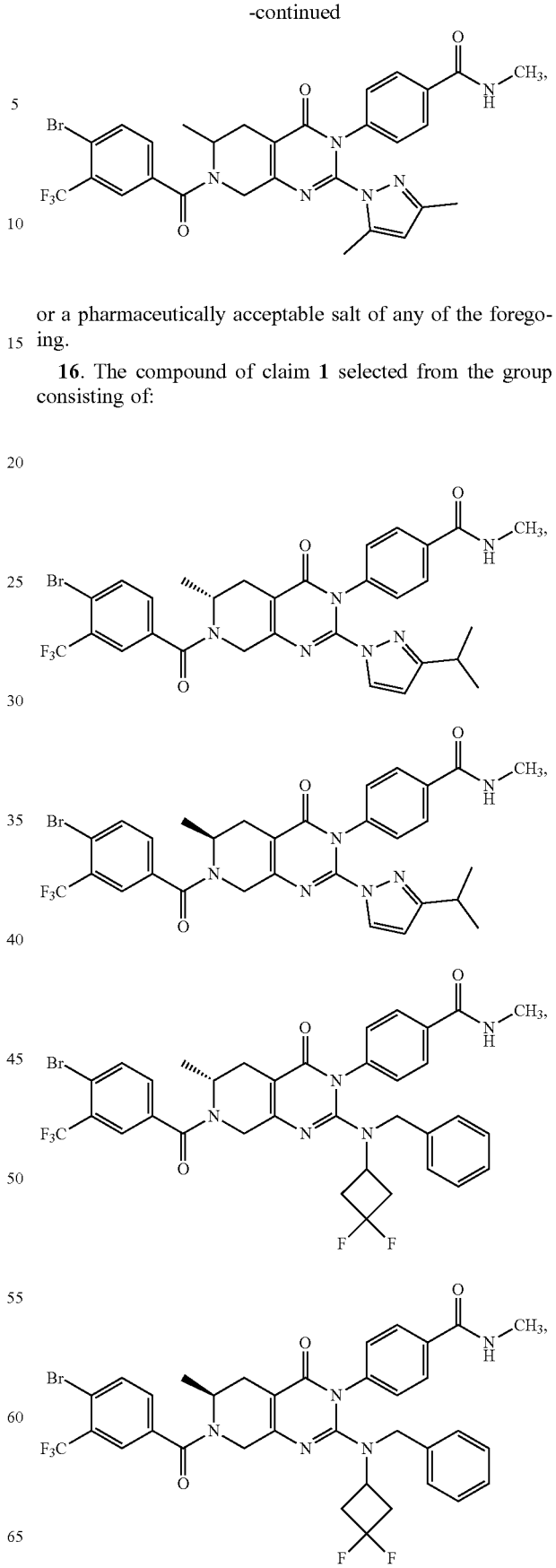
or a pharmaceutically acceptable salt of any of the foregoing.
16. The compound of claim 1 selected from the group consisting of:

-continued
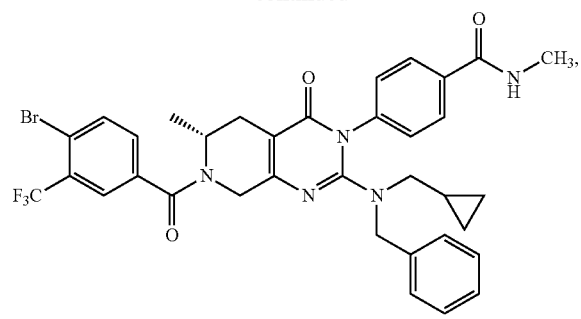
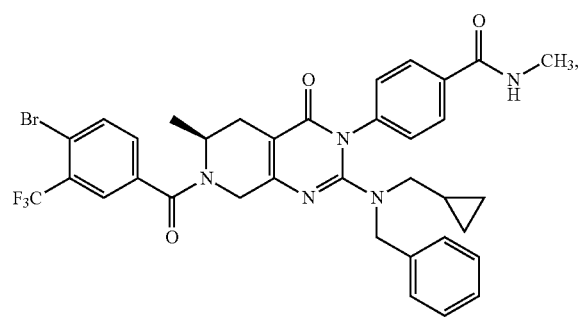
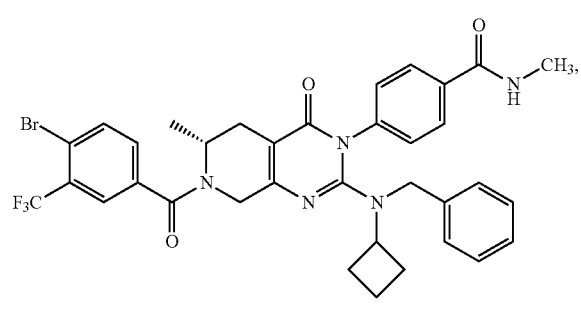
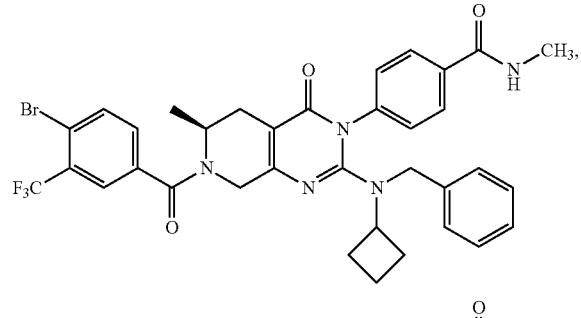
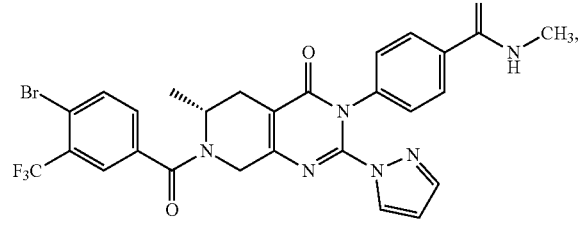
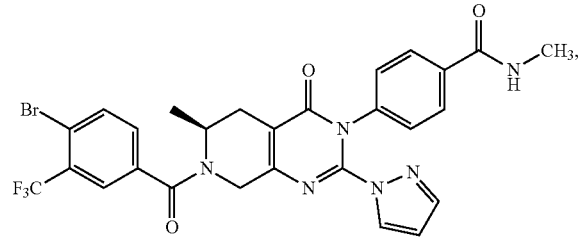
-continued
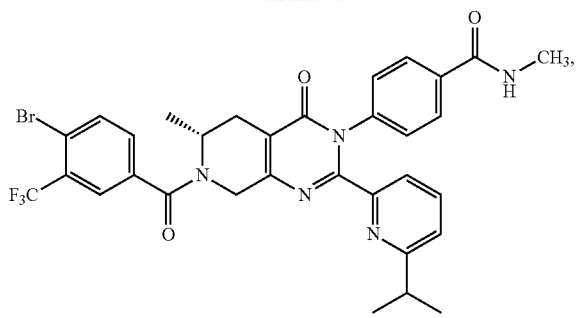
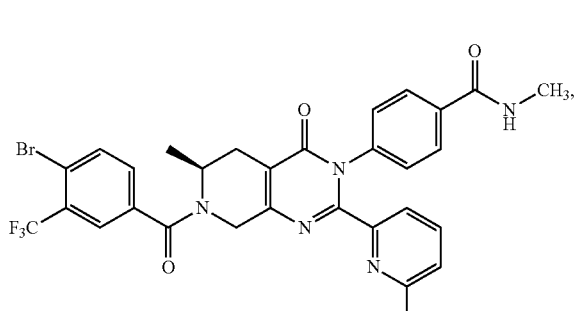
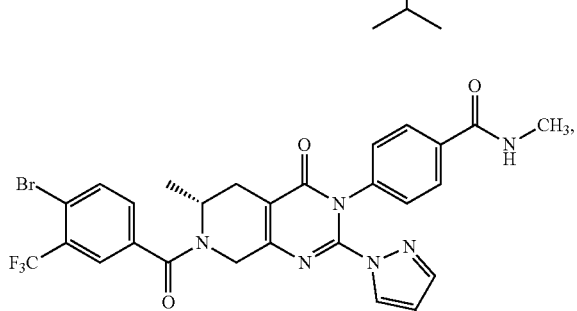
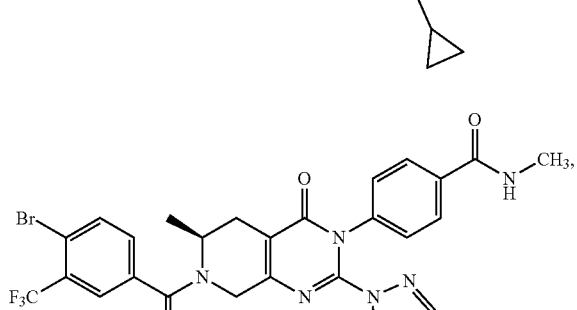
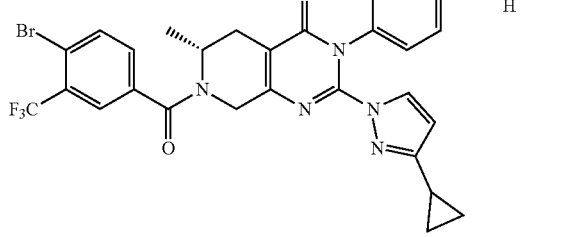

119
-continued
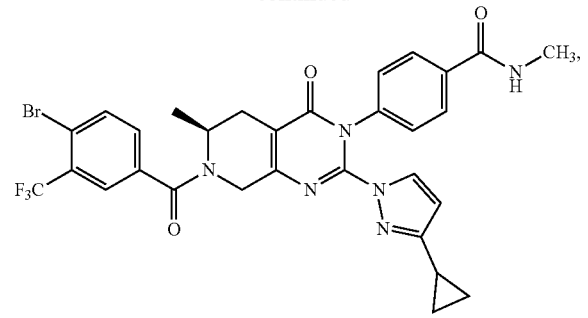
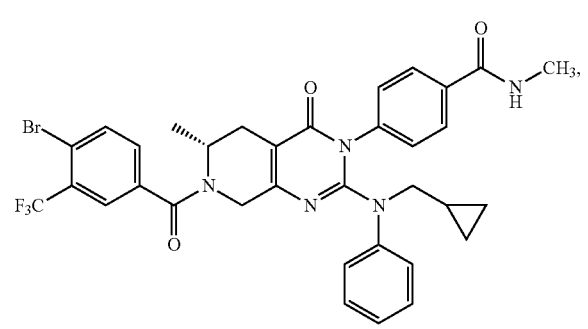
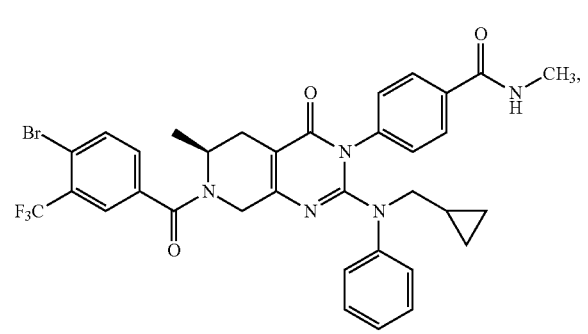
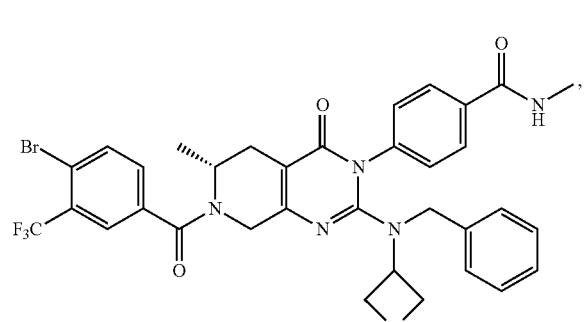
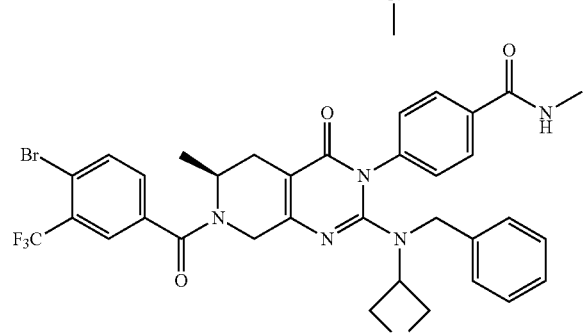
120
-continued
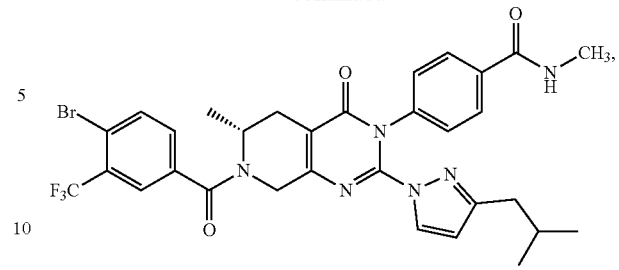
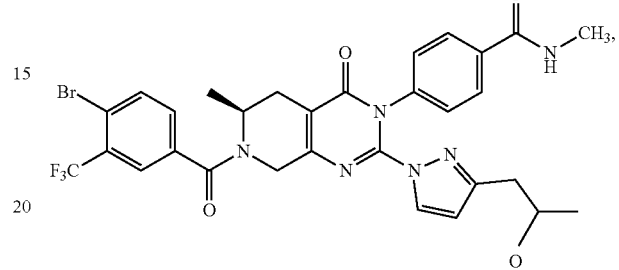
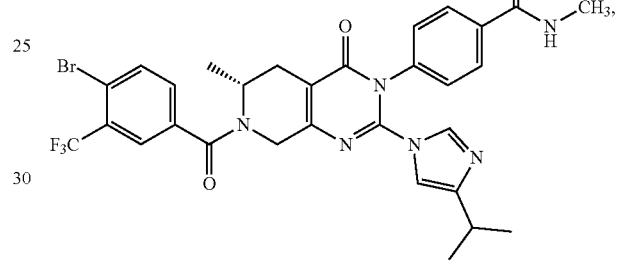
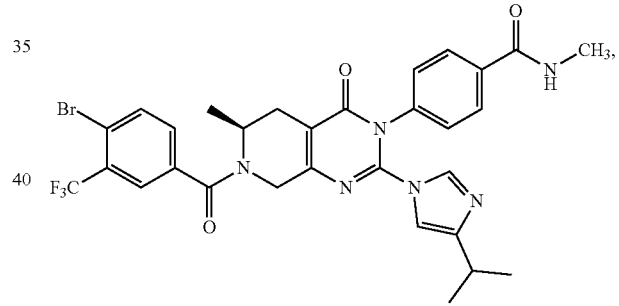
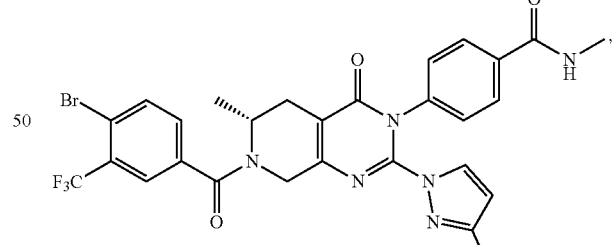
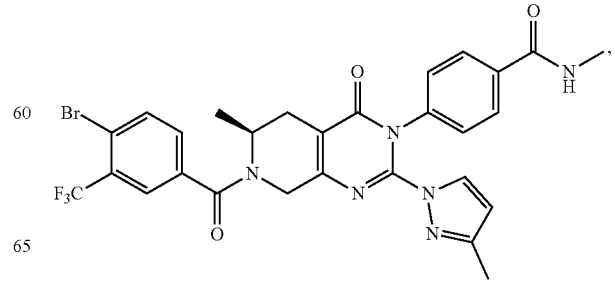

-continued

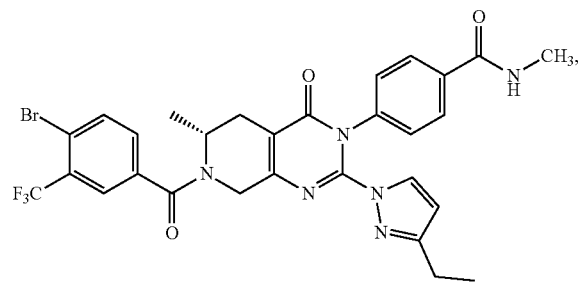

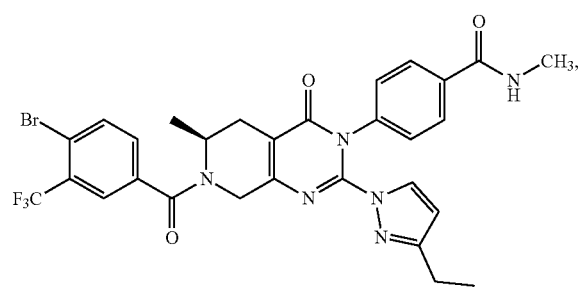

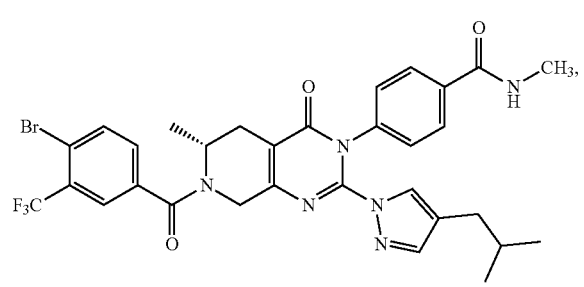

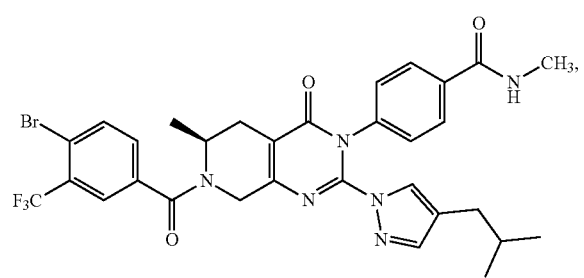

-continued

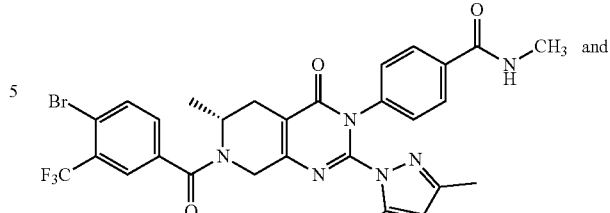

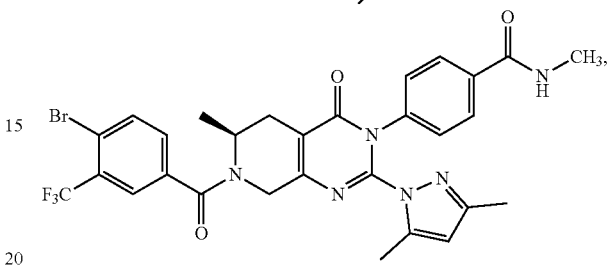

or a pharmaceutically acceptable salt of any of the foregoing.

17. A pharmaceutical composition comprising an effective amount of a compound of claim 1, or a pharmaceutically acceptable salt thereof, and excipient.

18. A method for treating hepatitis B in a subject comprising administering to the subject in need thereof an effective amount of a compound of claim 1, or a pharmaceutically acceptable salt thereof.

19. A method for treating hepatitis D in a subject comprising administering to the subject in need thereof an effective amount of a compound of claim 1, or a pharmaceutically acceptable salt thereof.

20. The method of claim 18, further comprising administering an additional agent selected from the group consisting of an interferon, a nucleoside analog, a nucleotide analog, a sequence specific oligonucleotide, a nucleic acid polymer, an entry inhibitor and a small molecule immunomodulator.

21. The compound of claim 5, wherein the optionally substituted monocyclic heteroaryl is a 5- to 6-member monocyclic heteroaryl that includes 1 to 3 heteroatoms selected from the group consisting of O, S and N, and is optionally substituted with one or more moieties independently selected from the group consisting of halogen, hydroxy, an unsubstituted $C_{1-6}$ alkyl, an unsubstituted $C_{1-6}$ alkoxy and an unsubstituted $C_{1-6}$ haloalkyl.

\* \* \* \* \*

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic HBV-forward primer

<400> SEQUENCE: 1
gtgtctgcgg cgttttatca                                          20

<210> SEQ ID NO 2
<211> LENGTH: 21
<212> TYPE: DNA
<213> ORGANISM: Artificial Sequence
<220> FEATURE:
<223> OTHER INFORMATION: Synthetic HBV-reverse primer

<400> SEQUENCE: 2
gacaaacggg caacatacct t                                        21

<210> SEQ ID NO 3
<211> LENGTH: 28
<212> TYPE: DNA
<213> ORGANISM: Artificial Sequence
<220> FEATURE:
<223> OTHER INFORMATION: Synthetic HBV-probe
<220> FEATURE:
<221> NAME/KEY: modified_base
<222> LOCATION: 1
<223> OTHER INFORMATION: N=FAM-C
<220> FEATURE:
<221> NAME/KEY: modified_base
```

```
<222> LOCATION: 9
<223> OTHER INFORMATION: N=T-ZEN
<220> FEATURE:
<221> NAME/KEY: modified_base
<222> LOCATION: 28
<223> OTHER INFORMATION: N=C-3IABkFQ

<400> SEQUENCE: 3
nctctkcanc ctgctgctat gcctcatn                                              28

<210> SEQ ID NO 4
<211> LENGTH: 40
<212> TYPE: DNA
<213> ORGANISM: Artificial Sequence
<220> FEATURE:
<223> OTHER INFORMATION: Modified Oligonucleotide
<220> FEATURE:
<221> NAME/KEY: modified_base
<222> LOCATION: (1)...(40)
<223> OTHER INFORMATION: Phosphorothioate linkage
<220> FEATURE:
<221> NAME/KEY: modified_base
<222> LOCATION: (1)...(1)
<223> OTHER INFORMATION: 2'-OMe-nucleotide
<220> FEATURE:
<221> NAME/KEY: modified_base
<222> LOCATION: (2)...(2)
<223> OTHER INFORMATION: locked 5-methyl-nucleotide
<220> FEATURE:
<221> NAME/KEY: modified_base
<222> LOCATION: (3)...(3)
<223> OTHER INFORMATION: 2'-OMe-nucleotide
<220> FEATURE:
<221> NAME/KEY: modified_base
<222> LOCATION: (4)...(4)
<223> OTHER INFORMATION: locked 5-methyl-nucleotide
<220> FEATURE:
<221> NAME/KEY: modified_base
<222> LOCATION: (5)...(5)
<223> OTHER INFORMATION: 2'-OMe-nucleotide
<220> FEATURE:
<221> NAME/KEY: modified_base
<222> LOCATION: (6)...(6)
<223> OTHER INFORMATION: locked 5-methyl-nucleotide
<220> FEATURE:
<221> NAME/KEY: modified_base
<222> LOCATION: (7)...(7)
<223> OTHER INFORMATION: 2'-OMe-nucleotide
<220> FEATURE:
<221> NAME/KEY: modified_base
<222> LOCATION: (8)...(8)
<223> OTHER INFORMATION: locked 5-methyl-nucleotide
<220> FEATURE:
<221> NAME/KEY: modified_base
<222> LOCATION: (9)...(9)
<223> OTHER INFORMATION: 2'-OMe-nucleotide
<220> FEATURE:
<221> NAME/KEY: modified_base
<222> LOCATION: (10)...(10)
<223> OTHER INFORMATION: locked 5-methyl-nucleotide
<220> FEATURE:
<221> NAME/KEY: modified_base
<222> LOCATION: (11)...(11)
<223> OTHER INFORMATION: ribo-nucleotide
<220> FEATURE:
<221> NAME/KEY: modified_base
<222> LOCATION: (12)...(12)
<223> OTHER INFORMATION: locked 5-methyl-nucleotide
<220> FEATURE:
<221> NAME/KEY: modified_base
<222> LOCATION: (13)...(13)
<223> OTHER INFORMATION: 2'-OMe-nucleotide
<220> FEATURE:
<221> NAME/KEY: modified_base
<222> LOCATION: (14)...(14)
<223> OTHER INFORMATION: locked 5-methyl-nucleotide
<220> FEATURE:
```

```
<221> NAME/KEY: modified_base
<222> LOCATION: (15)...(15)
<223> OTHER INFORMATION: 2'-OMe-nucleotide
<220> FEATURE:
<221> NAME/KEY: modified_base
<222> LOCATION: (16)...(16)
<223> OTHER INFORMATION: locked 5-methyl-nucleotide
<220> FEATURE:
<221> NAME/KEY: modified_base
<222> LOCATION: (17)...(17)
<223> OTHER INFORMATION: ribo-nucleotide
<220> FEATURE:
<221> NAME/KEY: modified_base
<222> LOCATION: (18)...(18)
<223> OTHER INFORMATION: locked 5-methyl-nucleotide
<220> FEATURE:
<221> NAME/KEY: modified_base
<222> LOCATION: (19)...(19)
<223> OTHER INFORMATION: 2'-OMe-nucleotide
<220> FEATURE:
<221> NAME/KEY: modified_base
<222> LOCATION: (20)...(20)
<223> OTHER INFORMATION: locked 5-methyl-nucleotide
<220> FEATURE:
<221> NAME/KEY: modified_base
<222> LOCATION: (21)...(21)
<223> OTHER INFORMATION: 2'-OMe-nucleotide
<220> FEATURE:
<221> NAME/KEY: modified_base
<222> LOCATION: (22)...(22)
<223> OTHER INFORMATION: locked 5-methyl-nucleotide
<220> FEATURE:
<221> NAME/KEY: modified_base
<222> LOCATION: (23)...(23)
<223> OTHER INFORMATION: ribo-nucleotide
<220> FEATURE:
<221> NAME/KEY: modified_base
<222> LOCATION: (24)...(24)
<223> OTHER INFORMATION: locked 5-methyl-nucleotide
<220> FEATURE:
<221> NAME/KEY: modified_base
<222> LOCATION: (25)...(25)
<223> OTHER INFORMATION: 2'-OMe-nucleotide
<220> FEATURE:
<221> NAME/KEY: modified_base
<222> LOCATION: (26)...(26)
<223> OTHER INFORMATION: locked 5-methyl-nucleotide
<220> FEATURE:
<221> NAME/KEY: modified_base
<222> LOCATION: (27)...(27)
<223> OTHER INFORMATION: 2'-OMe-nucleotide
<220> FEATURE:
<221> NAME/KEY: modified_base
<222> LOCATION: (28)...(28)
<223> OTHER INFORMATION: locked 5-methyl-nucleotide
<220> FEATURE:
<221> NAME/KEY: modified_base
<222> LOCATION: (29)...(29)
<223> OTHER INFORMATION: ribo-nucleotide
<220> FEATURE:
<221> NAME/KEY: modified_base
<222> LOCATION: (30)...(30)
<223> OTHER INFORMATION: locked 5-methyl-nucleotide
<220> FEATURE:
<221> NAME/KEY: modified_base
<222> LOCATION: (31)...(31)
<223> OTHER INFORMATION: 2'-OMe-nucleotide
<220> FEATURE:
<221> NAME/KEY: modified_base
<222> LOCATION: (32)...(32)
<223> OTHER INFORMATION: locked 5-methyl-nucleotide
<220> FEATURE:
<221> NAME/KEY: modified_base
<222> LOCATION: (33)...(33)
<223> OTHER INFORMATION: 2'-OMe-nucleotide
<220> FEATURE:
<221> NAME/KEY: modified_base
<222> LOCATION: (34)...(34)
<223> OTHER INFORMATION: locked 5-methyl-nucleotide
```

```
<220> FEATURE:
<221> NAME/KEY: modified_base
<222> LOCATION: (35)...(35)
<223> OTHER INFORMATION: ribo-nucleotide
<220> FEATURE:
<221> NAME/KEY: modified_base
<222> LOCATION: (36)...(36)
<223> OTHER INFORMATION: locked 5-methyl-nucleotide
<220> FEATURE:
<221> NAME/KEY: modified_base
<222> LOCATION: (37)...(37)
<223> OTHER INFORMATION: 2'-OMe-nucleotide
<220> FEATURE:
<221> NAME/KEY: modified_base
<222> LOCATION: (38)...(38)
<223> OTHER INFORMATION: locked 5-methyl-nucleotide
<220> FEATURE:
<221> NAME/KEY: modified_base
<222> LOCATION: (39)...(39)
<223> OTHER INFORMATION: 2'-OMe-nucleotide
<220> FEATURE:
<221> NAME/KEY: modified_base
<222> LOCATION: (40)...(40)
<223> OTHER INFORMATION: locked 5-methyl-nucleotide

<400> SEQUENCE: 4
acacacacac acacacacac acacacacac acacacacac                40
```